US010383518B2

(12) United States Patent
Abu-Tarif et al.

(10) Patent No.: US 10,383,518 B2
(45) Date of Patent: *Aug. 20, 2019

(54) ELECTRONIC ECOSYSTEM FOR MEDICAL EXAMINATION ROOM

(71) Applicant: MIDMARK CORPORATION, Versailles, OH (US)

(72) Inventors: Asad Abu-Tarif, Irvine, CA (US); Thomas L. Treon, Versailles, OH (US); Steven K. Cordonnier, Bradford, OH (US); Carlos J. Castillo, Huntington Beach, CA (US); Robert Menke, Greenville, OH (US); Ruomei Zhang, Cerritos, CA (US); Jon E. Wells, New Bremen, OH (US)

(73) Assignee: Midmark Corporation, Versailles, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/449,598

(22) Filed: Mar. 3, 2017

(65) Prior Publication Data

US 2017/0172412 A1 Jun. 22, 2017

Related U.S. Application Data

(63) Continuation-in-part of application No. 14/673,947, filed on Mar. 31, 2015.

(51) Int. Cl.
*A61B 5/00* (2006.01)
*A61G 13/00* (2006.01)
(Continued)

(52) U.S. Cl.
CPC .............. *A61B 5/002* (2013.01); *A61B 5/704* (2013.01); *A61G 13/0018* (2013.01);
(Continued)

(58) Field of Classification Search
CPC ... G01G 19/445; H04L 67/1097; H04L 67/12; H04L 67/141; H04L 67/18; A61B 5/002; A61B 5/074; A61B 2560/0437
See application file for complete search history.

(56) References Cited

U.S. PATENT DOCUMENTS 3,870,289 A    3/1975 Aulik
5,669,314 A    9/1997 Grant
(Continued)

FOREIGN PATENT DOCUMENTS

WO    WO-2009018422 A1 *    2/2009    ............ A61G 12/00

*Primary Examiner* — Steven Lim
*Assistant Examiner* — Mancil Littlejohn, Jr.
(74) *Attorney, Agent, or Firm* — Frost Brown Todd LLC

(57) ABSTRACT

A system comprises a storage device, a piece of medical equipment, a portable computing device, and a hub portal. The piece of medical equipment has at least one electrically powered feature and comprises either a medical examination table or a storage cabinet. The storage device is operable to store data and is remotely located relative to the first piece of medical equipment and relative to the portable computing device. The hub portal is operable to provide communication of one or both of data or commands between the storage device, the piece of medical equipment, and the portable computing device. A method includes enablement or activation of an electrically powered feature of medical equipment upon entry of a portable computing device into a medical examination room. The method also includes disablement or further activation of the electrically powered feature upon exit of the portable computing device from the medical examination room.

18 Claims, 46 Drawing Sheets

(51) Int. Cl.
*H04W 4/80* (2018.01)
*G01G 19/44* (2006.01)
*G16H 10/60* (2018.01)
*G16H 40/67* (2018.01)
*H04L 29/08* (2006.01)
*G16H 40/63* (2018.01)

(52) U.S. Cl.
CPC ........... *G01G 19/445* (2013.01); *G16H 10/60* (2018.01); *G16H 40/67* (2018.01); *H04L 67/1097* (2013.01); *H04L 67/12* (2013.01); *H04W 4/80* (2018.02); *A61B 2560/0437* (2013.01); *A61G 2203/44* (2013.01); *G16H 40/63* (2018.01)

(56) References Cited

U.S. PATENT DOCUMENTS

| | | |
|---|---|---|
| 6,021,534 A | 2/2000 | Koch |
| 6,342,840 B1 | 1/2002 | Dunn |
| 7,610,057 B2 * | 10/2009 | Bahl ..................... H04W 88/06 455/432.3 |
| 8,292,807 B2 * | 10/2012 | Perkins ................ A61B 5/0002 600/301 |
| 8,978,181 B2 * | 3/2015 | Menke ................ A61G 13/0018 5/611 |
| 2005/0191716 A1 | 9/2005 | Surwit et al. |
| 2007/0180917 A1 | 8/2007 | Farnet et al. |
| 2007/0216517 A1 * | 9/2007 | Kurpinski ........... B60R 25/2036 340/5.72 |
| 2009/0250983 A1 | 10/2009 | Maier et al. |
| 2010/0022902 A1 | 1/2010 | Lee et al. |
| 2010/0113895 A1 | 5/2010 | Cho et al. |
| 2010/0138238 A1 * | 6/2010 | Sobie ................... G06Q 10/087 705/3 |
| 2010/0283361 A1 | 11/2010 | Sato et al. |
| 2011/0185035 A1 | 7/2011 | Van |
| 2011/0317816 A1 | 12/2011 | Bechard et al. |
| 2013/0247300 A1 | 9/2013 | Menke et al. |
| 2014/0163726 A1 | 6/2014 | Shoenfield et al. |

* cited by examiner

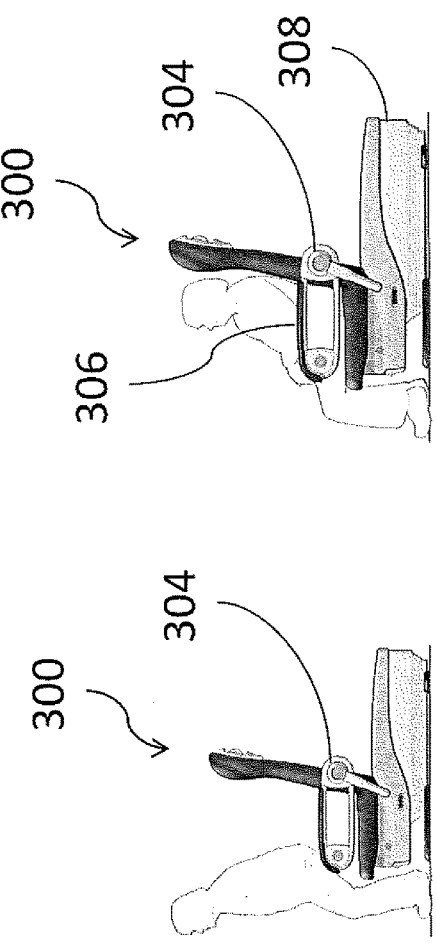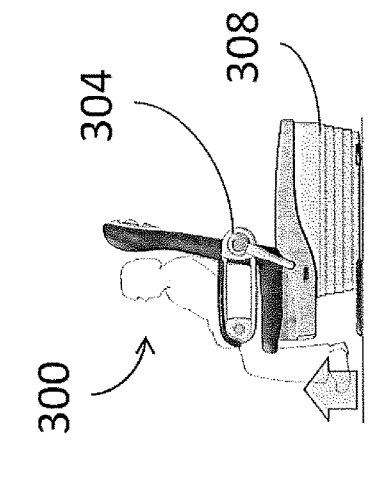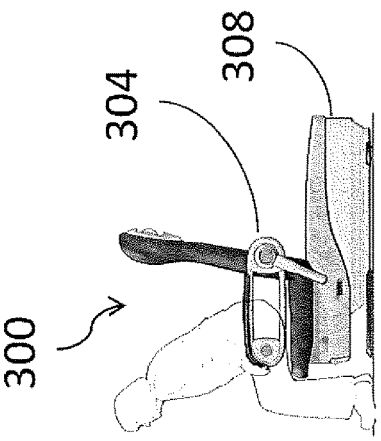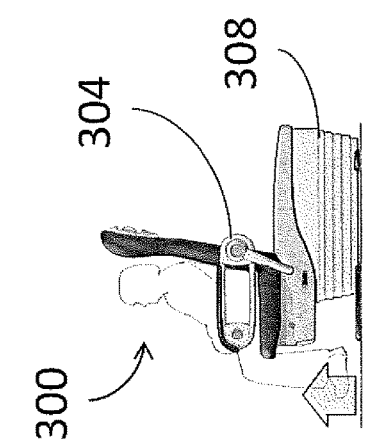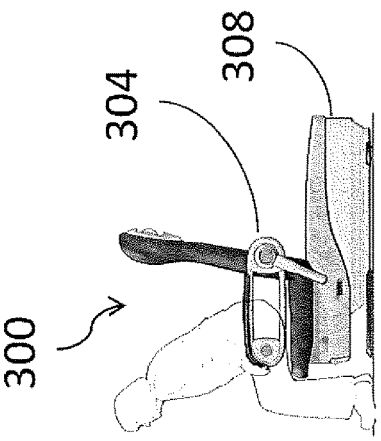

ELECTRONIC ECOSYSTEM FOR MEDICAL EXAMINATION ROOM

BACKGROUND

Some conventional medical and dental examination rooms include a variety of kinds of equipment that are completely independent of each other and that require separate interaction with medical personnel. Such equipment may include, among other things, an examination table, equipment used to measure biological data associated with a patient, a computing device providing read/write access to a patient's electronic medical record (EMR), cabinets containing medicine and/or other medical equipment, etc. At least some of this equipment may include combinations devices that include one or more of these functions, such as an examination table containing a patient weight sensor. In addition, at least some of this equipment may include one or more components that are electrically actuated, electrically powered, or otherwise electrically driven. For instance, an examination table may include powered components that raise and lower at least part of the patient vertically relative to the ground, a powered backrest that transitions the patient between a generally upright seated position and a generally supine position, a powered armrest that raises and lowers a patient's arm, and/or other components that provide some form of powered motion. Equipment that is used to measure biological data associated with a patient may include various kinds of sensors, processors, etc. that are operable to sense and process biological parameters such as weight, temperature, blood pressure, height, etc. Computing devices that provide access to a patient's EMR may include various kinds of user input features, processors, and data communication features that are operable to interface with the equipment described herein. A cabinet that contains medicine and/or other medical equipment may include an electrically powered locking device that locks or unlocks the cabinet in response to an electric control signal.

It may be desirable to provide a device that serves as a hub for computing devices and various kinds of medical or dental examination room equipment that are electrically actuated, electrically powered, or otherwise electrically driven. Such a hub device may establish an ecosystem of devices in the medical or dental examination room, providing a degree of centralized communication and control with such other equipment. Such a device may be a standalone device or may be integrated into one or more of the devices (e.g., examination table, computing device, etc.) in the medical examination room.

While several devices and methods have been made and used in a medical or dental examination room, it is believed that no one prior to the inventors has made or used the inventions described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 47 depicts a side elevation view of an exemplary medical examination table with which the set of steps of FIG. 46 may be performed, with a patient approaching the examination table;

FIG. 48 depicts a side elevation view of the medical examination table of FIG. 41, with the patient seated on the medical examination table;

FIG. 49 depicts a side elevation view of the medical examination table of FIG. 41, with the patient's weight being checked;

FIG. 50 depicts a side elevation view of the medical examination table of FIG. 41, with the patient's vitals being checked;

FIG. 51 depicts a side elevation view of the medical examination table of FIG. 41, with the patient being raised to a lifted position for examination;

FIG. 52 depicts a side elevation view of the medical examination table of FIG. 41, with the patient leaving the medical examination table;

Figure 1:
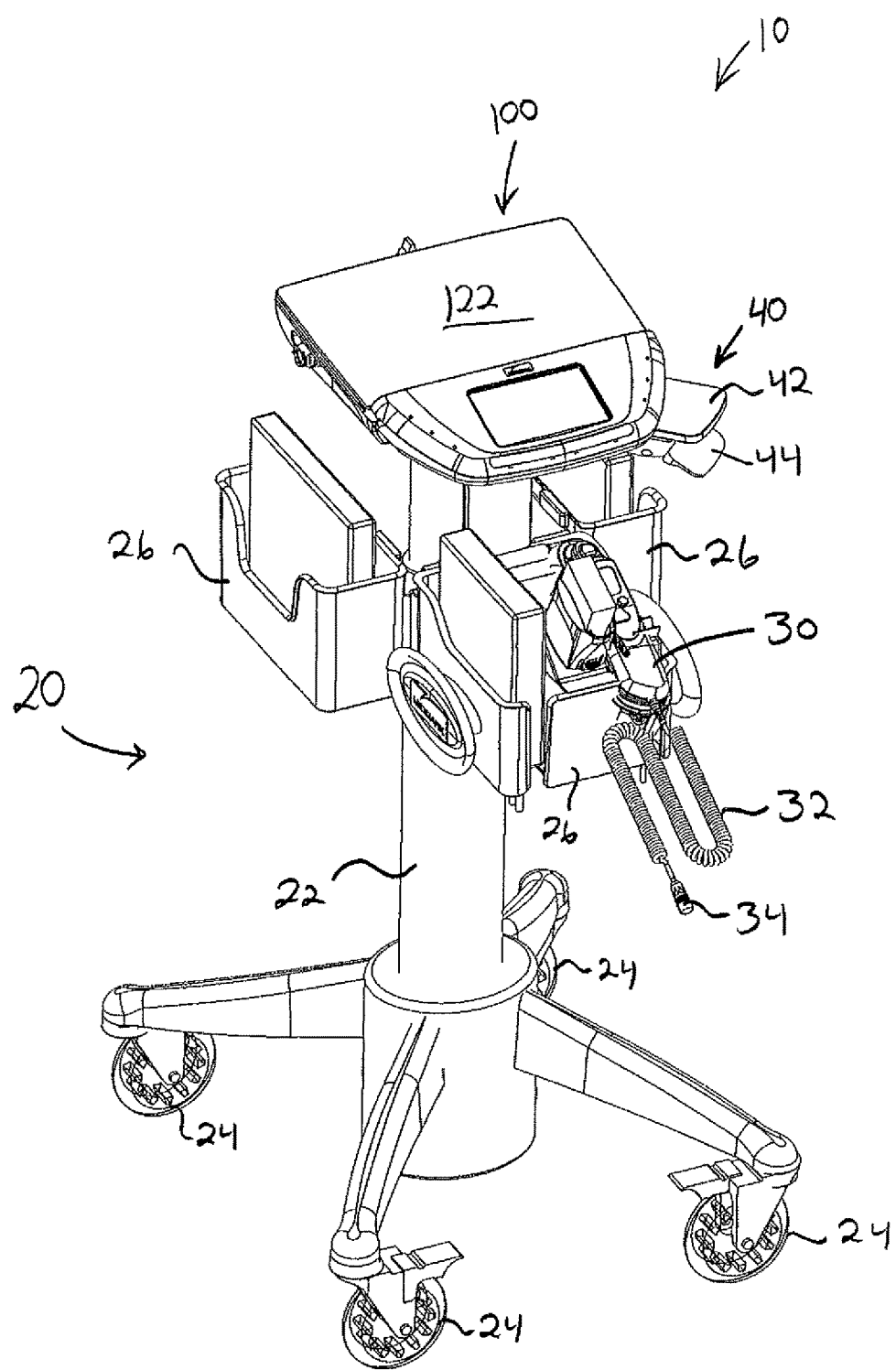
FIG. 1 depicts a perspective view of an exemplary communication hub assembly that may be used in a medical examination room.
Figure 2:
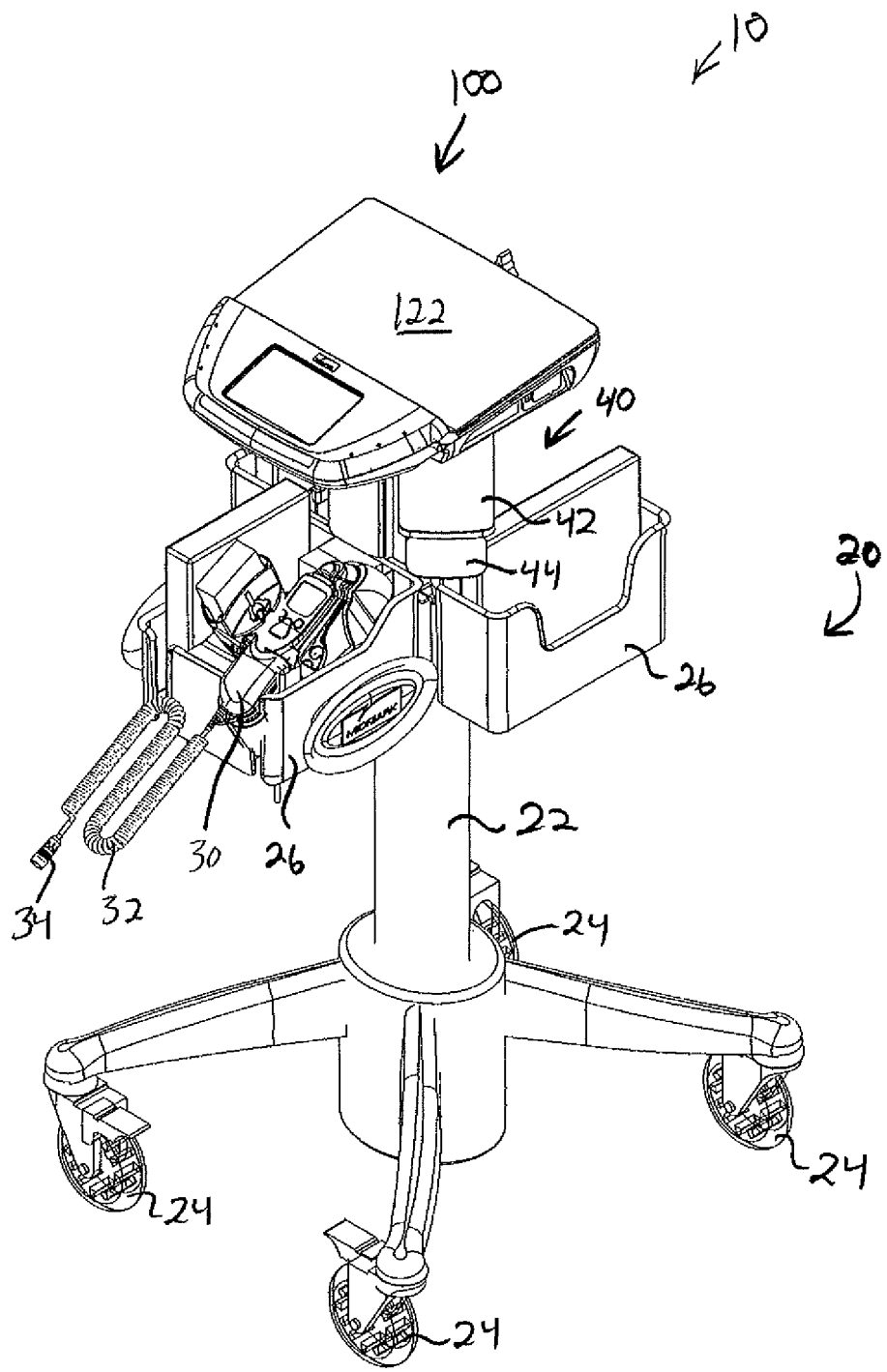
FIG. 2 depicts another perspective view of the communication hub assembly of FIG. 1.
Figure 3:
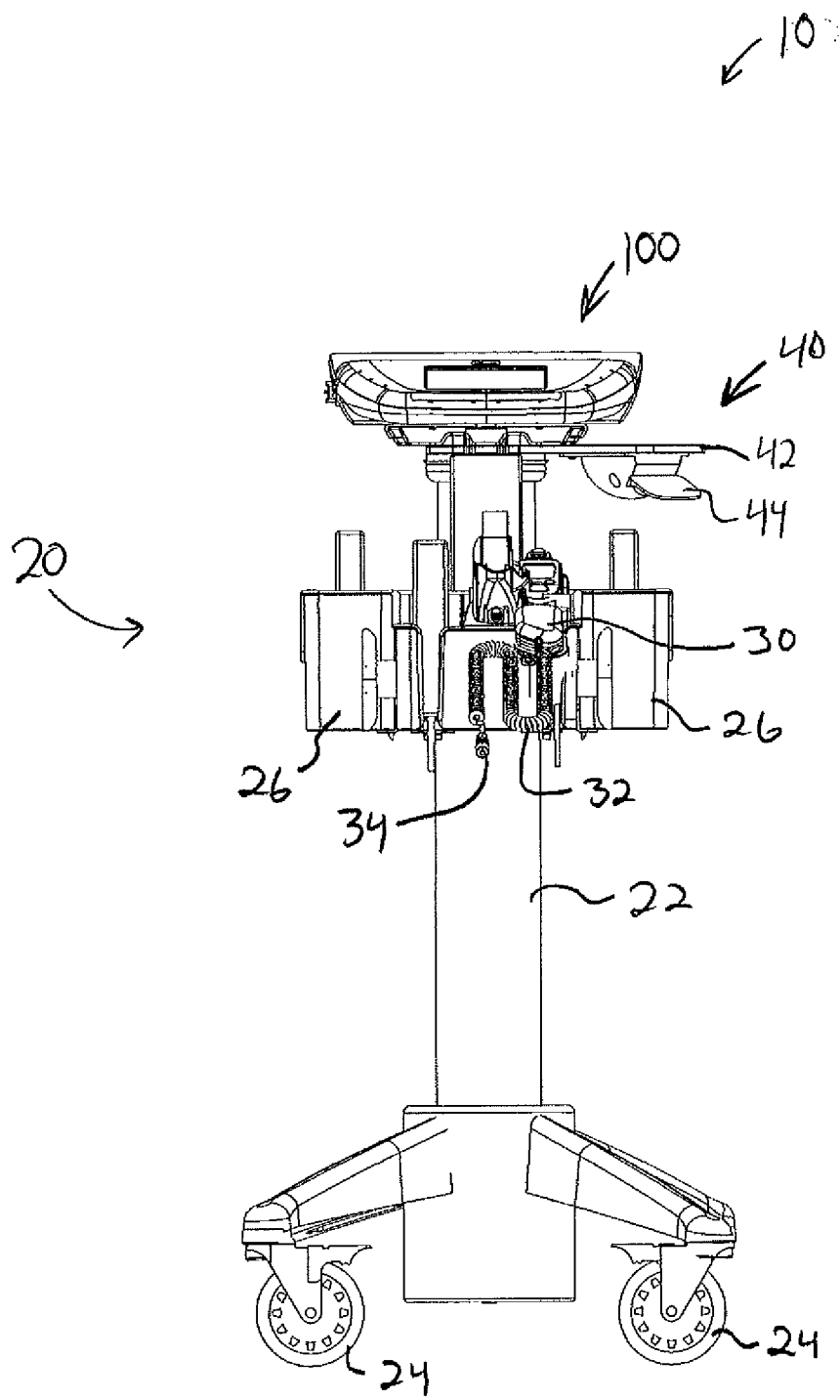
FIG. 3 depicts a front elevational view of the communication hub assembly of FIG. 1.
Figure 4:
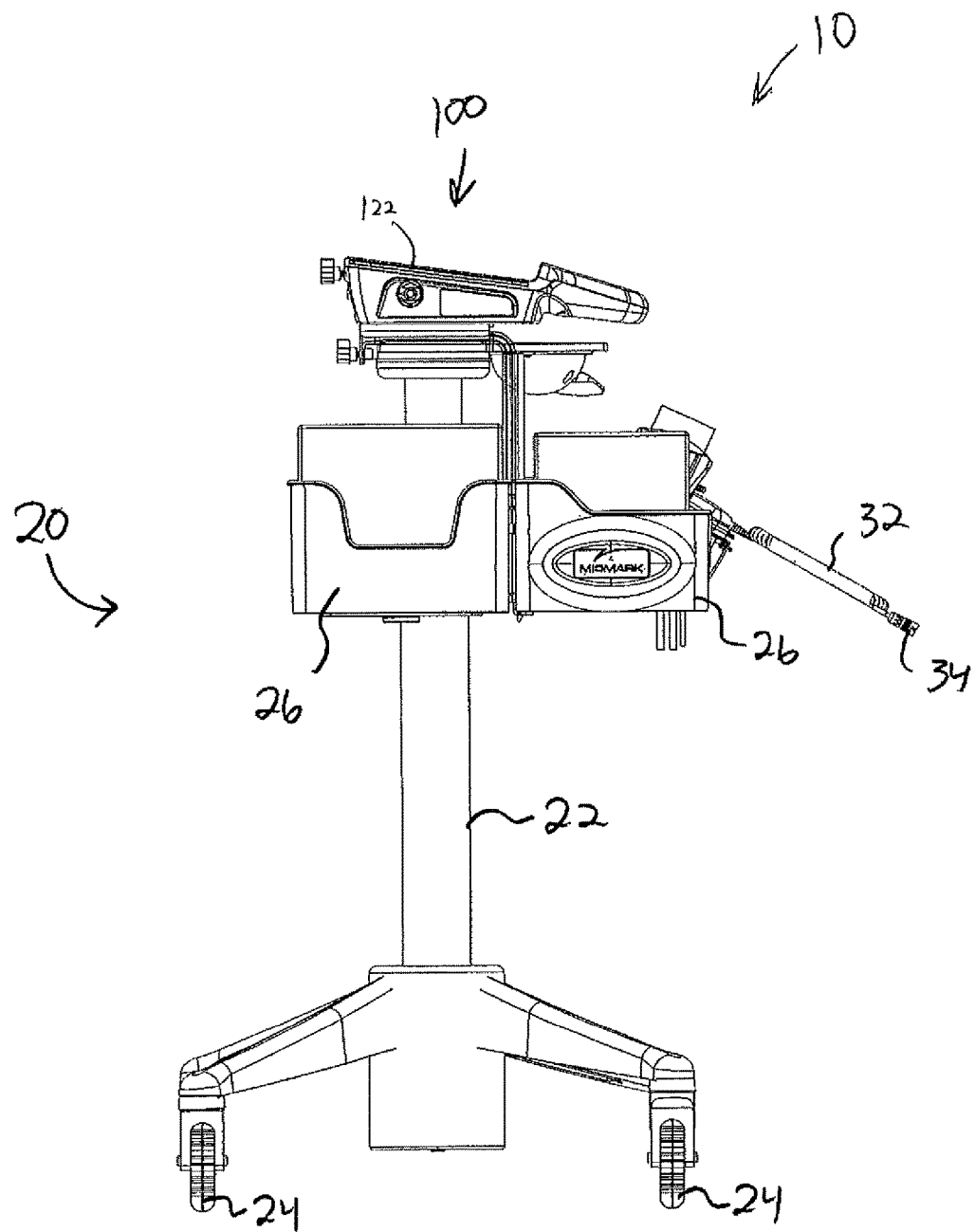
FIG. 4 depicts a left side elevational view of the communication hub assembly of FIG. 1.
Figure 5:
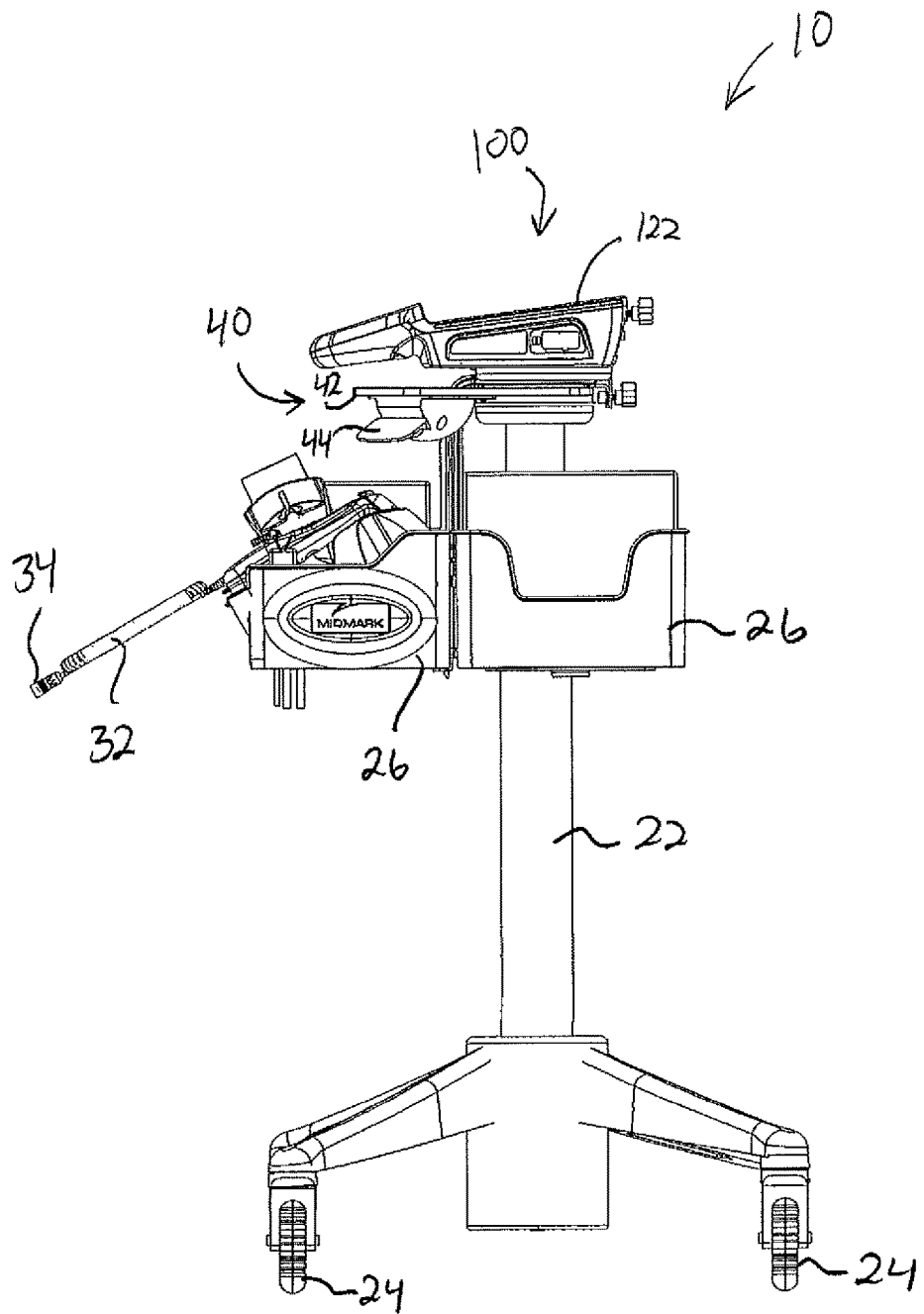
FIG. 5 depicts a right side elevational view of the communication hub assembly of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Communication Hub Assembly

A. Overview

FIGS. 1-5 show an exemplary communication hub assembly (10) that may be used in a medical examination room. While communication hub assembly (10) is described as being used in a medical examination room in various examples provided herein, it should be understood that communication hub assembly (10) may be used in a variety of other settings as well. By way of example only, the teachings herein may be readily applied to the context of a dental examination room, veterinary examination room, and various other contexts. Various other settings in which communication hub assembly (10) may be used will be apparent to those of ordinary skill in the art in view of the teachings herein.

Communication hub assembly (10) of the present example comprises a cart (20) and a communication hub platform device (100). Cart (20) of the present example comprises a column (22) with a set of wheels (24) and accessory compartments (26). Hub platform device (100) is secured to the top of column (22). Column (22) comprises at least two axially aligned tubular segments arranged in a telescoping relationship, such that the effective height of column (22) may be adjusted as will be described in greater detail below. Wheels (24) enable cart (20) to be readily transported along the ground. Wheels (24) may be selectively locked, using known structures and techniques, to secure the position of cart (20). Accessory compartments (26) are configured to hold various items such as binders, etc. In the example shown, a digital thermometer (30) is shown in one accessory compartment (26). Digital thermometer (30) includes a cord (32) with a plug (34) that is configured to couple with hub platform device (100) as will be described in greater detail below. Other suitable items that may be placed in accessory compartments (26) will be apparent to those of ordinary skill in the art in view of the teachings herein. It should also be understood that accessory compartments (26) may be modified, substituted, supplemented, or omitted as desired.

A height adjustment assembly (40) extends transversely from column (22), just below hub platform device (100). Height adjustment assembly (40) comprises a fixed paddle (42) and a movable paddle (44). Movable paddle (44) is pivotable toward and away from fixed paddle (42). In particular, movable paddle (44) is pivotable toward fixed paddle (42) to unlock the vertical position of an upper telescoping segment of column (22) relative to a lower telescoping segment of column (22), thereby enabling an operator to adjust the effective height of column (22). Once the operator releases movable paddle (44), a resilient member (e.g., torsion spring, leaf spring, coil spring, etc.) biases movable paddle (44) pivotably away from fixed paddle (42), such that movable paddle (44) returns to the position shown in FIGS. 1-6. This return of movable paddle (44) to the position shown in FIGS. 1-6 locks the vertical position of an upper telescoping segment of column (22) relative to a lower telescoping segment of column (22), thereby locking the adjusted effective height of column (22). Various suitable components that may be used to provide such height adjustment capabilities will be apparent to those of ordinary skill in the art in view of the teachings herein. It should also be understood that some versions of cart (20) may simply lack height adjustment capabilities.

B. Exemplary Communication Hub Platform Device

FIGS. 6-15 show communication hub platform device (100) in greater detail. Communication hub platform device (100) comprises an upper housing (120) and a lower housing (140), which together contain internal components (160). A bracket (170) is fixedly secured to the bottom of lower housing (120). Bracket (170) is configured to complement features at the top of column (22) to thereby secure communication hub platform device (100) to cart (20). In some versions, while bracket (170) may be rigidly secured to column (22), bracket (170) is configured to be selectively removed from column (22) by an operator of assembly (10). Various suitable ways in which bracket (170) may be removably (or non-removably) secured to column (22) will be apparent to those of ordinary skill in the art in view of the teachings herein.

Figure 12:
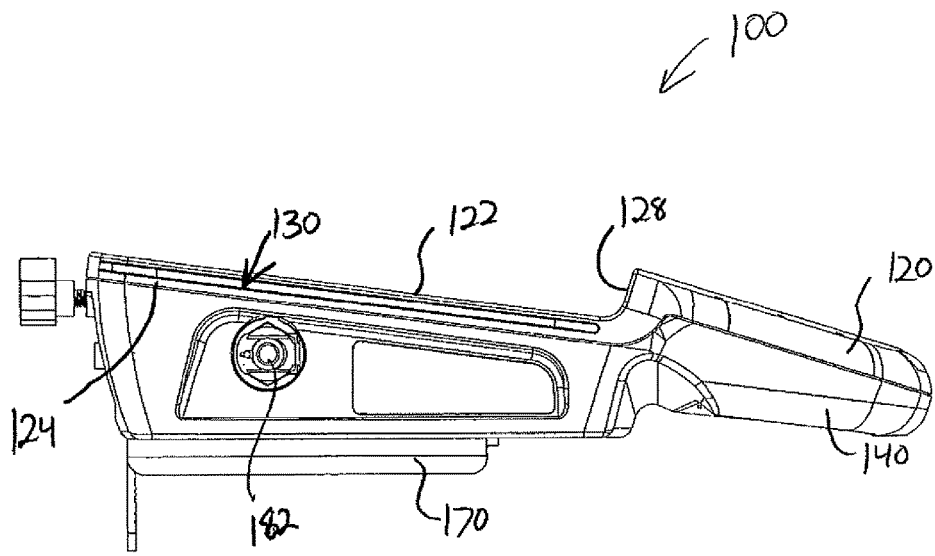
FIG. 12 depicts a left side elevational view of the communication hub platform device of FIG. 6.
Figure 13:
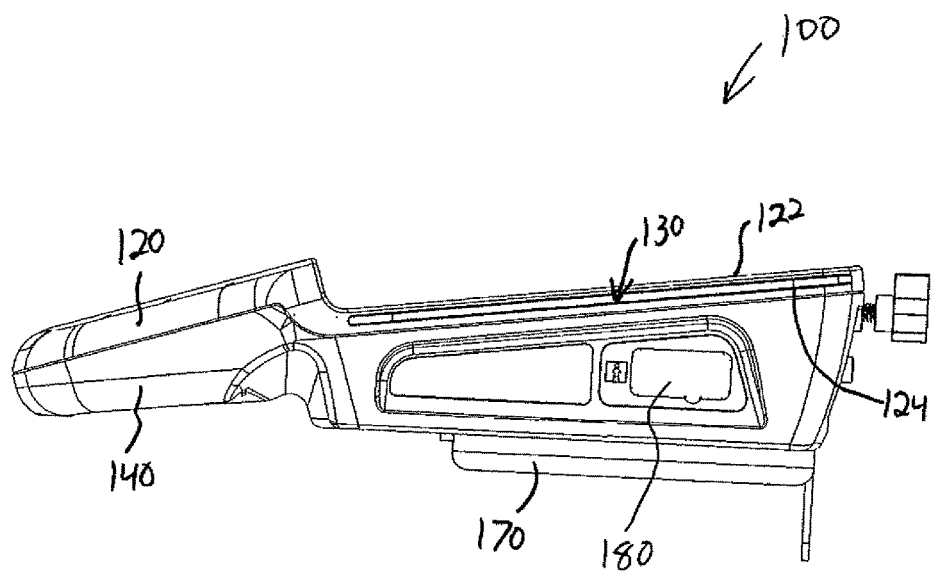
FIG. 13 depicts a right side elevational view of the communication hub platform device of FIG. 6.
Figure 14:
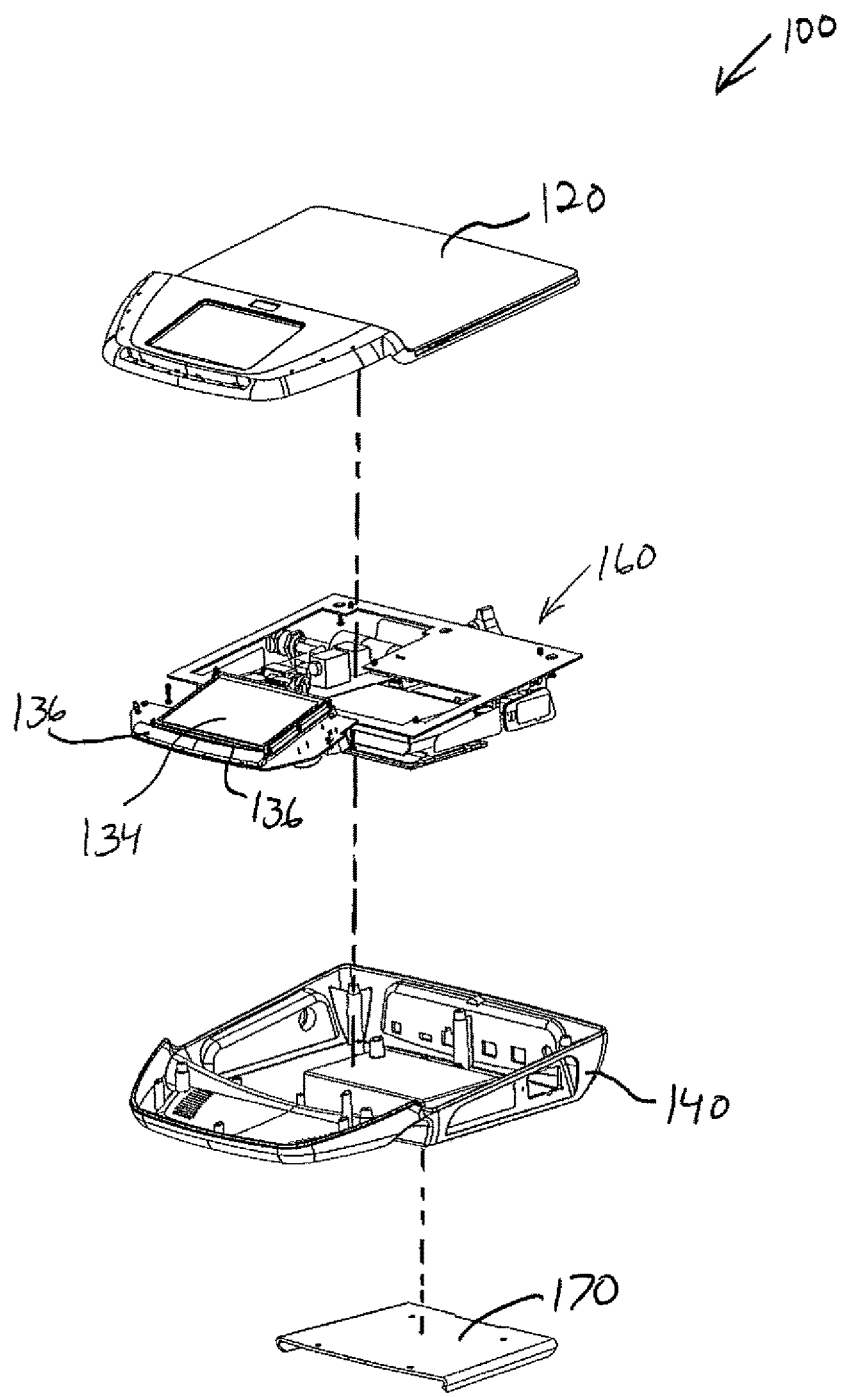
FIG. 14 depicts an exploded perspective view of the communication hub platform device of FIG. 6.

Upper housing (120) includes an upwardly presented surface (122) that is bounded by lateral edges (124), a distal edge (126), and a proximal ledge (128). Each lateral edge (124) includes a respective mounting channel (130) as will be described in greater detail below. As best seen in FIGS. 12-13, surface (122) is oriented at an oblique angle relative to the horizontal plane. Surface (122) is sized and configured to enable placement of items such as mobile computing devices, etc., on surface (122) as will be described in greater detail below. Proximal ledge (128) is configured to serve as a rest for items placed on surfaces (122), preventing such items from sliding off of the proximal side of communication hub platform device (100).

Upper housing (120) further includes a window (132), which permits viewing of a screen (134). In the present example, screen (134) is configured to display information relating to vital signs and/or other biological information associated with the patient. Screen (134) also provides a touchscreen interface for an operator to provide commands to hub platform device (100) and/or to equipment that is coupled with hub platform device (100).

The proximal end of communication hub platform device (100) further includes a pair of light emitting features (136). In the present example, the light emitting features (136) are operable to provide visual alarms in response to various conditions. For instance, such conditions may relate directly to the condition of the hub platform device (100) (e.g., low battery, other malfunction), the condition of equipment that is coupled with the hub platform device (100), a faulty connection between the hub platform device (100) and associated equipment, a condition of the patient, and/or various other conditions. In some instances, light emitting features (136) emit light of different colors (e.g., red and yellow). Various suitable ways in which light emitting features (136) may be used to provide an indication of various kinds of conditions will be apparent to those of ordinary skill in the art in view of the teachings herein.

Communication hub platform device (100) further comprises a plurality of ports (180, 182, 184, 186, 188, 190, 192) that are configured to provide one-way or two-way wired communication and/or other kinds of communication with other devices. Each of these ports (180, 182, 184, 186, 188, 190, 192) will be described in greater detail below. It should be understood, however, that these ports (180, 182, 184, 186, 188, 190, 192) are merely illustrative examples. Any of these ports (180, 182, 184, 186, 188, 190, 192) may be omitted if desired. In addition or in the alternative, any suitable kinds of additional ports may be added to communication hub platform device (100). Various suitable combinations of ports that may be incorporated into communication hub platform device (100) will be apparent to those of ordinary skill in the art in view of the teachings herein.

Figure 6:
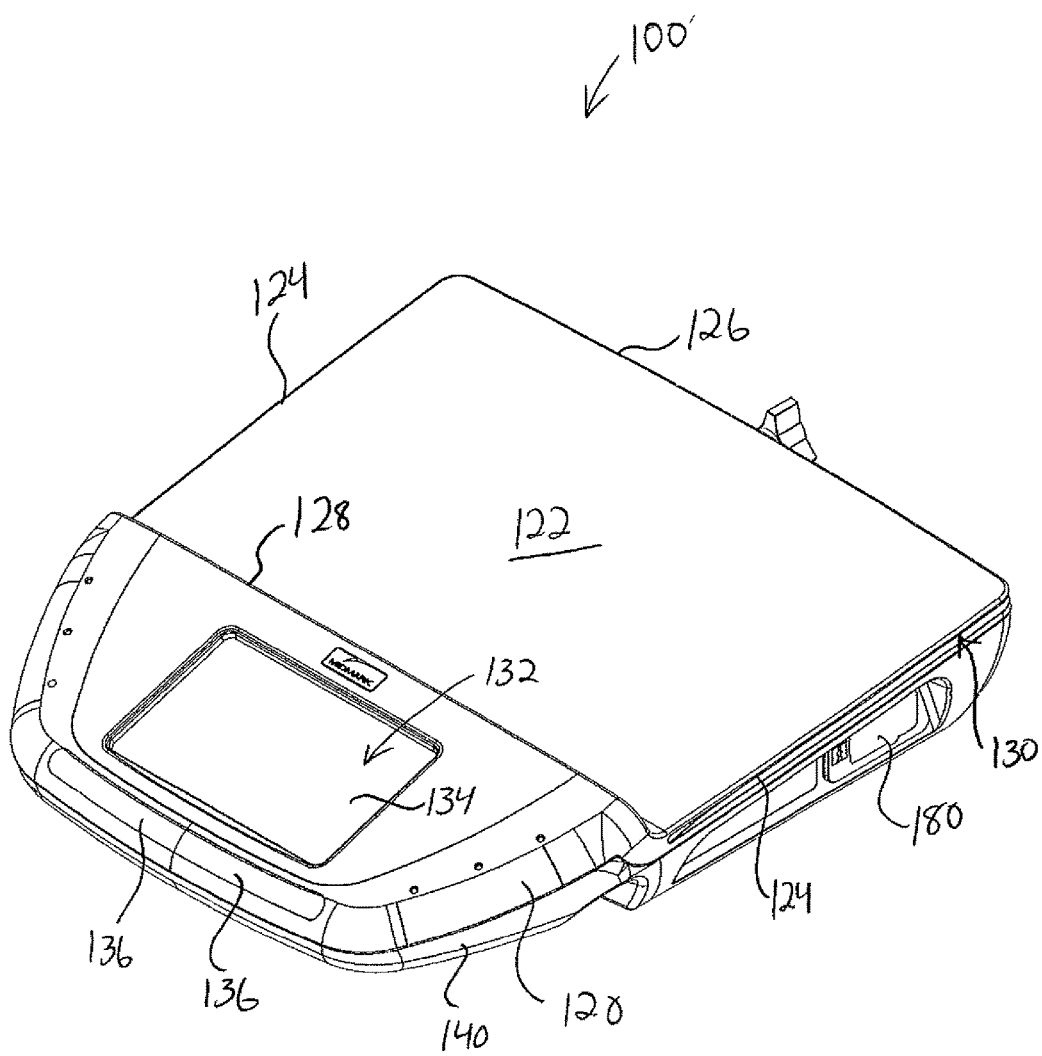
FIG. 6 depicts a perspective view of a communication hub platform device of the communication hub assembly of FIG. 1.
Figure 7:
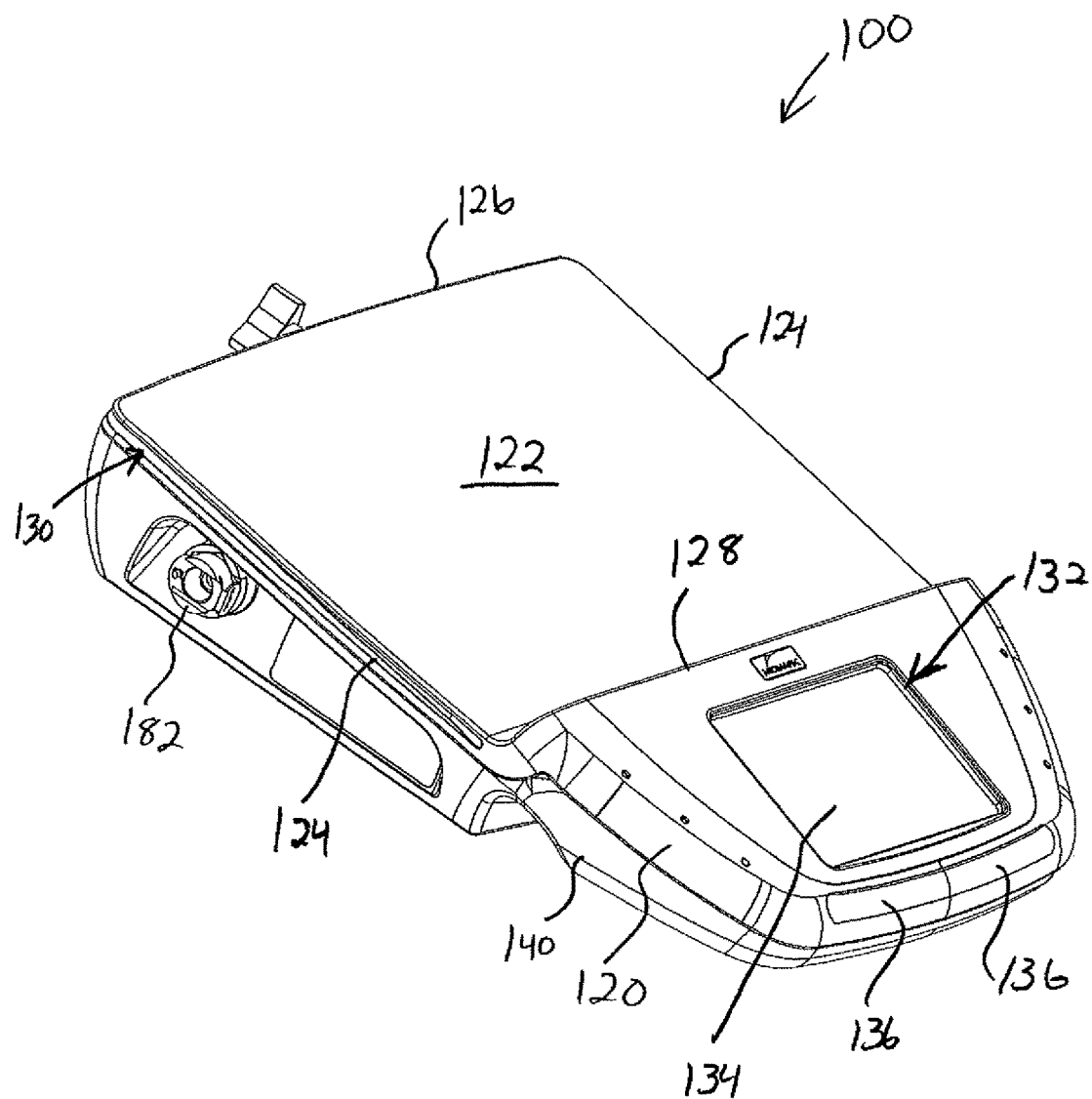
FIG. 7 depicts another perspective view of the communication hub platform device of FIG. 6.
Figure 8:
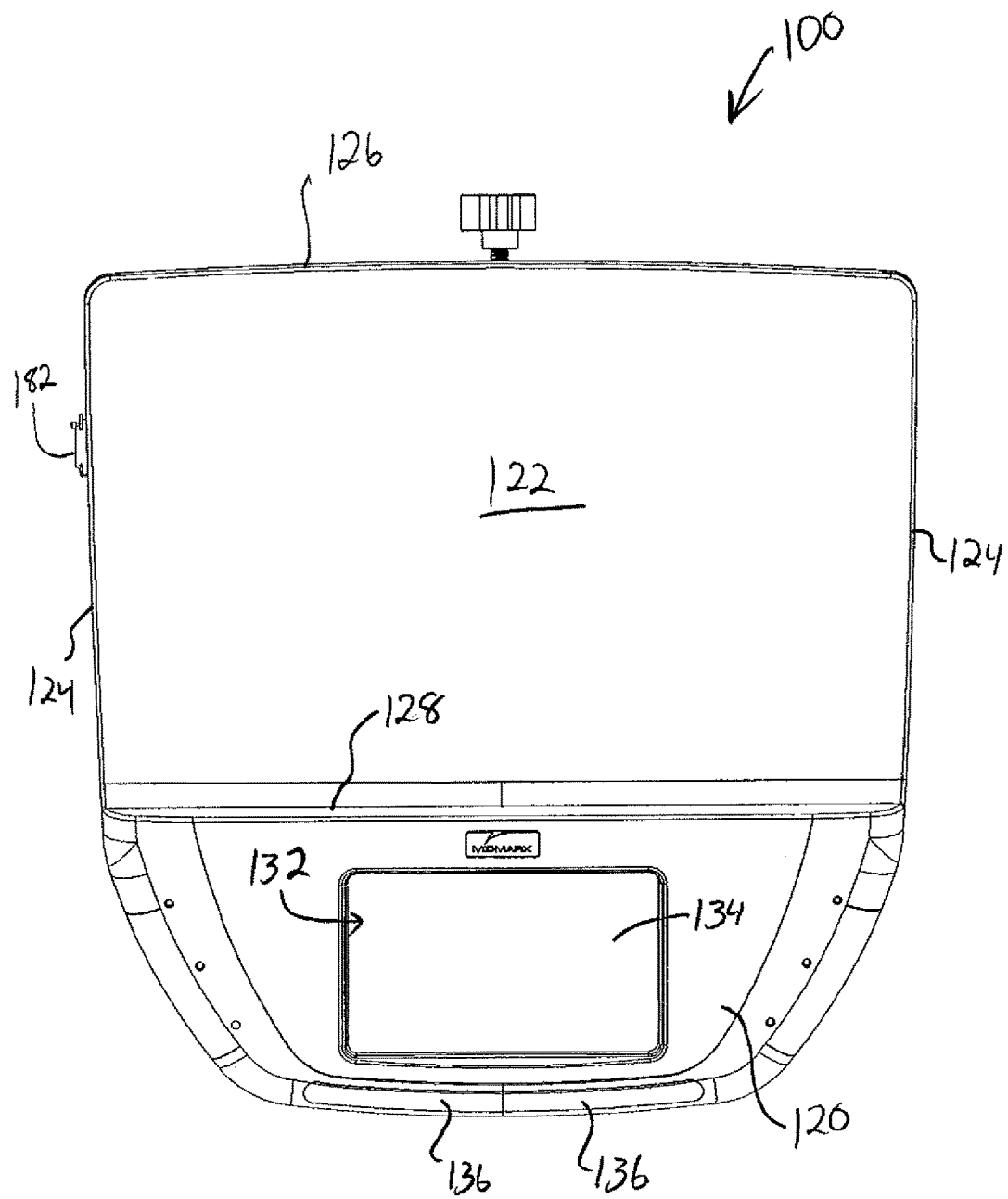
FIG. 8 depicts a top plan view of the communication hub platform device of FIG. 6.
Figure 9:
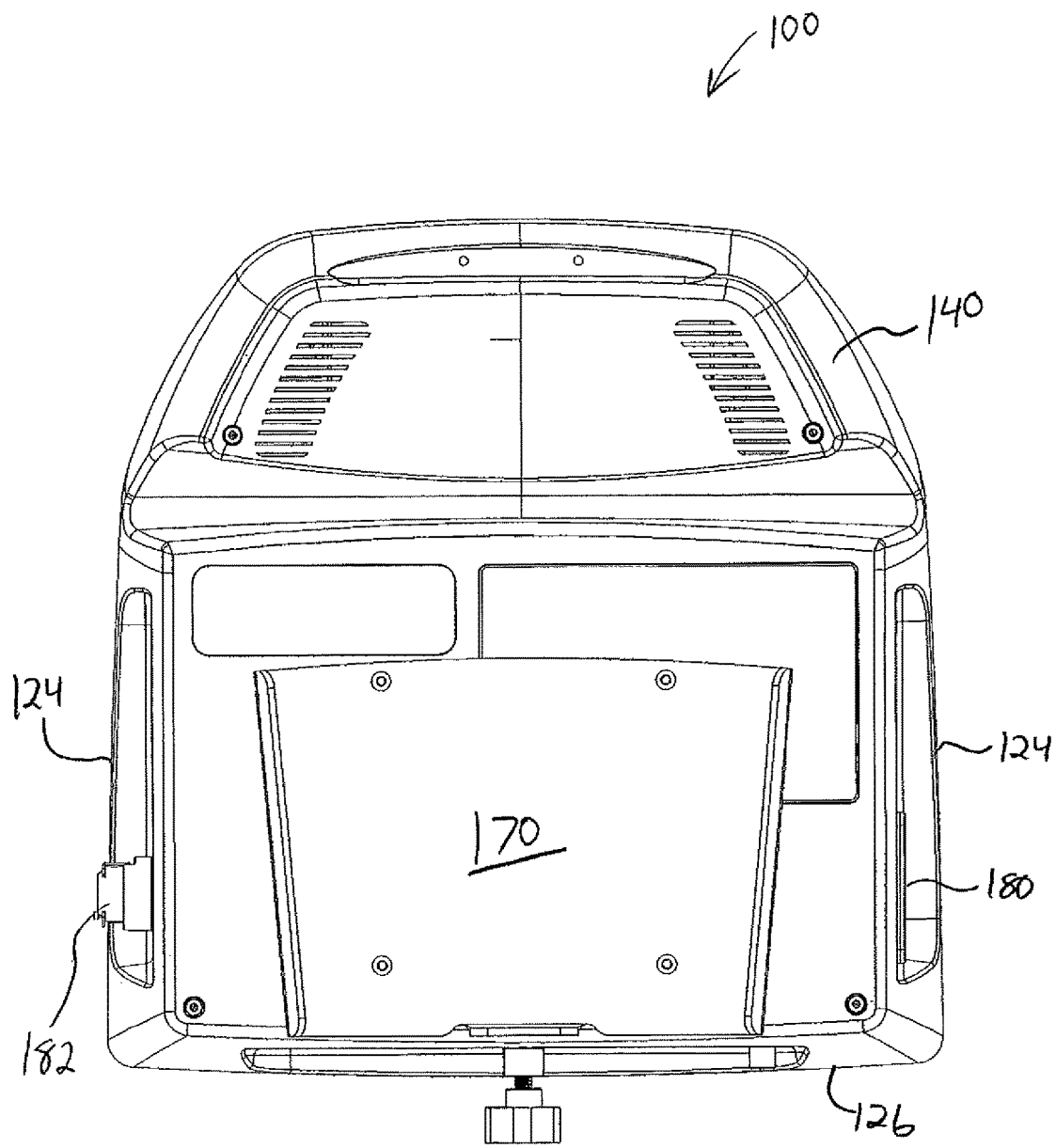
FIG. 9 depicts a bottom plan view of the communication hub platform device of FIG. 6.
Figure 10:
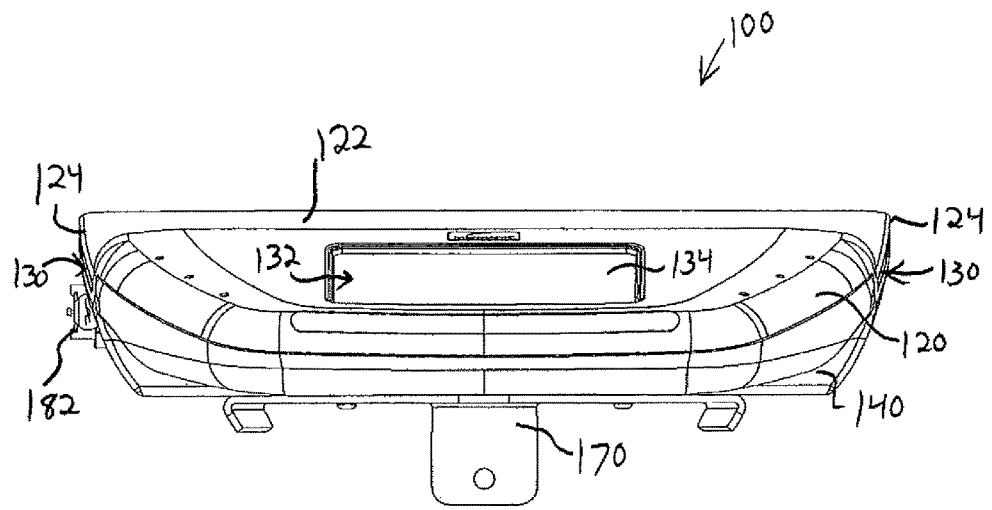
FIG. 10 depicts a front elevational view of the communication hub platform device of FIG. 6.

As best seen in FIGS. 6 and 13, the right-hand side of communication hub platform device (100) comprises a port (180) that is configured to couple with an oxygen saturation ($SO_2$) monitoring device (not shown). Communication hub platform device (100) may thus receive oxygen saturation ($SO_2$) readings via port (180). As best seen in FIGS. 7 and 12, the left-hand side of communication hub platform device (100) comprises a port (182) that configured to couple with a non-invasive blood pressure measurement (NIBPM) cuff assembly. In particular, such a cuff assembly comprises a set of tubes (an air inlet tube and an air outlet tube) that are both coupled with a plug. Port (182) is configured to receive such a plug and is thereby operable to couple the cuff with a NIBPM module (167) within communication hub platform device (100) as will be described in greater detail below.

Figure 11:
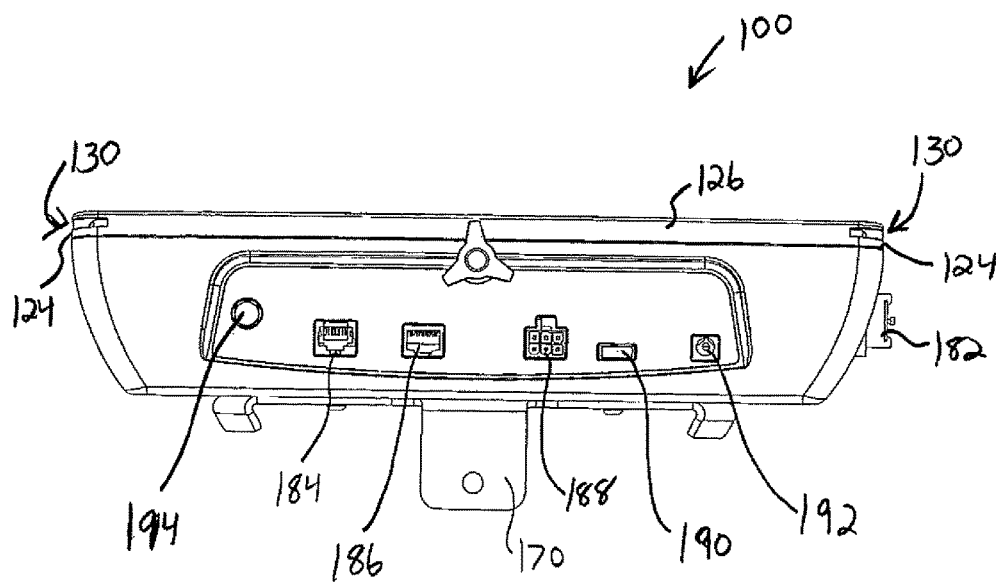
FIG. 11 depicts a rear elevational view of the communication hub platform device of FIG. 6.

As best seen in FIG. 11, the distal side of communication hub platform device (100) comprises a plurality of ports (184, 186, 188, 190, 192). Port (184) comprises a conventional RJ45 port that is operable to couple with a cable that is further coupled with a patient examination table (300). For instance, such a patient examination table (300) may be operable to detect a patient's weight as described below, and communication hub platform device (100) may receive the patient's weight via the cable coupled with port (184). In addition, communication hub platform device (100) may transmit commands to a patient examination table (300) via a cable coupled with port (184). Such commands may include commands that operate powered features of the patient examination table (300), such as powered components that raise and lower at least part of the patient vertically relative to the ground, a powered backrest that transitions the patient between a generally upright seated position and a generally supine position, a powered armrest that raises and lowers a patient's arm, and/or other components that provide some form of powered motion.

Port (186) comprises a conventional RJ50 port. Port (186) is operable to couple with plug (34) of digital thermometer (30) as described above. Communication hub platform device (100) may thus receive patient temperature readings via port (186). Port (188) comprises a custom USB port that is operable to provide communication between communication hub platform device (100) and a personal computer and/or other kind of computing device. Port (190) comprises a conventional USB port. In the present example, port (190) is used to provide firmware upgrades to communication hub platform device (100).

Port (192) comprises a socket that is configured to receive a complementary plug of a power cord, such that a battery pack (164) within communication hub platform device (100) is rechargeable through power through port (192). In some other versions, communication hub platform device (100) comprises features enabling battery pack (164) to be charged via inductive charging, such that port (192) may be omitted if desired. It should also be understood that, in some instances, communication hub platform device (100) may receive operational power via port (192) (e.g., when battery pack (164) is depleted or omitted, etc.). Moreover, some other kind of port (e.g., USB port, etc.) may be used to provide charging of battery pack (164) and/or operational power for communication hub platform device (100).

The distal side of communication hub platform device (100) further comprises a power button (194) that is operable to toggle communication hub platform device (100) between an on and off state. Various suitable forms that power button (194) may take will be apparent to those of ordinary skill in the art in view of the teachings herein.

In some versions, communication hub platform device (100) comprises an additional Ethernet port, USB port, and/or other kind of port that provides a wired connection with one or more other computing devices, a local area network, a wide area network, etc. Such an additional communication port may be used to transmit patient data via cable to an EMR system. Other suitable ways in which one or more additional communication ports may be used will be apparent to those of ordinary skill in the art in view of the teachings herein.

Figure 15:
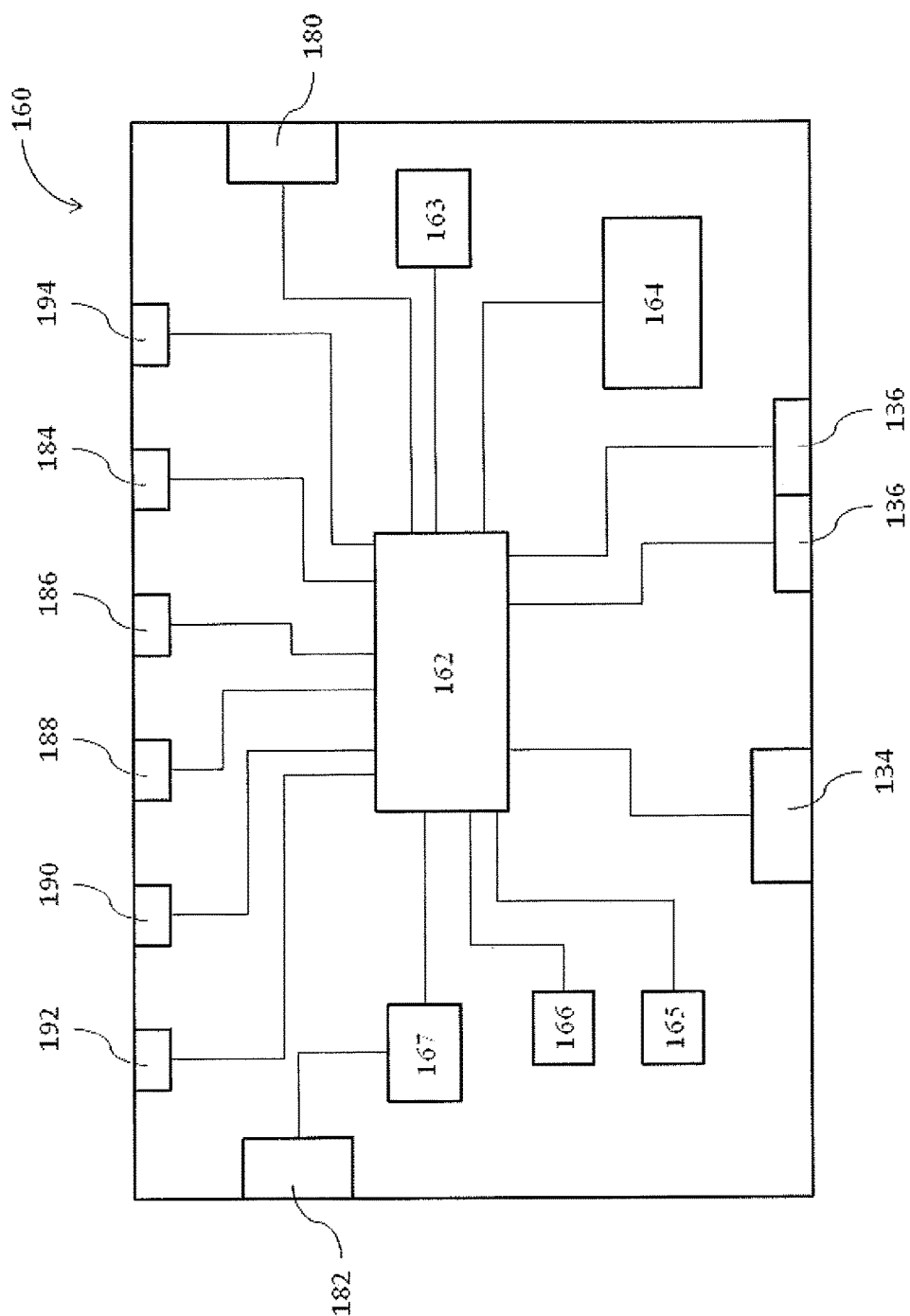
FIG. 15 depicts a block schematic view of internal components of the communication hub platform device of FIG. 6.

FIG. 15 shows internal components (160) in block schematic form. It should be understood that these internal components (160) are merely illustrative examples. It is contemplated that various other internal components (160) may be used in addition to or in lieu of those described below. The below examples should therefore not be read as being limiting in any way. As shown, internal components (160) comprise a processing module (162), a storage device (163), a battery pack (164), a near field communication (NFC) module (165), a low energy Bluetooth (BLE) communication module (166), and a NIBP module (167). Processing module (162) is in communication with ports (180, 184, 186, 188, 190, 192), power button (194), storage device (163), battery pack (164), light emitting features (136), display screen (134), near field communication (NFC) module (165), low energy Bluetooth (BLE) communication module (166), and NIBP module (167). In particular, processing module (162) is configured to process data and/or commands that are delivered through ports (180, 184, 186, 188, 190, 192). Processing module (162) is also configured to deliver data and/or commands through ports (180, 184, 186, 188, 190, 192). Various examples of data and/or commands being delivered to and/or from processing module (162) will be described in greater detail below. Various suitable components and configurations that may be used to form processing module (162) will be apparent to those of ordinary skill in the art in view of the teachings herein. It should also be understood that, while processing module (162) is referred to as a "module," processing module (162) may in fact be formed by several modules that are spaced apart yet in communication with each other.

Processing module (162) is operable to retrieve data from storage device (163) and store data in storage device (163). For instance, storage device (163) may include various control algorithms that are communicated to processing module (162) and are executed by processing module (162). Processing module (162) may also store patient data and/or other data on storage device (163). Various suitable ways in which storage device (163) may be used will be apparent to those of ordinary skill in the art in view of the teachings herein. Similarly, various suitable forms that storage device (163) may take will be apparent to those of ordinary skill in the art in view of the teachings herein.

Battery pack (164) is configured to provide operational power to communication hub platform device (100). By way of example only, battery pack (164) may comprise one or more lithium ion battery cells. As noted above, battery pack (164) is rechargeable via port (192). Processing module (162) may be configured to execute one or more smart charging algorithms in order to provide regulated recharging of battery pack (164) through known techniques. Processing module (162) may also be configured to execute an algorithm to monitor the charge in battery pack (164). Pursuant to this algorithm, processing module (162) may provide real-time feedback regarding the charge level of battery pack (164) via display screen (134). In addition or in the alternative, processing module (162) may provide a low battery alert via display screen (134) and/or via some audio output device when the charge level of battery pack (164) falls below a certain level. Other suitable forms that battery back (164) may take, as well as other ways in which processing module (162) may interact with battery pack (164), will be apparent to those of ordinary skill in the art in view of the teachings herein.

As noted above, processing module (162) is in communication with light emitting features (136) and display screen (134). Processing module (162) stores and/or executes user settings, communication hub platform device (100) configurations, etc., and orchestrates communications between communication hub platform device (100), a mobile computing device on surface (122), display screen (134), light emitting features (136), and other peripherals.

NFC module (165) and BLE communication module (166) are configured to provide wireless communication with other devices using known components and techniques. By way of example only, when an operator places a conventional tablet device, smartphone device, or similar device on upwardly presented surface (122), processing module (162) may establish bi-directional wireless communication with that tablet device or smartphone device, etc. via NFC module (165) or BLE communication module (166). Similarly, when an operator places a conventional mobile computer on upwardly presented surface (122), processing module (162) may establish bi-directional wireless communication with that mobile computer via NFC module (165) or BLE communication module (166). In addition or in the alternative, processing module (162) may establish bi-directional wireless communication with other kinds of equipment via NFC module (165) or BLE communication module (166). For instance, processing module (162) may establish bi-directional wireless communication with other kinds of equipment that are placed on upwardly presented surface (122). Moreover, processing module (162) may establish bi-directional wireless communication with equipment that is located within the same examination room (but not necessarily placed on upwardly presented surface (122)). Such other equipment may include, among other things, an examination table, equipment used to measure biological data associated with a patient, a computing device providing read/write access to a patient's electronic medical record (EMR), cabinets containing medicine and/or other medical equipment, etc. Further examples of such communication will be described in greater detail below, while still other examples will be apparent to those of ordinary skill in the art in view of the teachings herein.

It should also be understood that NFC module (165) and BLE communication module (166) are merely illustrative examples. In some alternative versions, communication hub platform device (100) only has one module (165, 166) and not the other module (165, 166). In addition or in the alternative, any other suitable kind(s) of wireless communication technologies may be incorporated into communication hub platform device (100).

NIBPM module (167) of the present example comprises a set of components that are operable to obtain NIBPMs via a cuff assembly that is coupled with port (182). By way of example only, NIBPM module (167) may comprise an air pump, one or more valves, one or more pressure sensors, fluid conduits, and/or any other component(s) that may be used to provide NIBPMs. By way of example only, NIBPM module (167) may be constructed and operable in accordance with at least some of the teachings of U.S. Provisional Pat. App. No. 62/110,704, entitled "System and Method for Non-Invasive Blood Pressure Measurement," filed Feb. 2, 2015, the disclosure of which is incorporated by reference herein. Other suitable ways in which NIBPM module (167) may be configured and operable will be apparent to those of ordinary skill in the art in view of the teachings herein. It should also be understood that processing module (162) may be operable to selectively activate NIBPM module (167) in accordance with operator input. In addition, processing module (162) may process NIBPMs and/or other data obtained through NIBPM module (167) and transmit such information to storage device (163) and/or to a remote device.

The foregoing examples of internal components (160) are merely illustrative examples. It should be understood that communication hub platform device (100) may include a variety of other internal components (160) in addition to or in lieu of those described above. Various other suitable kinds of internal components (160) that may be incorporated into communication hub platform device (100) will be apparent to those of ordinary skill in the art in view of the teachings herein.

C. Exemplary Tabletop Accessories

In some instances, an operator may wish reduce the risk of having items inadvertently slide or roll off of upwardly presented surface (122). FIGS. 16A-18 show an exemplary tray (200) that may be secured to communication hub platform device (100) to reduce this risk. Tray (200) of the present example comprises an upwardly presented surface (202) that is bounded by a proximal lip portion (204), a distal lip portion (206), and a pair of side lip portions (208). Lip portions (204, 206, 208) extend upwardly from and around upwardly presented surface (202), thereby providing structural barriers to assist in retaining items on upwardly presented surface (202). Side lip portions (208) include gaps (209) that are configured to provide clearance for cables extending laterally from devices placed on upwardly presented surface (202).

Figure 16A:
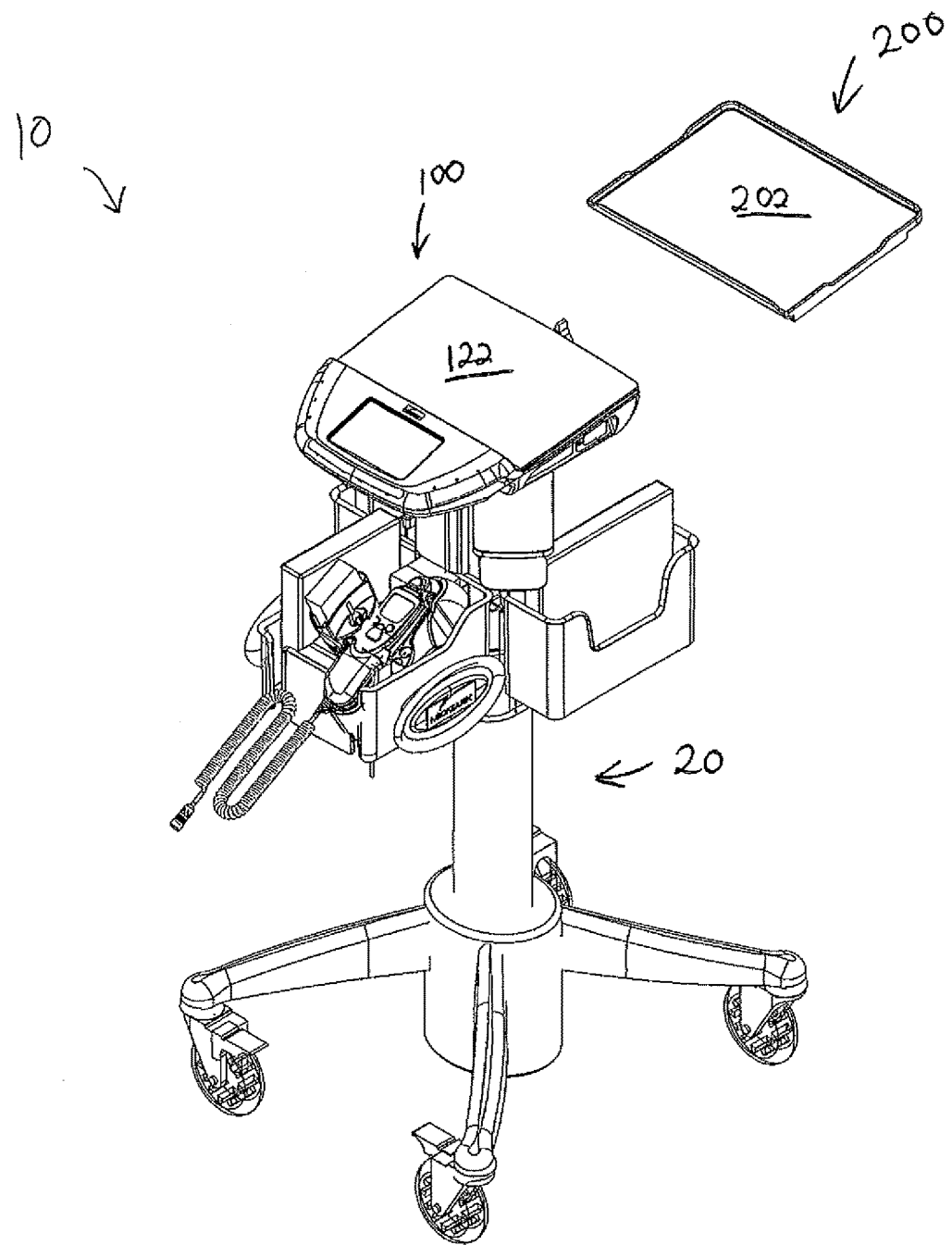
FIG. 16A depicts a perspective view of the communication hub assembly of FIG. 1, with a first exemplary add-on tabletop separated from the communication hub platform device of FIG. 6.
Figure 16B:
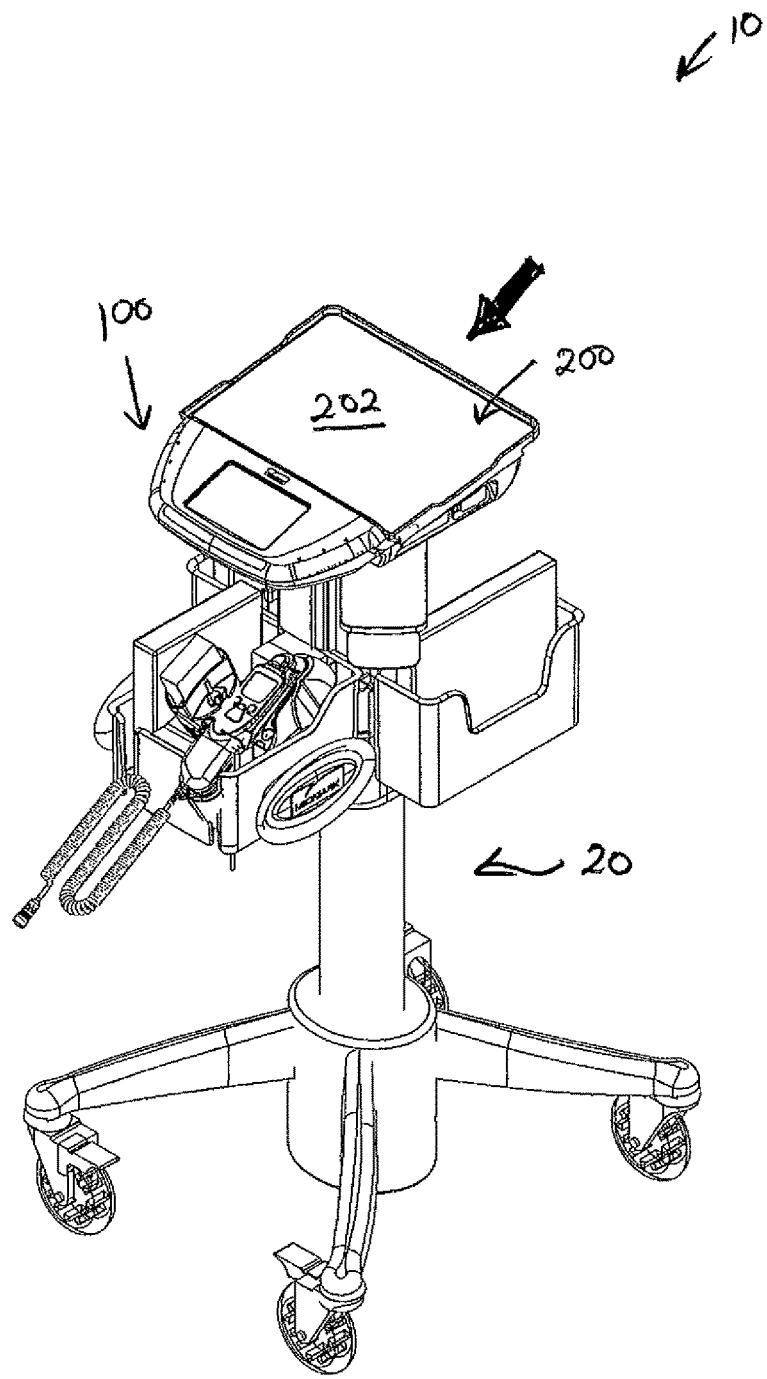
FIG. 16B depicts a perspective view of the communication hub assembly of FIG. 1, with the first exemplary add-on tabletop of FIG. 16A secured to the communication hub platform device of FIG. 6.
Figure 17:
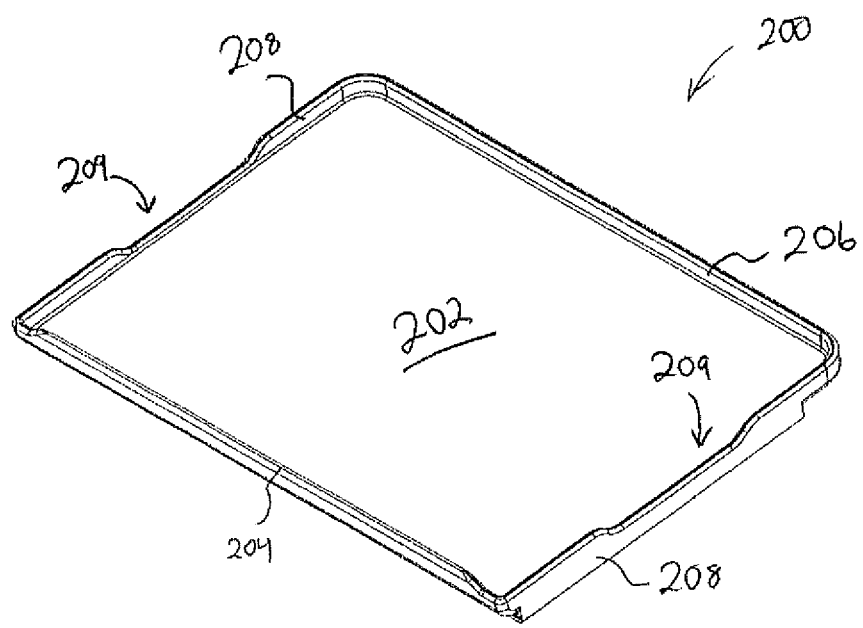
FIG. 17 depicts a perspective view of the first exemplary add-on tabletop of FIG. 16A.
Figure 18:
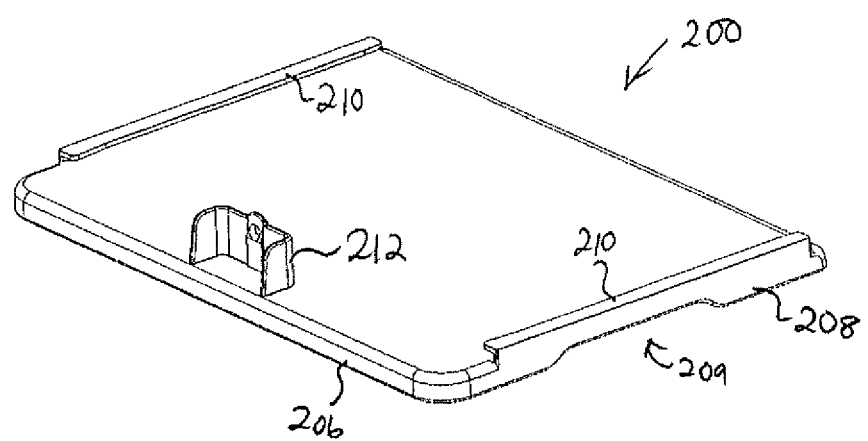
FIG. 18 depicts another perspective view of the first exemplary add-on tabletop of FIG. 16A.

As best seen in FIG. 18, the underside of tray (200) includes a pair of rails (210) and a boss member (212). Rails (210) are configured to slidably fit in mounting channels (130) to provide engagement between tray (200) and lateral edges (124) of upper housing (120). Boss member (212) is configured to engage distal edge (126) of upper housing (120). Of course, any other suitable structures may be used to provide engagement between tray (200) and communication hub platform device (100). It should be understood from the foregoing that tray (200) may be removably secured to communication hub platform device (100) as shown in FIGS. 16A-16B. It should also be understood that NFC module (165) and BLE communication module (166) may communicate with a device placed on upwardly presented surface (202) just as well as such modules (165, 166) would communicate with the same device if it were placed directly on upwardly presented surface (122).

FIGS. 19A-21 show another exemplary tray (250) that may be secured to communication hub platform device (100). Tray (250) of this example is substantially identical to tray (250), except that tray (250) is larger to accommodate more items or larger items. Tray (250) of the present example comprises an upwardly presented surface (252) that is bounded by a proximal lip portion (254), a distal lip portion (256), and a pair of side lip portions (258). Lip portions (254, 256, 258) extend upwardly from and around upwardly presented surface (252), thereby providing structural barriers to assist in retaining items on upwardly presented surface (252). Side lip portions (258) include gaps (259) that are configured to provide clearance for cables extending laterally from devices placed on upwardly presented surface (252).

Figure 19A:
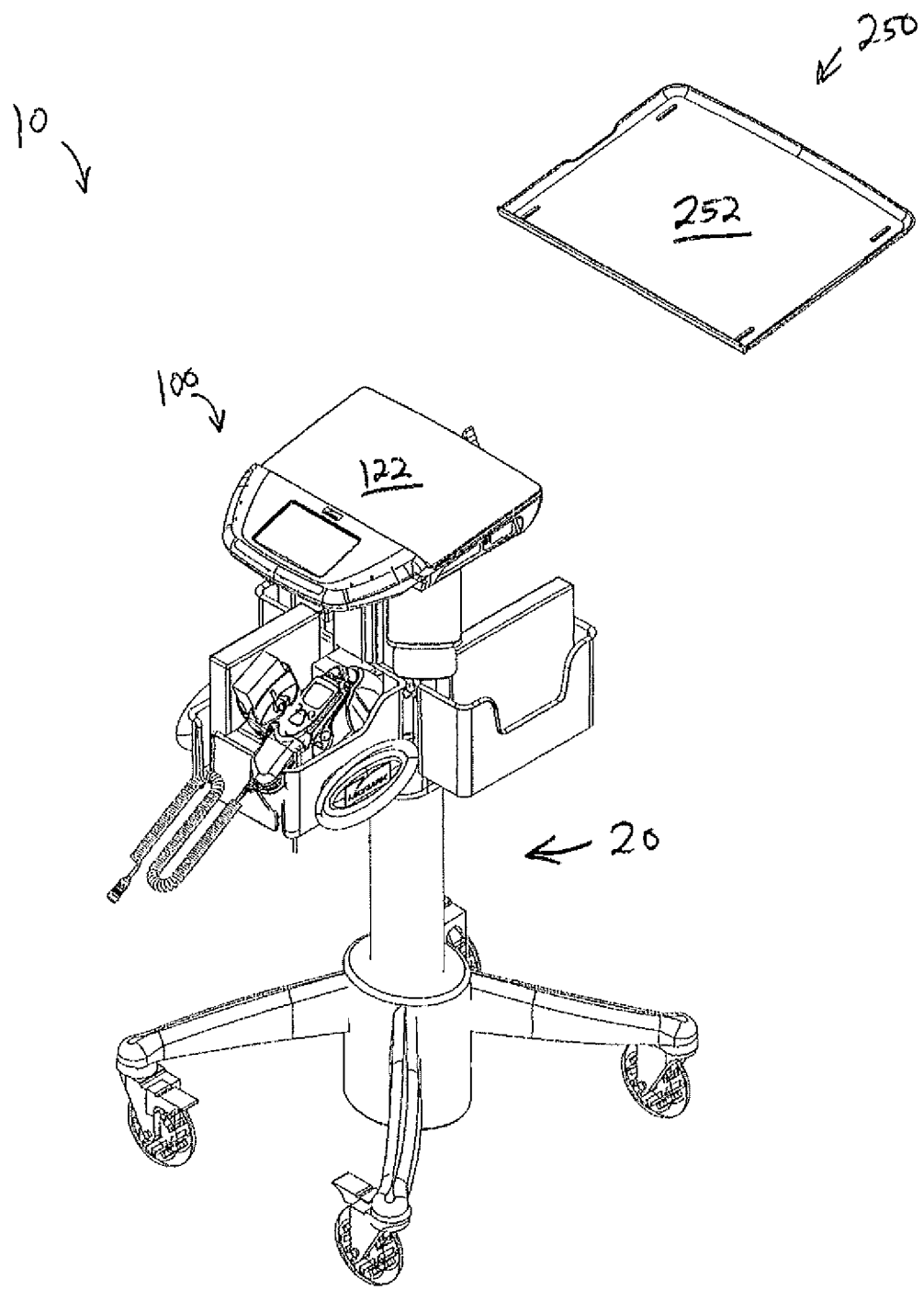
FIG. 19A depicts a perspective view of the communication hub assembly of FIG. 1, with a second exemplary add-on tabletop separated from the communication hub platform device of FIG. 6.
Figure 19B:
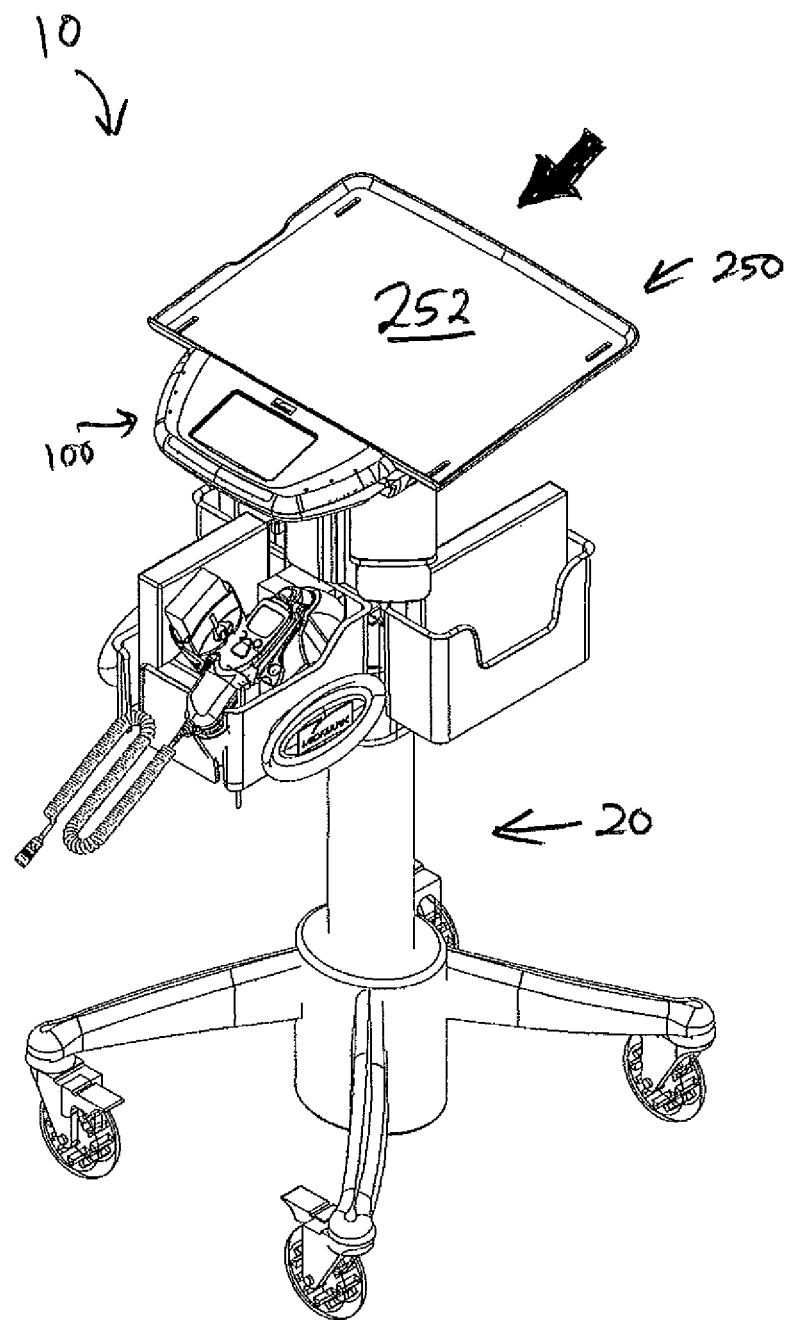
FIG. 19B depicts a perspective view of the communication hub assembly of FIG. 1, with the second exemplary add-on tabletop of FIG. 19A secured to the communication hub platform device of FIG. 6.
Figure 20:
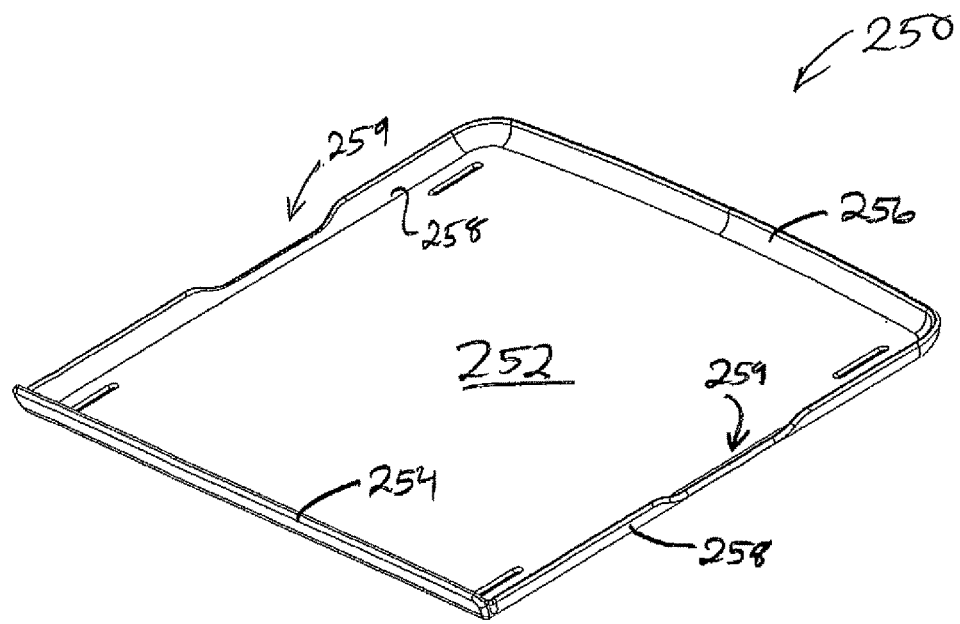
FIG. 20 depicts a perspective view of the first exemplary add-on tabletop of FIG. 19A.
Figure 21:
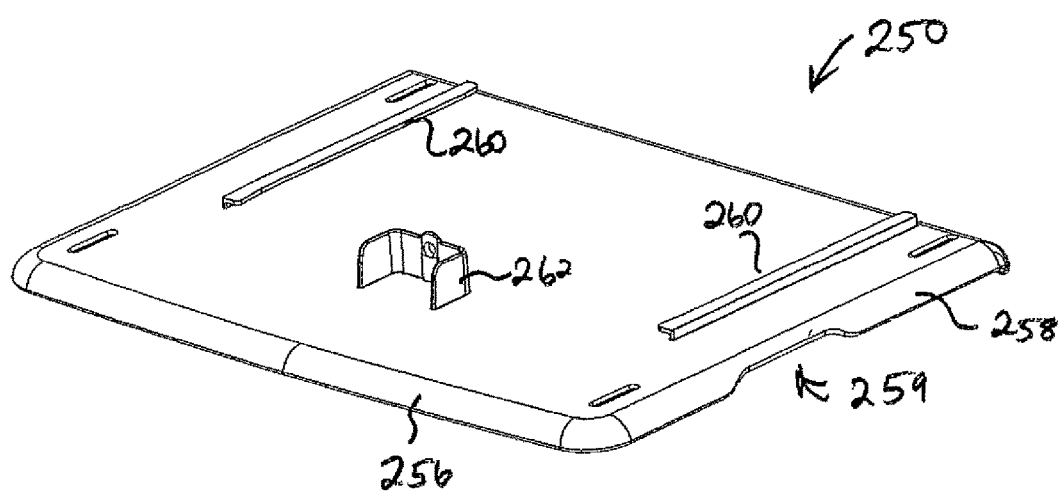
FIG. 21 depicts another perspective view of the first exemplary add-on tabletop of FIG. 19A.

As best seen in FIG. 21, the underside of tray (250) includes a pair of rails (260) and a boss member (262). Rails (260) are configured to slidably fit in mounting channels (130) to provide engagement between tray (250) and lateral edges (124) of upper housing (120). Boss member (262) is configured to engage distal edge (126) of upper housing (120). Of course, any other suitable structures may be used to provide engagement between tray (250) and communication hub platform device (100). It should be understood from the foregoing that tray (250) may be removably secured to communication hub platform device (100) as shown in FIGS. 19A-19B. It should also be understood that NFC module (165) and BLE communication module (166) may communicate with a device placed on upwardly presented surface (202) just as well as such modules (165, 166) would communicate with the same device if it were placed directly on upwardly presented surface (122).

Of course, trays (200, 250) are just merely illustrative examples of accessories that may be secured to communication hub platform device (100). Other suitable accessories will be apparent to those of ordinary skill in the art in view of the teachings herein. Alternatively, communication hub platform device (100) may be used without accessories secured thereto.

D. Exemplary Alternative Mounting Structures

Figure 22:
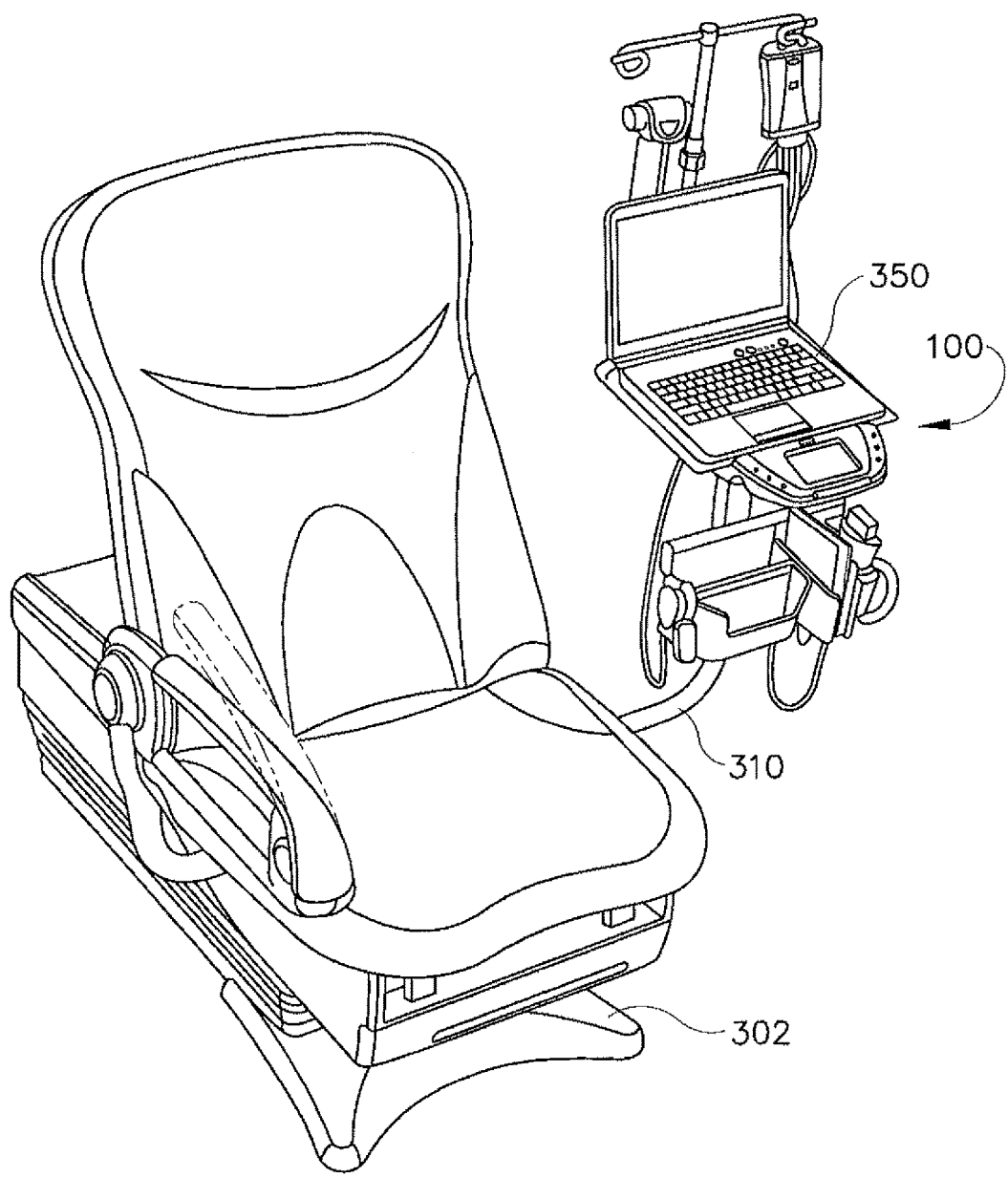
FIG. 22 depicts a perspective view of the communication hub platform device of FIG. 6 secured to an integral arm of an exemplary medical examination table, with a left patient armrest of the table omitted for clarity.

In the example of communication hub assembly (10) described above, communication hub platform device (100) is secured to a cart (20). However, cart (20) is just one example of what communication hub platform device (100) may be secured to. FIG. 22 shows another merely illustrative example of something that communication hub platform device (100) may be secured to. In particular, FIG. 22 shows an exemplary medical examination table (300) with an integral mounting arm (310). While FIG. 22 includes a right patient armrest (304), it should be understood that a left patient armrest (304) is intentionally omitted from FIG. 22 for clarity. As shown in FIGS. 24-29, 31-39, 41-45, 47-52, and 57, medical examination table (300) of the present example in fact includes a left patient armrest (304). Mounting arm (310) extends outwardly and upwardly from a base (302) of medical examination table (300). In some versions, mounting arm (310) is operable to pivot and/or slide relative to base (302). As shown, communication hub platform device (100) is secured to arm (310) and has a conventional mobile computer (350) (e.g., laptop computer, etc.) placed on upwardly presented surface (122). It should therefore be understood that processing module (162) may be in wireless communication with mobile computer (350) via NFC module (165) and/or BLE communication module (166).

It should also be understood that processing module (162) may be in communication with medical examination table (300) via NFC module (165), via BLE communication module (166), via a cable secured to port (184, or in some other fashion. For instance, medical examination table (300) may be configured to determine the weight of a patient that is seated or supine on medical examination table (300). In that regard, medical examination table (300) may be constructed and operable in accordance with at least some of the teachings of U.S. Pub. No. 2013/0247300, entitled "Medical Examination Table with Integrated Scale," published Sep. 26, 2013, the disclosure of which is incorporated by reference herein. Medical examination table (300) may communicate the patient's weight to processing module (162) via NFC module (165), via BLE communication module (166), via a cable secured to port (184), or in some other fashion. Medical examination table (300) and/or other equipment may also be operable to capture a patient's height and communicate the patient's height to processing module (162) via NFC module (165), via BLE communication module (166), via a cable secured to port (184), or in some other fashion.

In addition or in the alternative, processing module (162) may be operable to command medical examination table (300) via NFC module (165), via BLE communication module (166), via a cable secured to port (184), or in some other fashion. For instance, processing module (162) may be operable to command medical examination table (300) to raise and lower the patient relative to the ground, to transition between a folded, upright (seated) configuration and a flat (supine) configuration, etc. Other suitable relationships between communication hub platform device (100) and medical examination table (300) will be apparent to those of ordinary skill in the art in view of the teachings herein.

While cart (20) and integral mounting arm (310) of medical examination table (300) have been provided as examples of structures to which communication hub platform device (100) may be mounted, still other examples of such structures will be apparent to those of ordinary skill in the art in view of the teachings herein. Such alternative structures may be mobile (e.g., like cart (20)) or secured in a fixed location (e.g., like mounting arm (310)). Regardless of the type of structure communication hub platform device (100) is mounted to, some versions may permit communication hub platform device (100) to be removed from such a mounting structure; or may prevent communication hub platform device (100) from being removed from such a mounting structure.

II. Exemplary Electronic Ecosystem through Communication Hub

Figure 57:
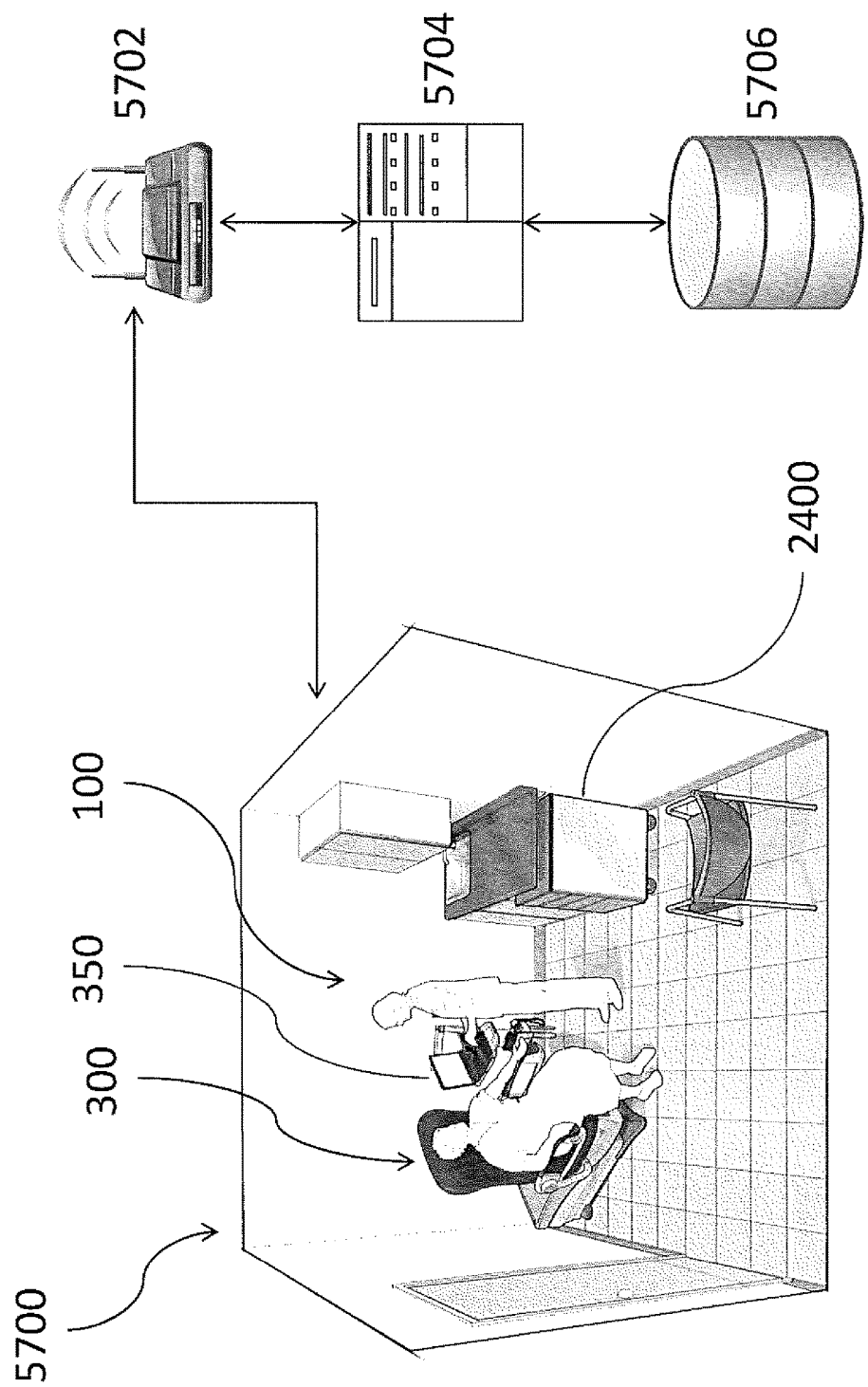
FIG. 57 depicts a diagrammatic view of an exemplary system established between the communication hub assembly of FIG. 1 and remote equipment.

The devices described above may be used as part of an electronic ecosystem of devices to enable various functionalities within configured locations, such as, for example, the exemplary medical examination room (5700) shown in FIG. 57. In examples such as those depicted, one or more devices such as the medical examination table (300), mobile computer (350), hub platform device (100), and storage cabinet (2400) may be communicatively coupled with an ecosystem server (5704) via a network device (5702) such as a wireless network router, etc. Other equipment may be coupled with ecosystem server (5704) via a network device (5702) as well, including but not limited to RFID sensing devices. Such RFID sensing devices may be operable to detect the presence of a hub platform device (100) in each room and/or various other kinds of inventory. In some versions, hub platform device (100) serves as an intermediary or communications hub between network device (5702) and other equipment in the medical examination room, such that all communications to and from such equipment pass through hub platform device (100). In some other versions, one or more pieces of equipment in the medical examination room communicate directly with network device (5702), without necessarily communicating with hub platform device (100). In some such versions, hub platform device (100) is simply omitted. It should also be understood that, while hub platform device (100) is provided as a stand-alone piece of equipment in this example, any of the functionality of hub platform device (100) may be integrated into some other piece of equipment or pieces of equipment in the medical examination room (e.g., a medical examination table (300), etc.).

The storage cabinet (2400) may comprise a storage container having a door, drawer, and/or lid, etc. that can be opened to access the contents, as well as a locking mechanism for locking the door, drawer, and/or lid, etc. in a closed position and preventing access to the contents. The locking mechanism may be enabled to prevent access to the contents of the cabinet (2400) or disabled to allow access to the contents of the cabinet (2400). In some instances, the cabinet (2400) is configured to store medicine and includes at least two independent locking devices, both of which must be unlocked in order to gain access to the contents of cabinet (2400). The storage cabinet (2400) may also have a wireless or wired communication device such as a network card, wireless card, or electrical switch that may receive a signal from an external source and cause the locking mechanism (or locking mechanisms) to actuate. Actuation of the locking mechanism may be performed based upon communication received from the ecosystem server (5704) or another device. It should also be understood that ecosystem server (5704) may be operable to provide a lockout of controls of examination table (300). For instance, such examination table (300) controls may be locked out whenever storage cabinet (2400) is in a locked state. The examination table (300) controls may be unlocked when storage cabinet (2400) is unlocked and/or at any other suitable time.

Some versions of the cabinet (2400) may also include temperature control features. For instance, such temperature control features may be provided when the cabinet (2400) is used to store temperature sensitive medications. Such temperature control features may include a temperature sensor and a feature that is operable to adjust the temperature within the cabinet (2400). These temperature control features may be in communication with the ecosystem server (5704). For instance, the ecosystem server (5704) may receive data from the temperature sensor and provide one or more automated responses when the sensed temperature exceeds a threshold or falls below a threshold. In some such versions, the ecosystem server (5704) activates a temperature control feature within the cabinet (2400) to adjust the temperature to bring the temperature back within an acceptable range. As another merely illustrative example, the ecosystem server (5704) may adjust a thermostat that is external to the cabinet (2400) yet is operable to affect the temperature within cabinet (2400) (e.g., by adjusting the temperature of the room in which the cabinet (2400) is located). As yet another merely illustrative example, the ecosystem server (5704) may send an automated alert (e.g., via email, text message, automated telephone call, etc.) to the appropriate personnel so such personnel may react appropriately to correct the temperature of the cabinet (2400). Other suitable ways in which ecosystem server (5704) may be provided with temperature sensitivity and responsiveness will be apparent to those of ordinary skill in the art in view of the teachings herein.

The ecosystem server (5704) may further be communicatively coupled with a database (5706). The database (5706) may comprise one or more relational databases or other database type, flat file databases, distributed databases, virtual databases, physical disks, or other storage types that would allow for the storage and organization of data. The ecosystem server (5704) may comprise one or more physical computers, virtual computers, distributed computers, or other computing devices that allow for the manipulation, analysis, and communication of data. The network device (5702) may comprise one or more network hubs, routers, switches, computers, or other devices that can facilitate the receipt and communication of data across a network of multiple devices. The network device (5702), ecosystem server (5704) and database (5706) could be separate devices in some versions; but in other versions the functionalities of two or more of the devices (5702, 5704, 5706) could be embodied in a single device. For instance, in some versions, the functionality of one or more of these devices (5702, 5704, 5706) may be fully integrated into communication hub platform device (100).

The network device (5702) may be communicatively coupled with the examination room devices (100, 300, 350, 2400) via a wireless connection (e.g., Wi-Fi, Bluetooth, radio, infrared, NFC, or other wireless communication type); or via a wired connection (e.g., USB, Ethernet, coaxial, fiber optic, or other wired communication type). In some versions, a combination of wireless and wired communication may also be used. For example, the hub platform device (100) may be connected to the network device (5702) via a wired connection, whereas the medical examination table (300), mobile computer (350), and storage cabinet (2400) may be connected with the network device (5702) via a wireless connection. In further examples, the medical examination table (300), mobile computer (350), and storage cabinet (2400) may be connected via a wired or wireless connection to the hub platform device (100), which may be connected to the network device (5702) via a wired or wireless connection. In this manner, the hub platform device (100) serves as the single point of contact between the medical examination room (5700) and the network device (5702) while allowing communications from the other devices (300, 350, 2400) to pass through the hub platform device (100) to the network device (5702). A variety of communication configurations are possible and may be desirable depending upon the environment and purpose for a particular installation. Various suitable configurations and arrangements will be apparent to those of ordinary skill in the art in view of the teachings herein.

Figure 23:
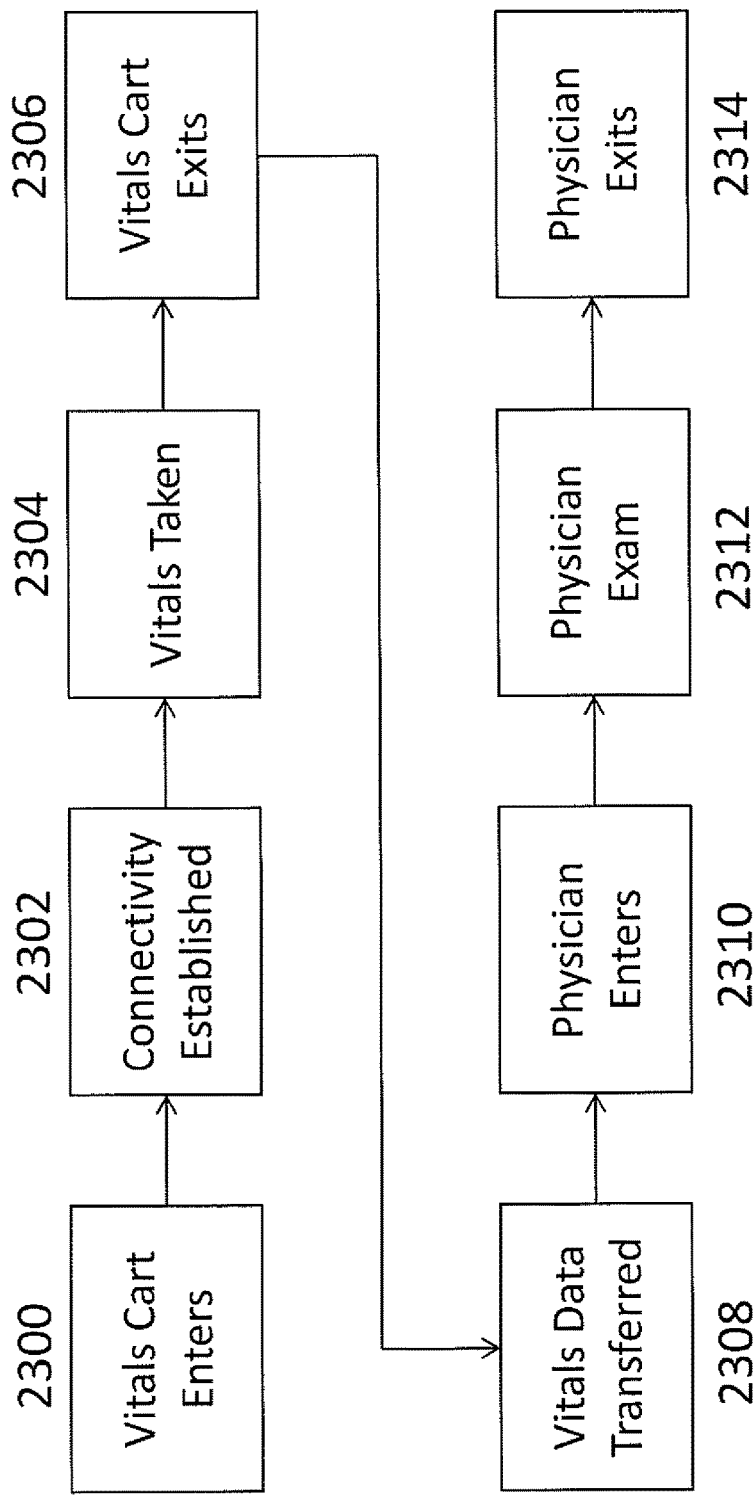
FIG. 23 depicts a flow diagram of an exemplary set of steps that could be performed using the communication hub assembly of FIG. 1.

FIGS. 23-56 show examples of steps that can be performed within a communication hub enabled electronic ecosystem such as that depicted in FIG. 57. It should therefore be understood that all of the below methods and processes may be carried out using the network device (5702), the ecosystem server (5704), and the database (5706) described above. For example, FIGS. 23-29 show an example of steps that could be performed with a hub platform device (100) that is shared across multiple examination rooms. In this example, hub platform device (100) is combined with a cart (20) like communication hub assembly (10) described above. As shown in FIGS. 23 and 25, when the hub platform device (100) enters (2300) the room, ecosystem connectivity is automatically established (2302). In this example, the mobile computer (350) is already placed on and in communication with the hub platform device (100), with each being in communication with the ecosystem server (5706) (containing EMR in this example) via a wireless connection.

Figure 24:
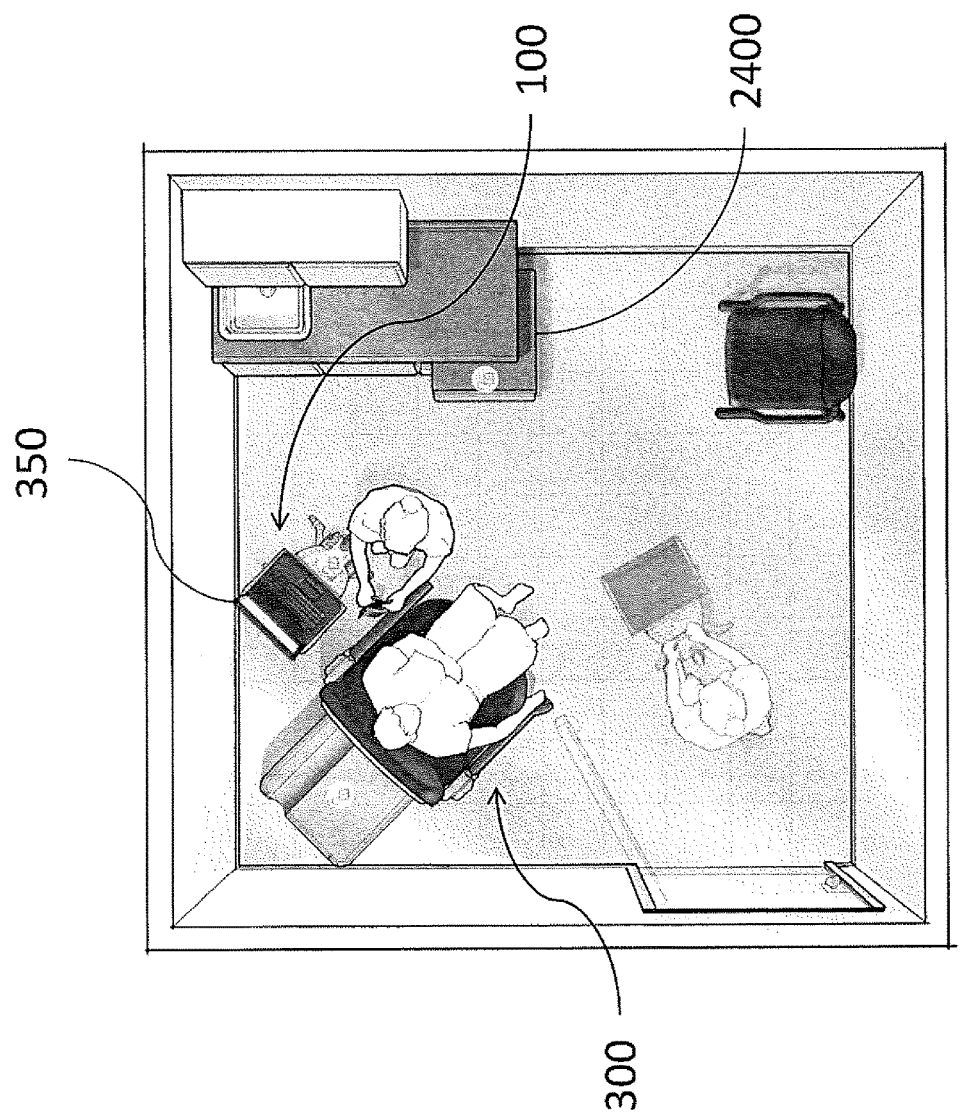
FIG. 24 depicts an overhead diagrammatic view of the communication hub assembly of FIG. 1 located in an examination room where the set of steps of FIG. 23 may be performed.
Figure 25:
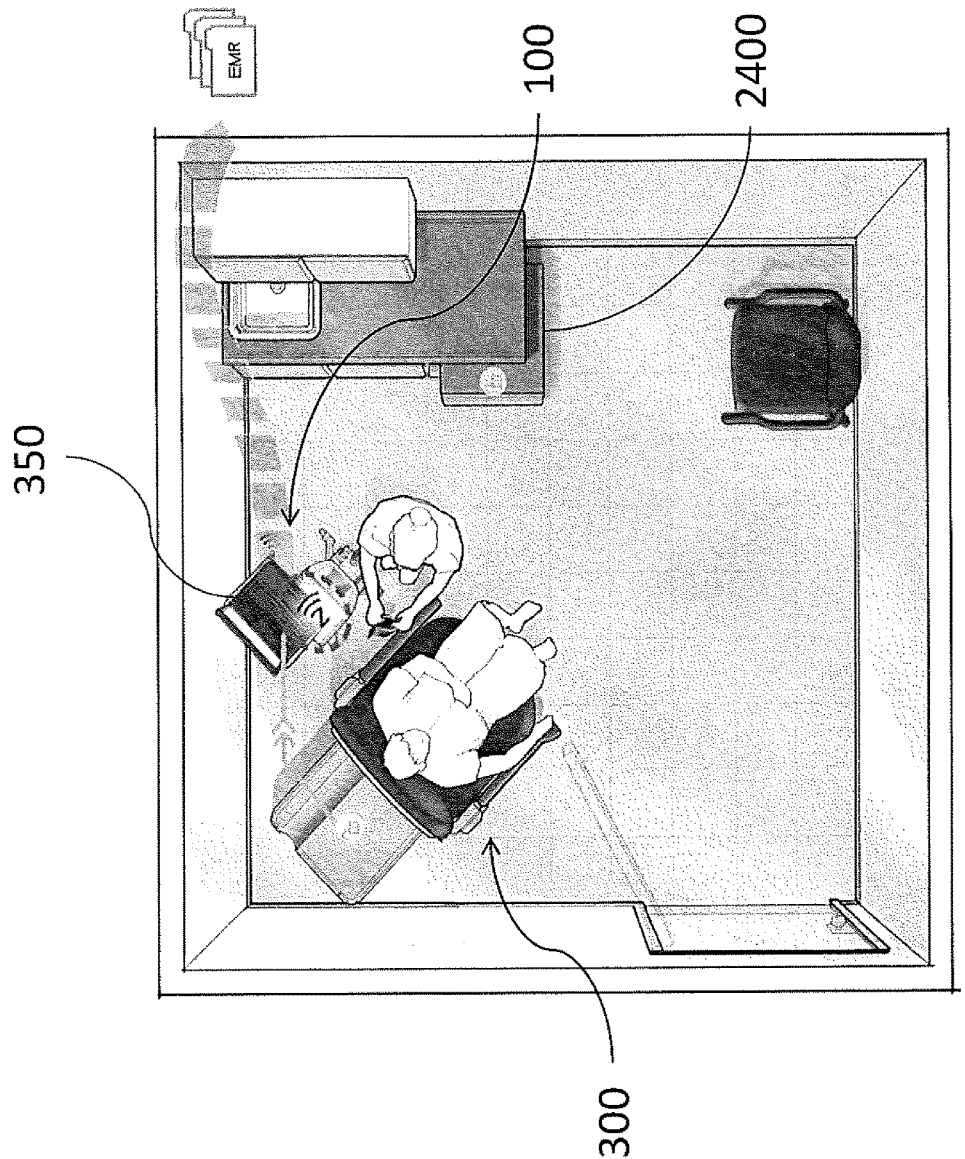
FIG. 25 depicts an overhead diagrammatic view of the communication hub assembly of FIG. 1 located in the examination room of FIG. 24, with a communications link established with an EMR system and in-room equipment.

When the hub platform device (100) enters the room in FIG. 24, connectivity may need to be established (2302) between the hub platform device (100) and other devices available within a specific medical examination room (5700) such as a medical examination table (300). In some examples, connectivity may be established (2302) automatically by a wireless connection between the hub platform device (100) and the medical examination table (300) that is available when they are in close proximity to each other. In other examples, connectivity may be established (2302) semi-manually by a user making a wired connection between the hub platform device (100) and the medical examination table (300) when they are in close proximity to each other, for example, by plugging in a USB or Ethernet cable. Since the hub platform device (100) is shared between multiple rooms in this example, it may not be advantageous for the lock mechanism of storage cabinet (2400) to be enabled or disabled based upon the connectivity or presence of the hub platform device (100). Thus, in this example, the lock mechanism is disabled and allows access at all times. However, in examples where the storage cabinet (2400) contents require a higher level of security, the lock mechanism could be enabled to prevent access when the hub platform device (100) is not present in the same room.

Figure 26:
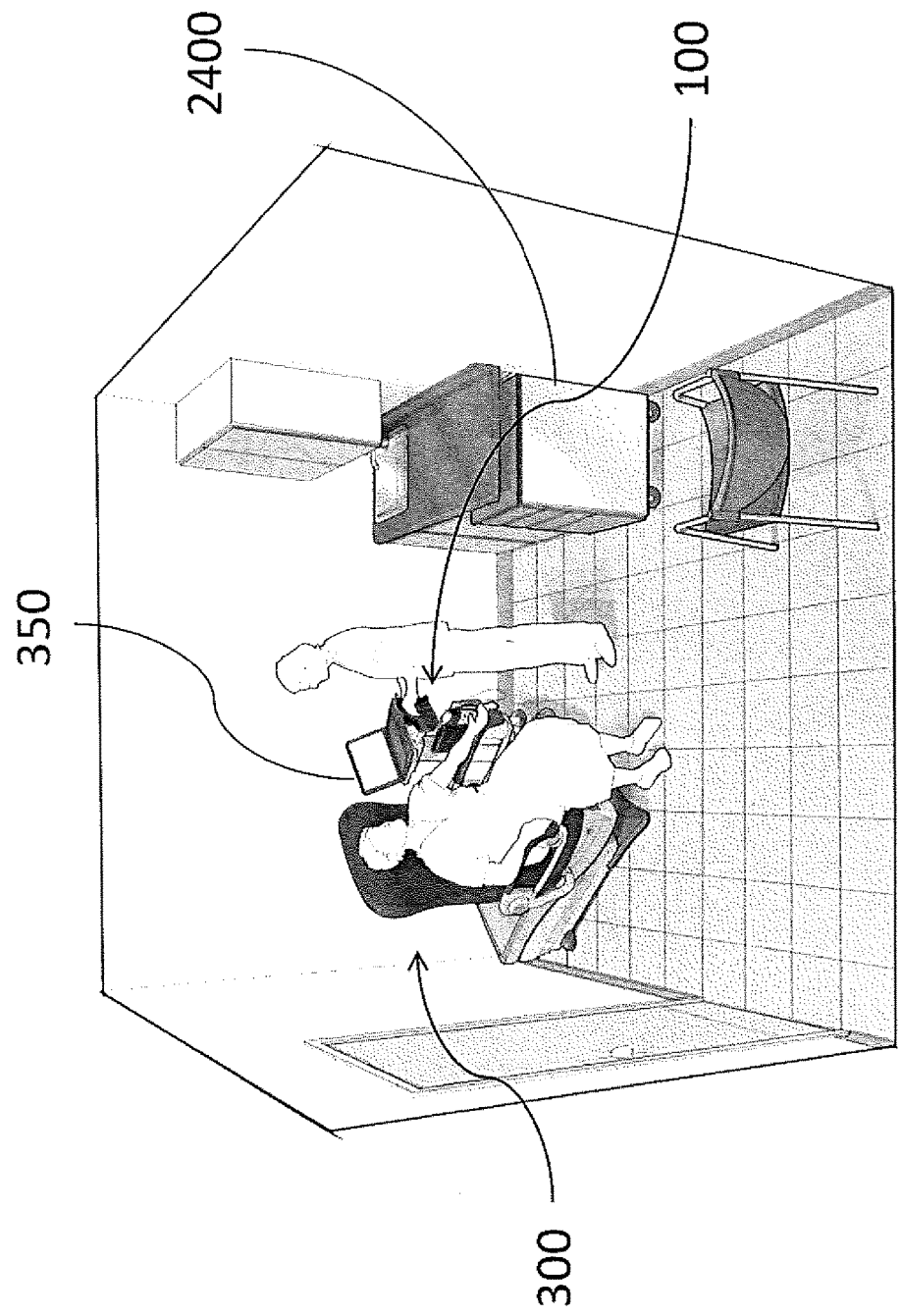
FIG. 26 depicts a perspective view of the communication hub assembly of FIG. 1 located in the examination room of FIG. 24.

As shown in FIGS. 23 and 26, once connectivity is established (2302), a patient's vitals may be taken (2304) using one or more of the ecosystem devices available via the hub platform device (100), such as a digital thermometer (30), a blood pressure measurement device, etc.; and/or using other devices available within the room, such as the medical examination table (300). When connected to the hub platform device (100), room specific devices such as the medical examination table (300) may be interacted with via the hub platform device (100) or mobile computer (350) rather than by directly interacting with the room specific device. For example, when connected with hub platform device (100), the medical examination table (300) could be raised via a control available on the mobile computer (350) rather than by using a foot pedal on the medical examination table (300). As a further example, the medical examination table (300) could be adjusted automatically based upon preferences created during a prior visit for a particular patient and stored on and retrieved from the ecosystem server (5704) during subsequent visits.

Figure 27:
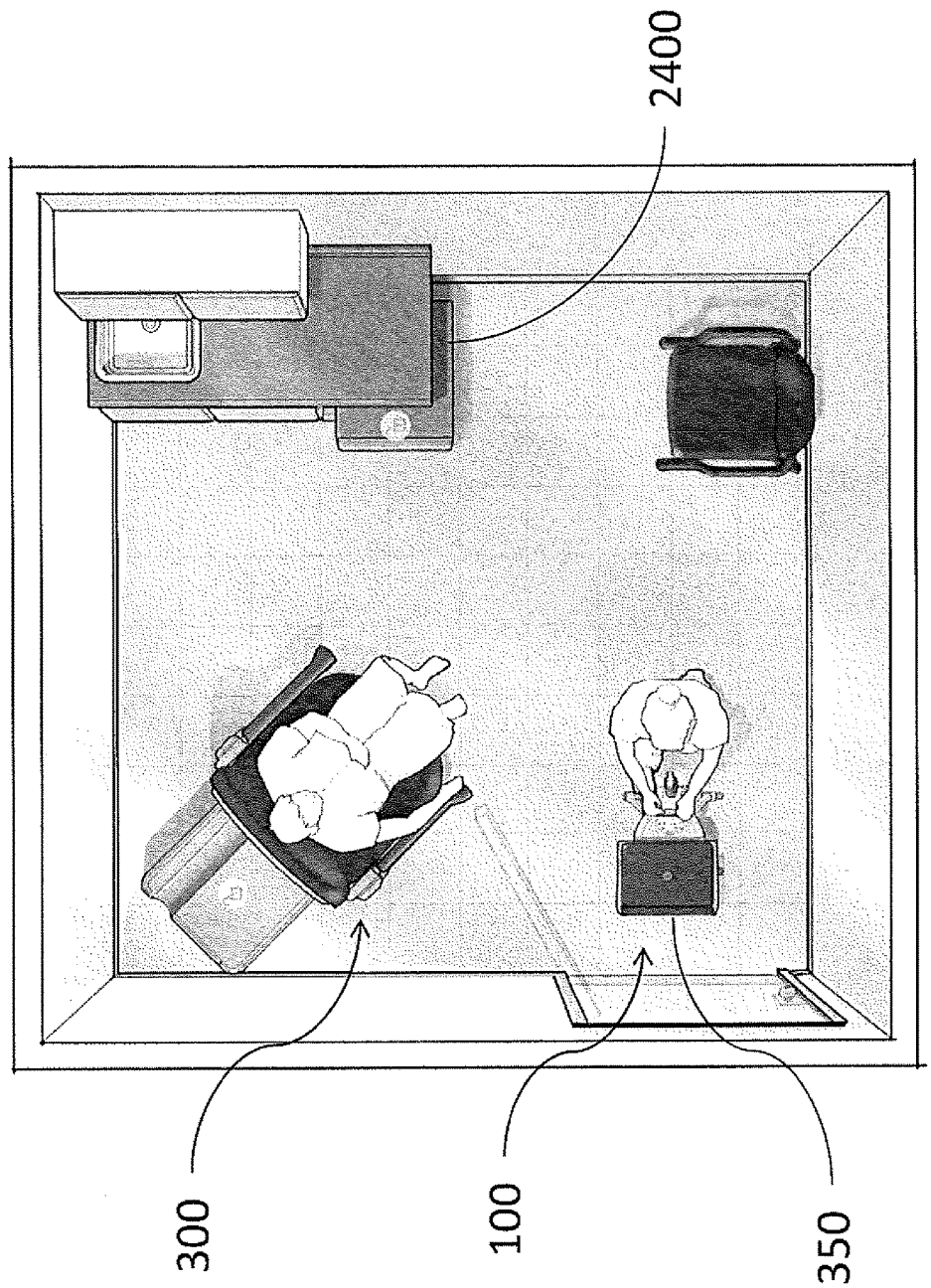
FIG. 27 depicts an overhead diagrammatic view of the communication hub assembly of FIG. 1 leaving the examination room of FIG. 24, with the in-room equipment left in an unlocked state.

As shown in FIGS. 23 and 27, once vitals are taken (2204), the hub platform device (100) may exit the room (2306) and terminate connectivity with devices specific to that room such as the medical examination table (300). For instance, the wireless communication protocol between the platform device (100) and the devices specific to that room may have a relatively short range, such that the platform device (100) leaves that range when (or shortly after) the platform device (100) exits the room (2306). Connectivity may thus be terminated simply by platform device (100) leaving the range of the wireless communication protocol. Alternatively, the room may include one or more proximity sensors (e.g., RFID, EAS, etc.) that are configured to sense entry/exit of platform device (100) into/out of the room. Such sensors may thus provide automated initiation/termination of connectivity between platform device (100) and devices specific to that room based on the sensed presence/absence of platform device (100) in the room. Various other suitable ways in which connectivity may be automatically initiated/terminated based on the presence/absence of platform device (100) in the room will be apparent to those of ordinary skill in the art in view of the teachings herein. It should also be understood that such proximity detection or sensitivity may be readily incorporated into various other examples described herein as will be apparent to those of ordinary skill in the art.

In the example shown, the storage cabinet (2400) remains unlocked at all times regardless of the presence of the hub platform device (100), but in some versions it may advantageous to automatically actuate the lock mechanism of the storage cabinet (2400) when connectivity between the storage cabinet (2400) and the hub platform device (100) ceases, in order to prevent access to the storage cabinet (2400) contents when no medical personnel are present. Other actions could be taken when communication between the hub platform device (100) and room specific devices ceases, for example, automatically updating records kept by the ecosystem server (5704) indicating the physical location of the hub platform device (100), automatically notifying a physician scheduled to visit the medical examination room (5700) that vitals have been completed via a mobile device or other system, or automatically transferring vitals data (2308) or other data to the ecosystem server (5704) so that patient EMR may be created or updated.

Figure 28:
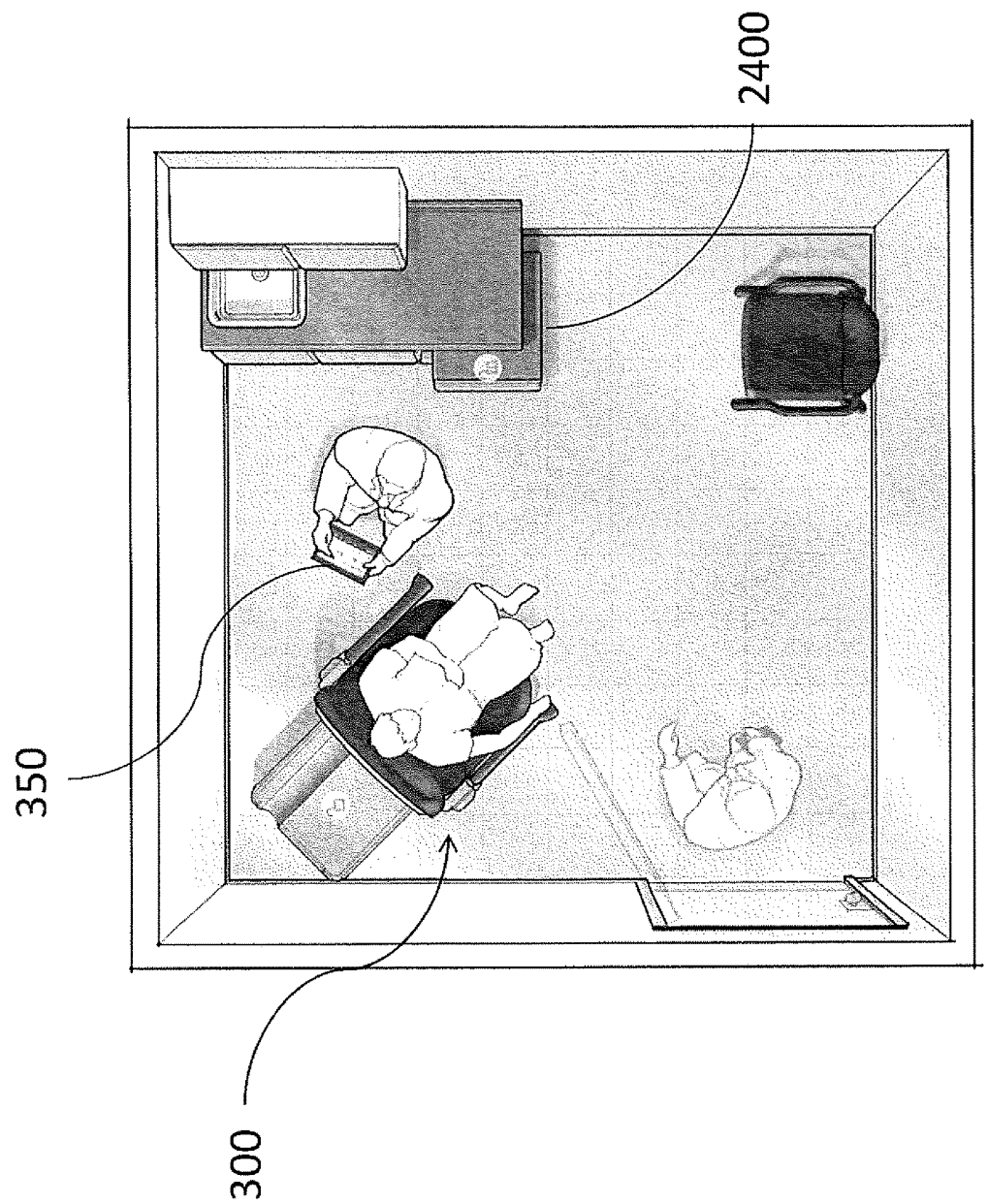
FIG. 28 depicts an overhead diagrammatic view of the examination room of FIG. 24, with a physician entering the examination room while the in-room equipment is in an unlocked state.
Figure 29:
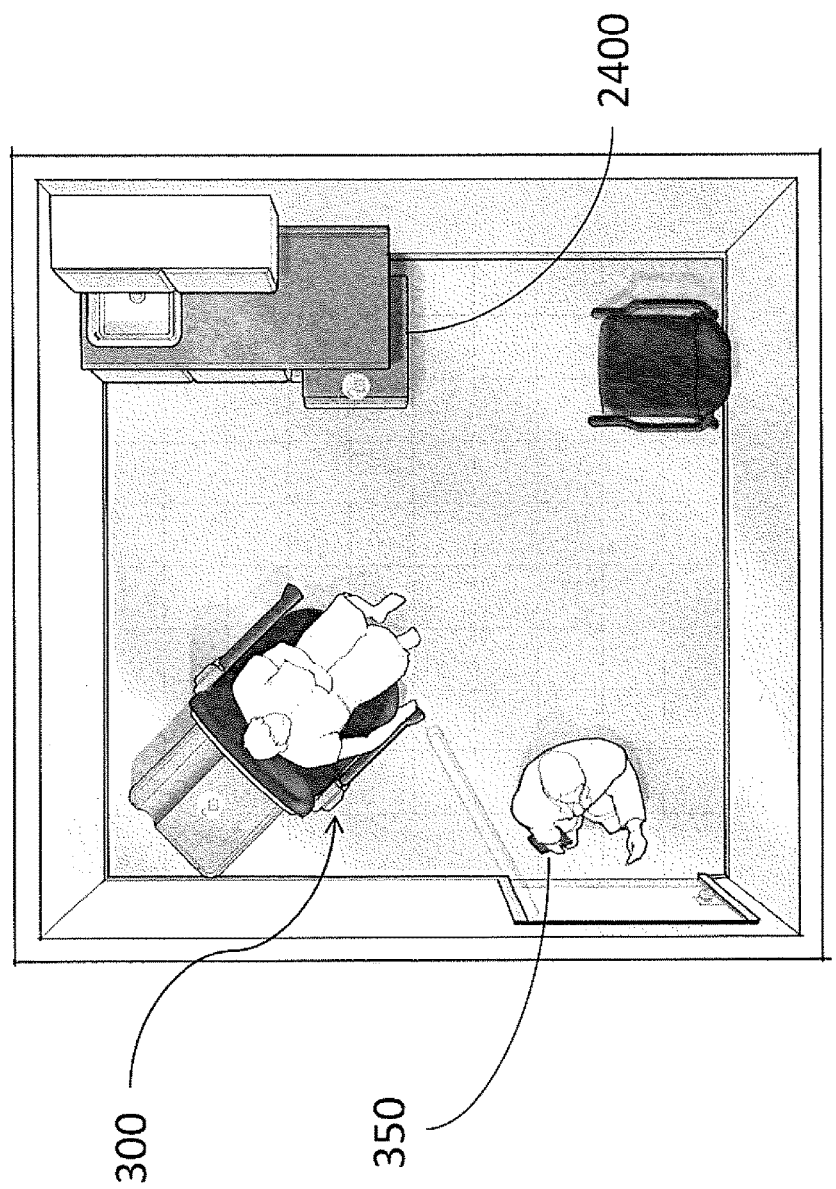
FIG. 29 depicts an overhead diagrammatic view of the examination room of FIG. 24, with the physician of FIG. 28 leaving the examination room while the in-room equipment is in an unlocked state.

As shown in FIGS. 23 and 28, once vitals have been taken (2304) and transferred (2308), a physician may enter the room (2310) and perform an examination (2312). In the present example, the physician may have a mobile computer (350), tablet, smartphone, or other mobile computing device, but would not have a hub platform device (100), meaning that any interaction with the medical examination table (300) or other room specific devices would be direct and manual. Once the physician examination (2312) is complete, the physician exits the room (2314) as shown in FIGS. 23 and 29. Since the physician does not have a hub platform device (100) in this example, no special ecosystem functionality is performed, but neither does the system hamper the physician in his or her normal duties. While FIG. 29 shows storage cabinet (2400) in an unlocked state at this stage, it should be understood that storage cabinet (2400) may alternatively be locked at this stage. For instance, as noted above, the lock mechanism of the storage cabinet (2400) may be automatically actuated to lock the storage cabinet (2400) when connectivity between the storage cabinet (2400) and the communication hub platform device (100) ceases as the communication hub platform device (100) exits the room.

Figure 34:
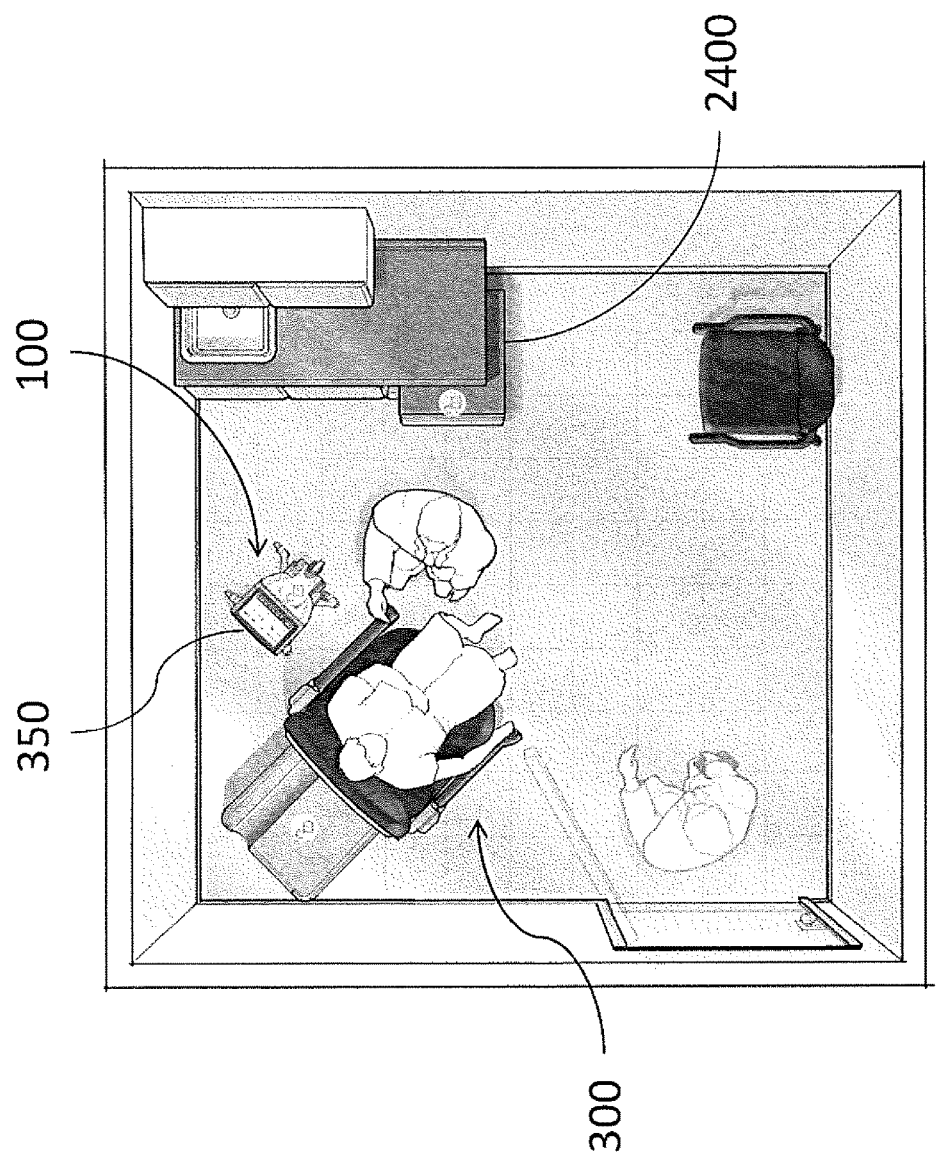
FIG. 34 depicts an overhead diagrammatic view of a physician in the examination room of FIG. 31, with the communication hub assembly of FIG. 1 and the in-room equipment in an unlocked state.
Figure 35:
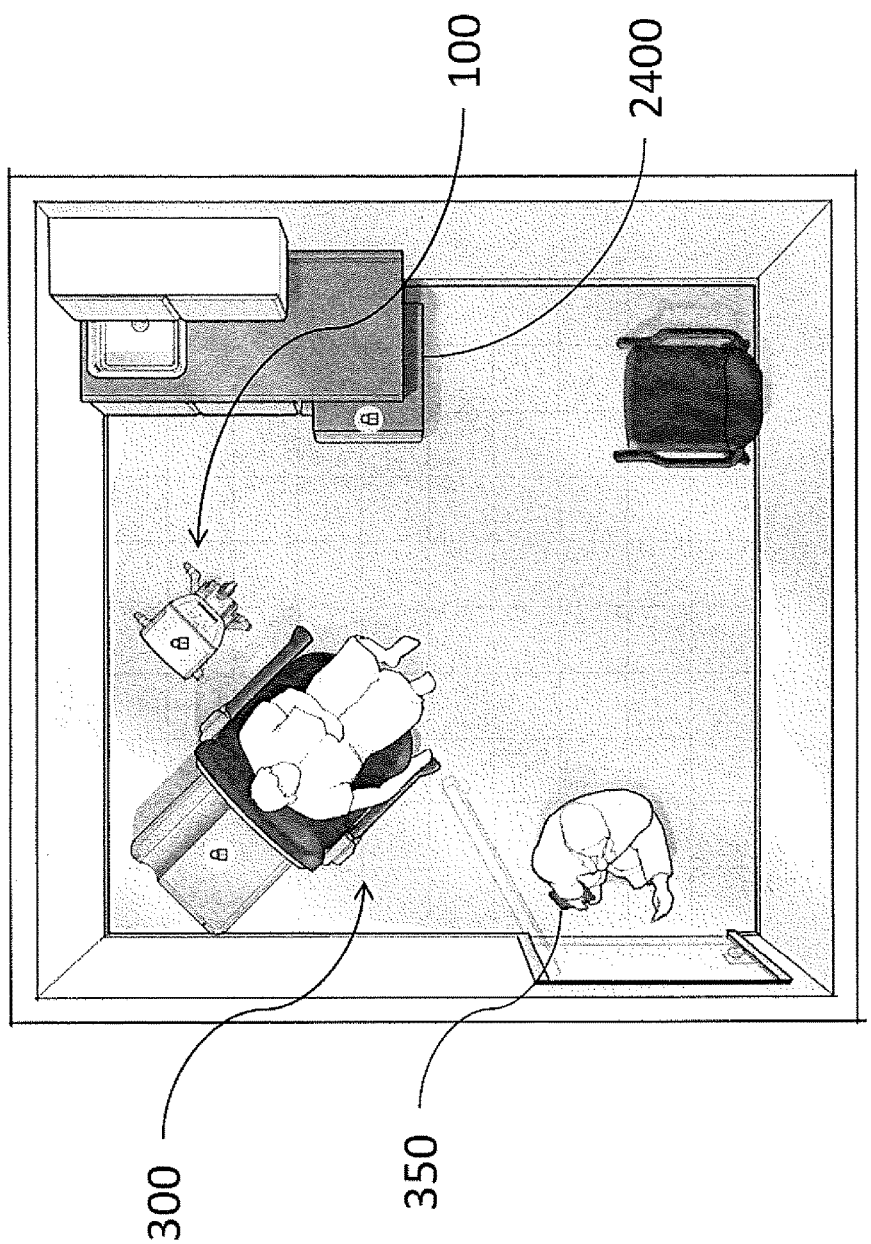
FIG. 35 depicts an overhead diagrammatic view of the physician leaving the communication hub assembly of FIG. 1 in the examination room of FIG. 31, with the communication hub assembly of FIG. 1 and the in-room equipment in a locked state.
Figure 36:
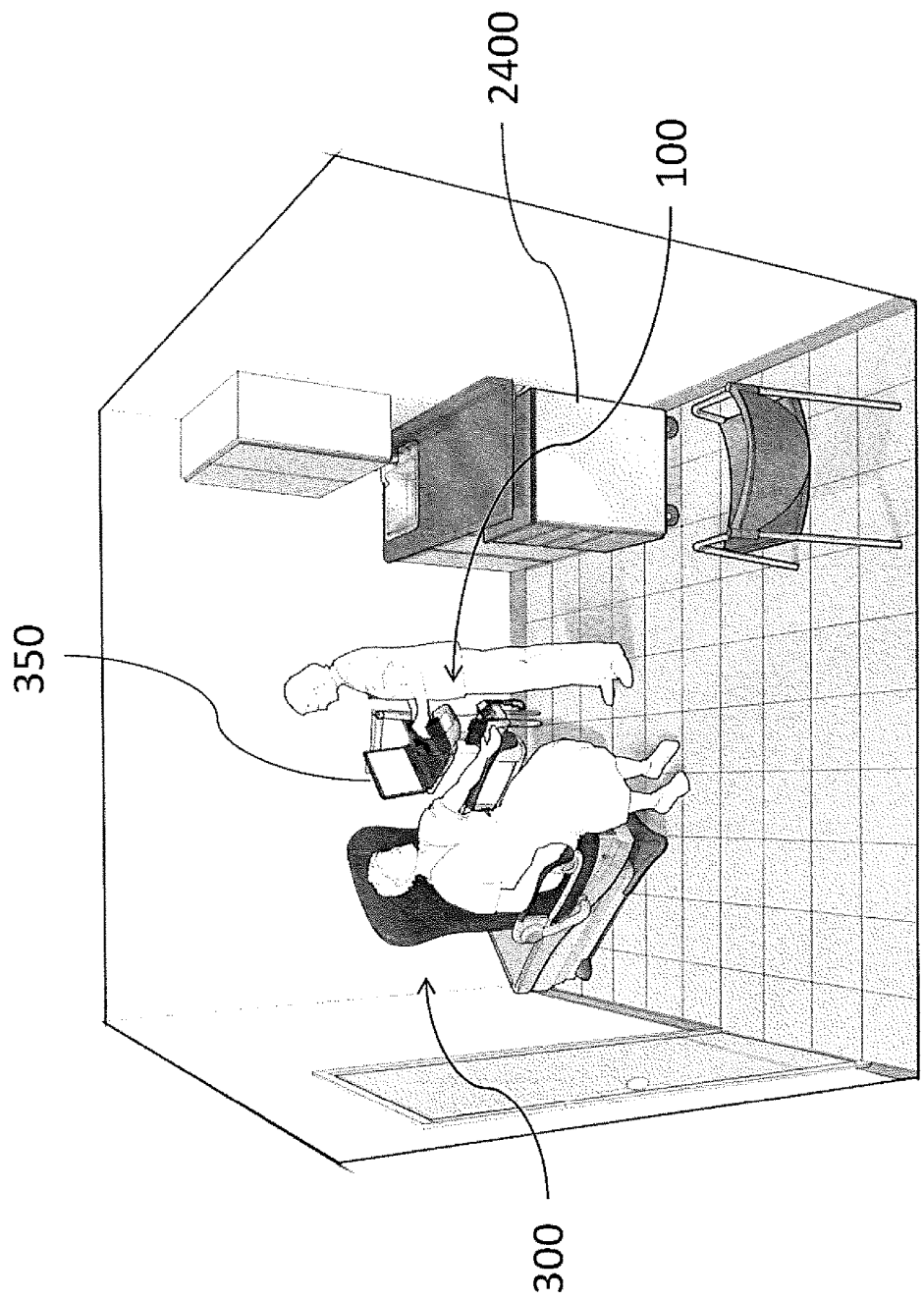
FIG. 36 depicts a perspective view of an alternative examination room with a mounted version of the communication hub assembly of FIG. 1.
Figure 37:
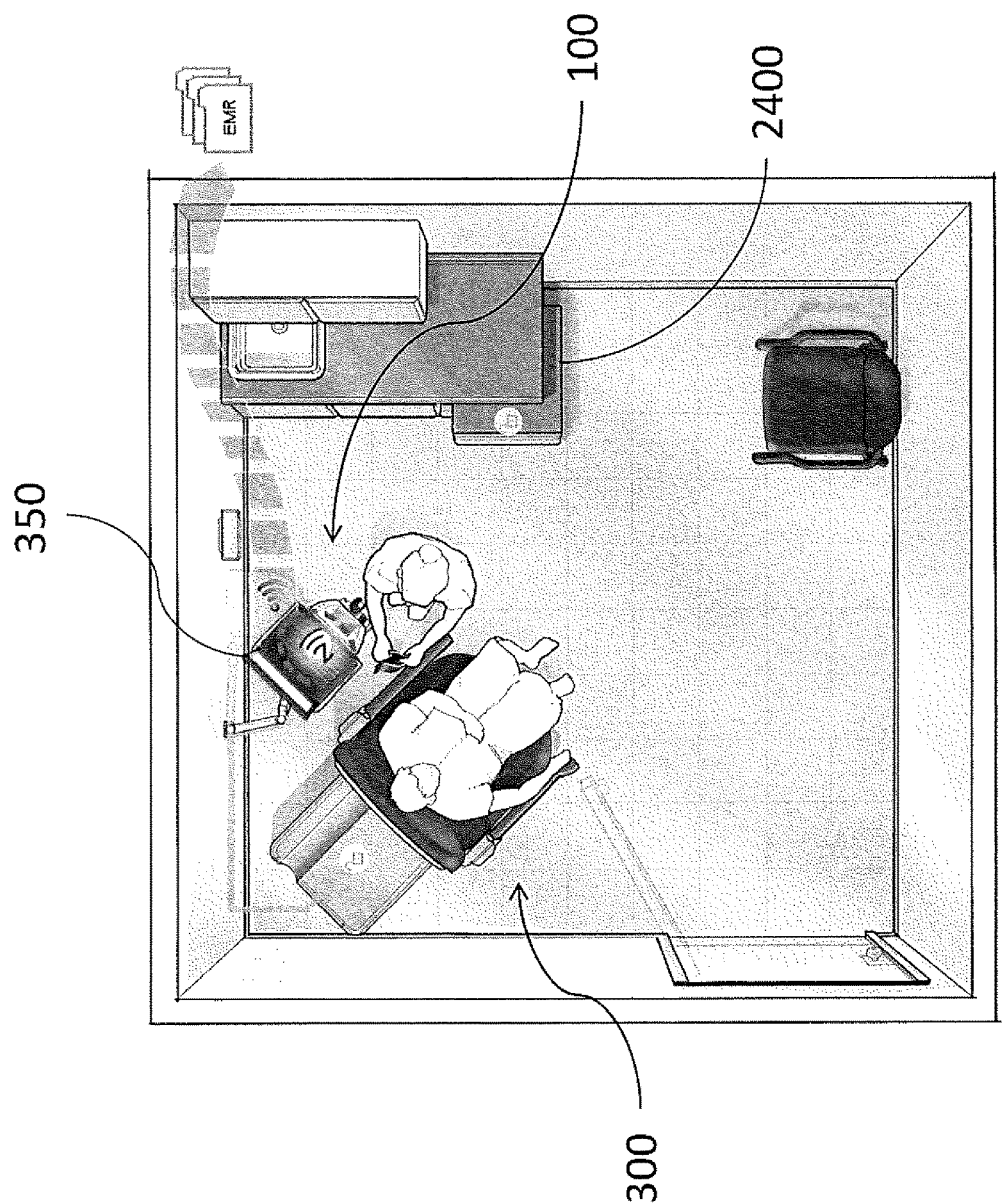
FIG. 37 depicts an overhead diagrammatic view of the communication hub assembly of FIG. 1 mounted in the examination room of FIG. 36, with a communications link established with an EMR system and in-room equipment, and with equipment in the examination room in an unlocked state.
Figure 38:
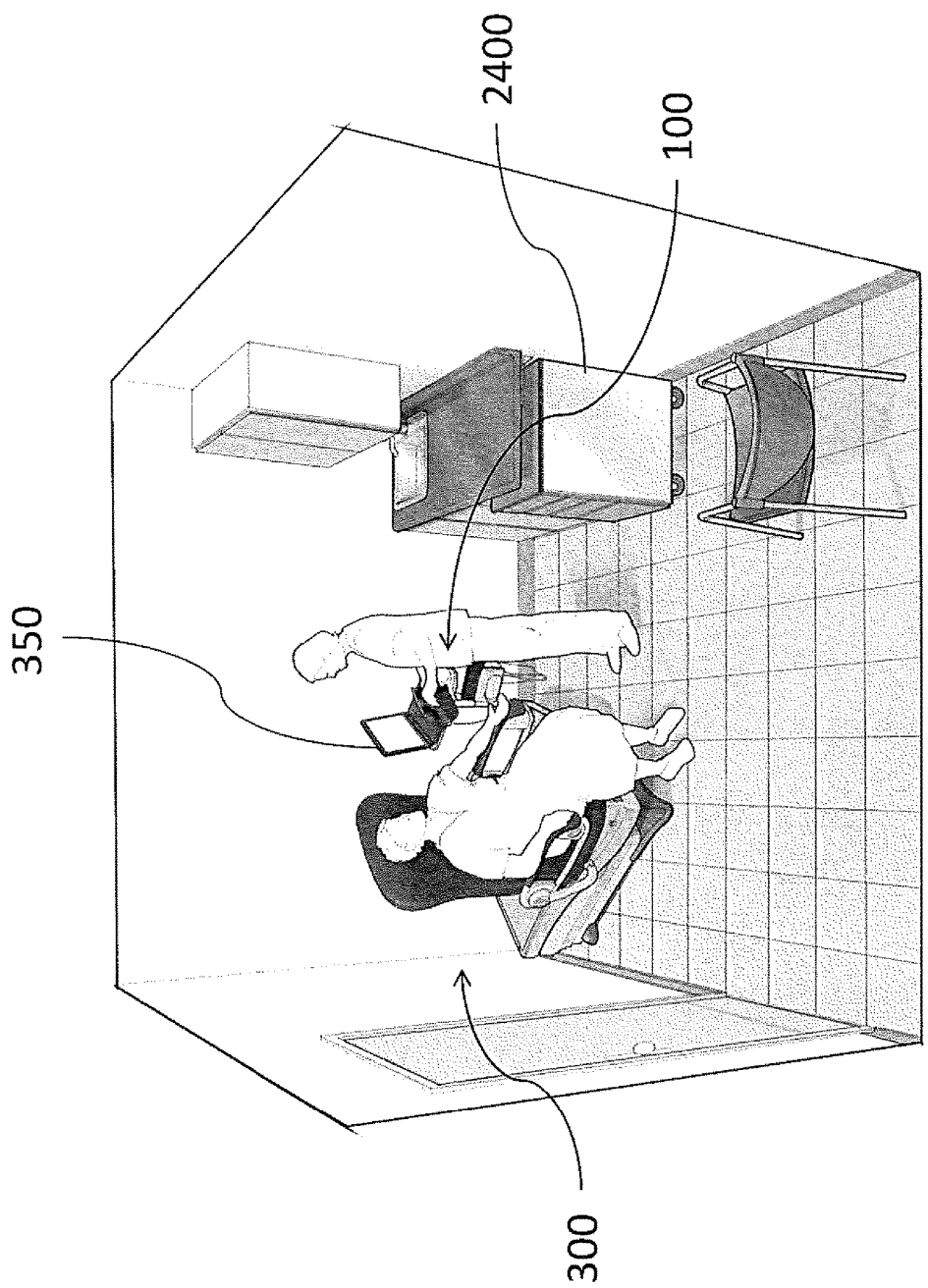
FIG. 38 depicts a perspective view of an alternative examination room with another mounted version of the communication hub assembly of FIG. 1.
Figure 39:
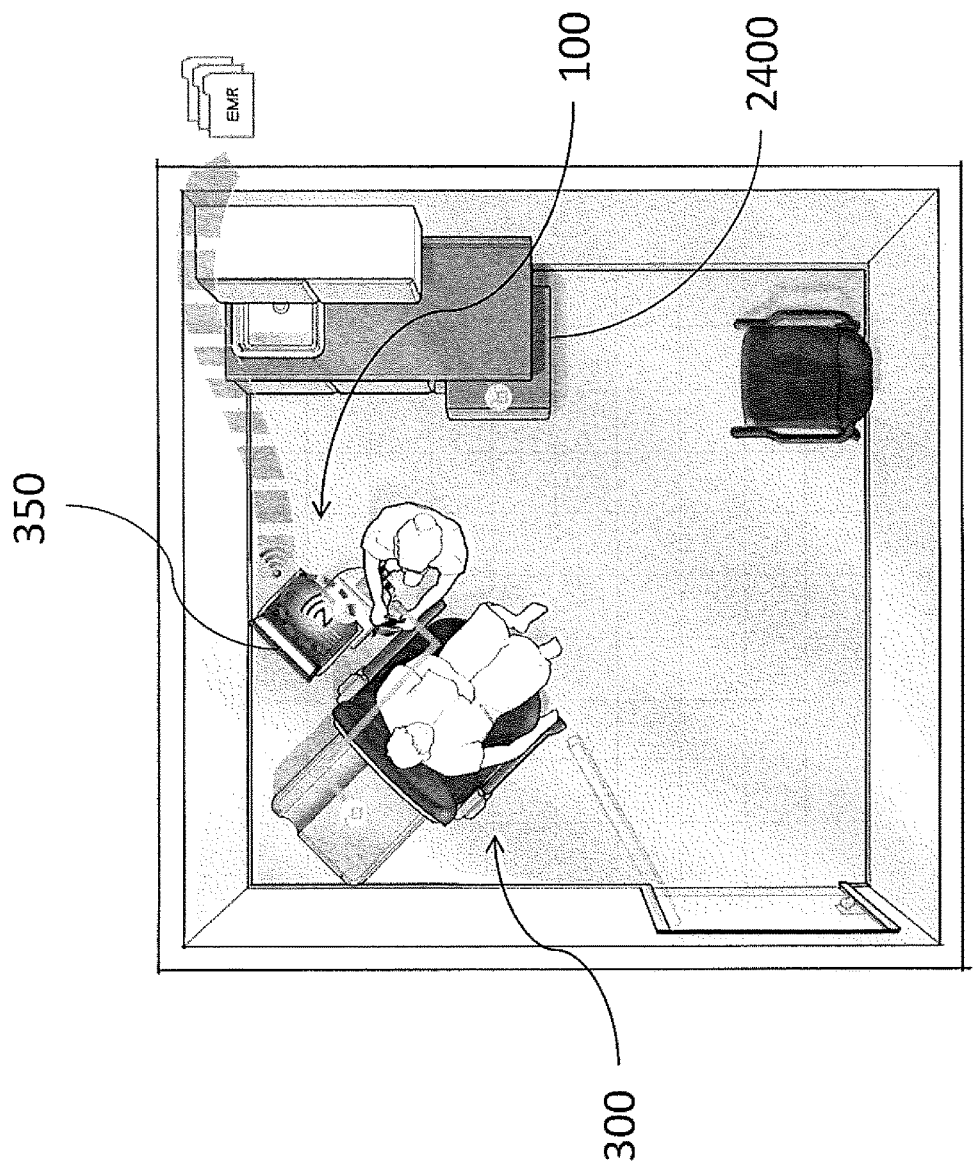
FIG. 39 depicts an overhead diagrammatic view of the communication hub assembly of FIG. 1 mounted in the examination room of FIG. 38, with a communications link established with an EMR system and in-room equipment, and with equipment in the examination room in an unlocked state.

FIGS. 30-39 show an example of steps that could be performed with a hub platform device (100) that is statically located in a medical examination room (5700). A statically located hub platform device (100) might be integrated with a mobile vitals cart (20) as described above with reference to communication hub assembly (10) and as shown in FIGS. 31-35. Alternatively, hub platform device (100) may be integrated into a wall mounted vitals unit that is affixed to a wall or other structure, as shown in FIG. 36-37, a table mounted vitals unit that is affixed to a medical examination table (300) or other stationary fixture as shown in FIGS. 38-39, or any other statically located hub platform device (100). It should therefore be understood that the procedure shown in FIGS. 30-35 may be readily carried out in the setting shown in FIGS. 36-37 and in the setting shown in FIG. 38-39.

Figure 30:
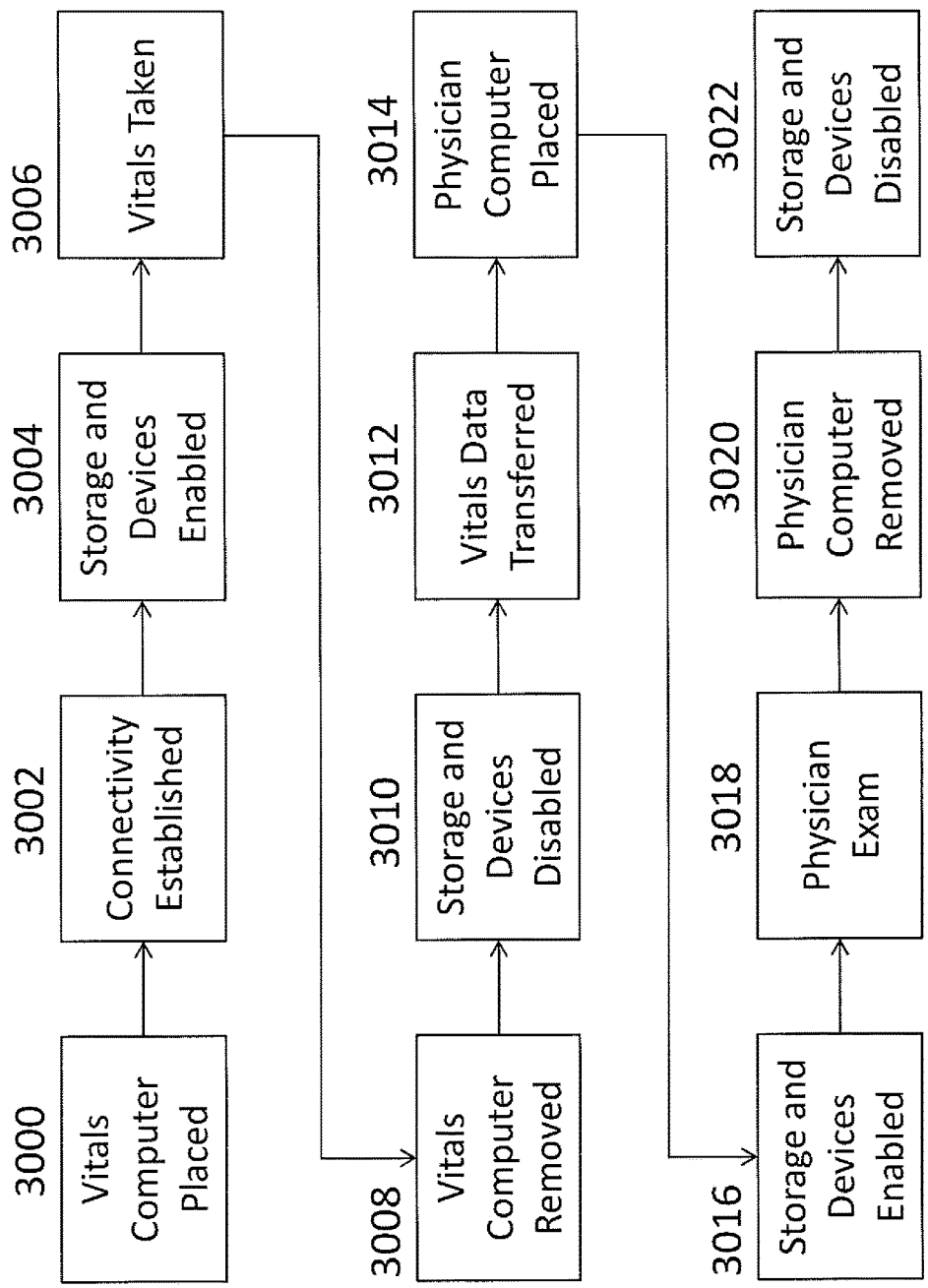
FIG. 30 depicts a flow diagram of an exemplary set of steps that could be performed using the communication hub assembly of FIG. 1.
Figure 31:
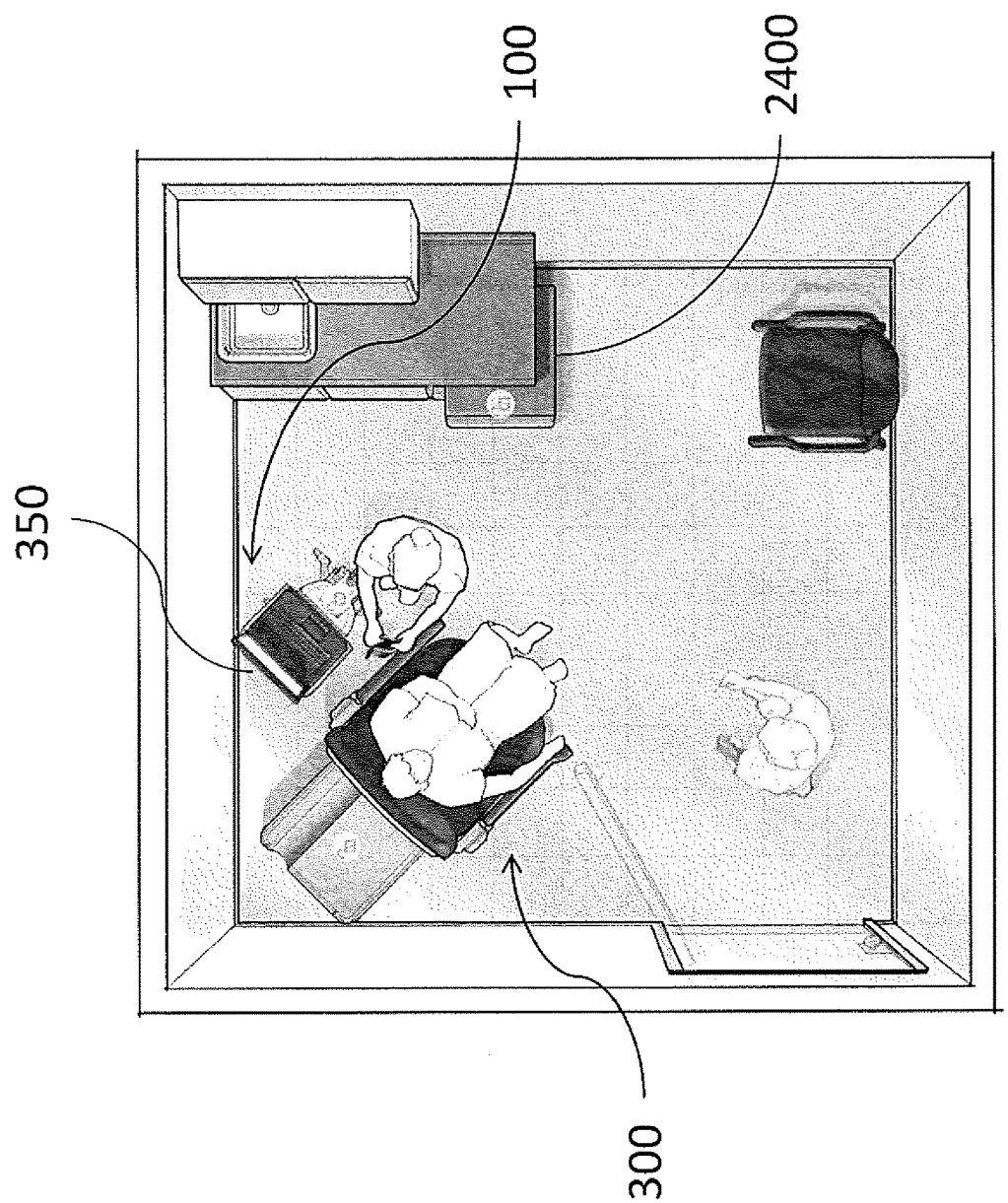
FIG. 31 depicts an overhead diagrammatic view of the communication hub assembly of FIG. 1 located in an examination room where the set of steps of FIG. 30 may be performed.
Figure 32:
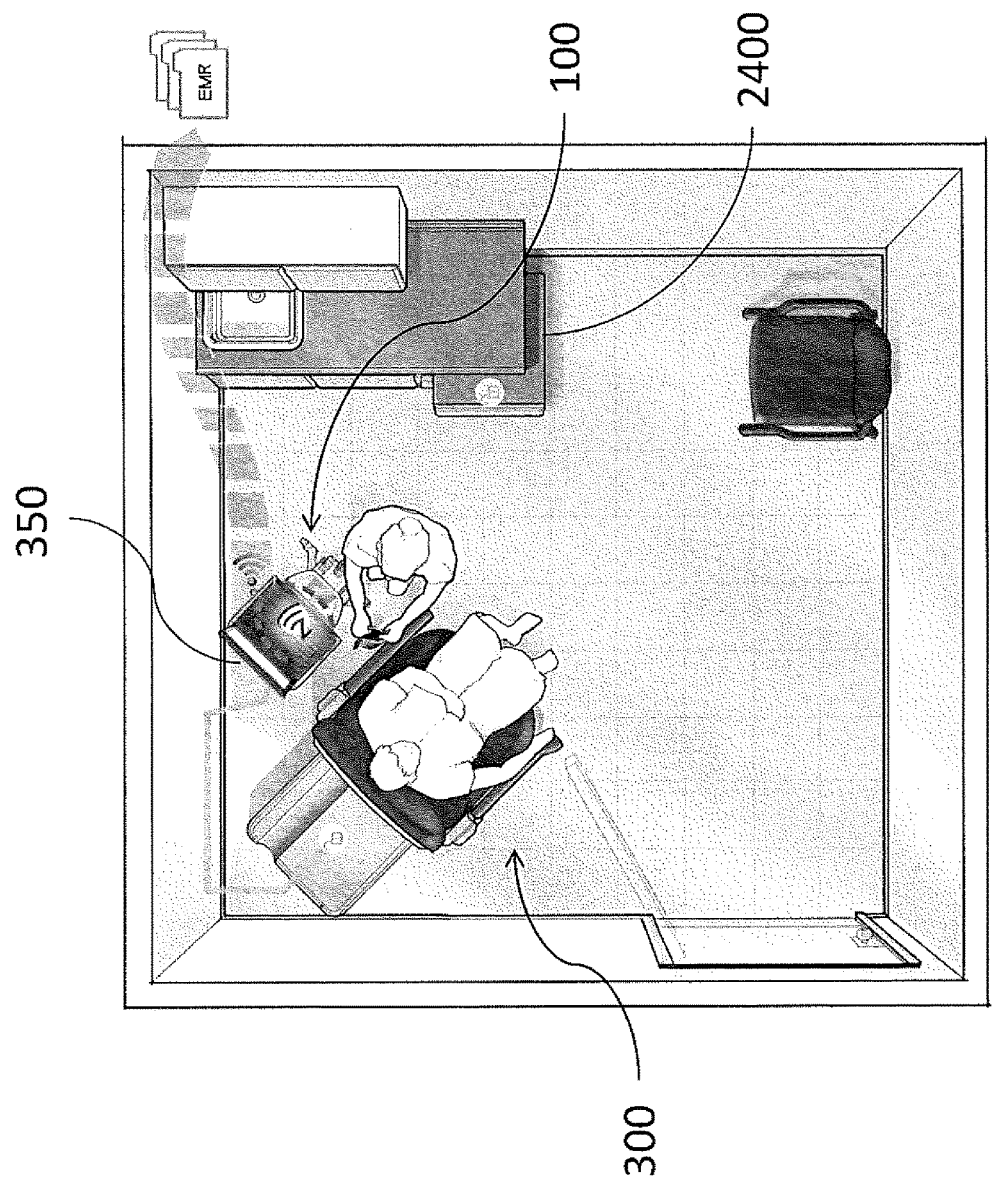
FIG. 32 depicts an overhead diagrammatic view of the communication hub assembly of FIG. 1 located in the examination room of FIG. 31, with a communications link established with an EMR system and in-room equipment, and with equipment in the examination room in an unlocked state.

As shown in FIGS. 30 and 31-32, when a statically located hub platform device (100) is available in a medical examination room (5700), a mobile computer (350) can be placed (3000) on the hub platform device (100) causing connectivity to be established (3002) between the mobile computer (350) and the hub platform device (100). Establishing connectivity (3002) may also extend to devices associated with the hub platform device (100) as well as devices specific to a medical examination room (5700), such as the medical examination table (300) and a storage cabinet (2400), allowing such devices to be interacted with from a local location such as the mobile computer (350) or hub platform device (100); or from a remote location such as the ecosystem server (5704). As an example, once connectivity is established (3002), devices and storage within the medical examination room may be enabled for use and access (3004). More specifically, establishing connectivity (3002) may cause, for example, the medical examination table (300) to be placed into an operative mode, such that it can receive input from an integrated foot pedal or switch, a mobile computer (350), or hub platform device (100). As a further example, establishing connectivity (3002) may result in a storage cabinet (2400) having a lock mechanism disabled, such that the contents of the storage cabinet (2400) can be accessed by medical personnel.

As also shown in FIG. 30, once storage and devices have been enabled (3004), a patient's vitals may be taken (3006) and/or other procedures performed using one or more of the now enabled devices. Once these tasks (3006) are completed, the mobile computer (350) may be removed from the hub platform device (100), causing the connectivity to cease, and causing the previously enabled storage and devices to be disabled (3010).

Figure 33:
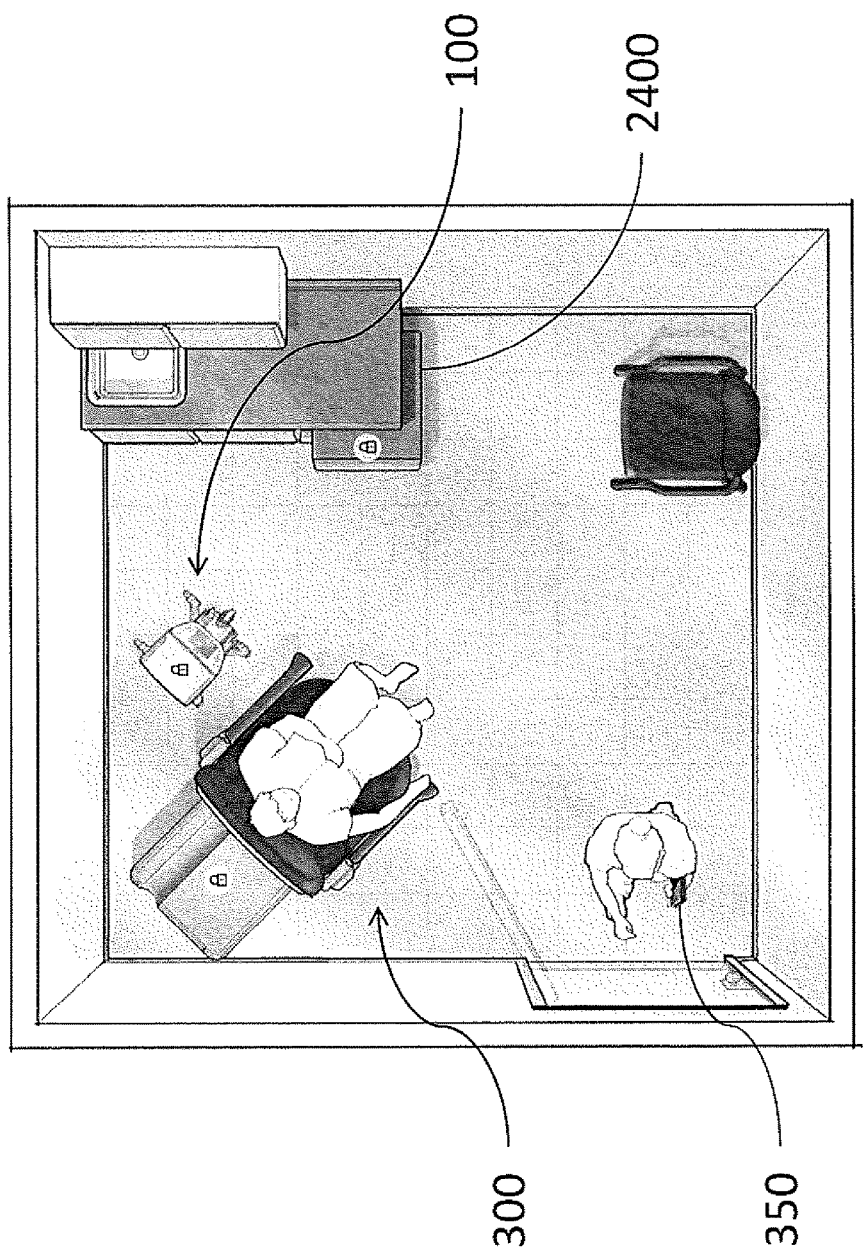
FIG. 33 depicts an overhead diagrammatic view of clinical personnel leaving the communication hub assembly of FIG. 1 in the examination room of FIG. 31, with the communication hub assembly of FIG. 1 and the in-room equipment in a locked state.

As shown in FIGS. 30 and 33, when a medical professional has completed their assigned tasks, they can remove the mobile computer (350) from the hub platform device (100) in preparation for leaving the room. The removal of the mobile computer (350) results in a loss of connectivity, and automatically disables one or more devices in the medical examination room (5700). For example, this could result in automatically disabling the medical examination table (300), preventing a patient from interacting with integrated switches or controls, as well as automatically actuating the locking mechanism for the storage cabinet (2400), preventing a patient from accessing the contents. As with previous examples, upon removal of the mobile computer (350), vitals data can be automatically transferred (3012) to the ecosystem server (5704) and used to update or create a patient's EMR, a physician can be automatically notified, equipment locations can be automatically updated, and/or other actions may be automatically taken.

As shown in FIGS. 30 and 34, when the physician arrives, the physician mobile computer (350) or tablet, smartphone, etc., can be placed (3014) on the hub platform device (100). When the physician mobile computer (350) is placed (3014), one or more devices or storage containers in the room can be re-enabled (3016) by one or more of the hub platform device (100), physician mobile computer (350), or ecosystem server (5704). As an example, when the physician mobile computer (350) is placed (3014), the medical examination table (300) may be enabled for use so that it can be controlled from integrated pedals or switches, or controlled from one or more of the hub platform device (100), mobile computer (350), or ecosystem server (5704). As a further example, the storage cabinet (2400) could have a locking mechanism disabled, such that the storage cabinet (2400) contents can be accessed and used by the physician or other medical personnel present. After one or more devices or storage units are enabled (3016), a physician may perform an examination (3018) using one or more of the ecosystem devices or storage units.

As shown in FIGS. 30 and 35, when the examination is complete (3018), the physician computer (350) is removed (3020) from the hub platform device (100), causing the previously enabled storage and devices to be disabled (3022). For example, this could include automatically disabling the medical examination table (300) so that it cannot be used while medical personnel are absent from the room, automatically enabling the lock mechanism on a storage cabinet (2400) to prevent access to the contents while unsupervised by medical personnel, and/or automatically taking other actions.

Figure 40:
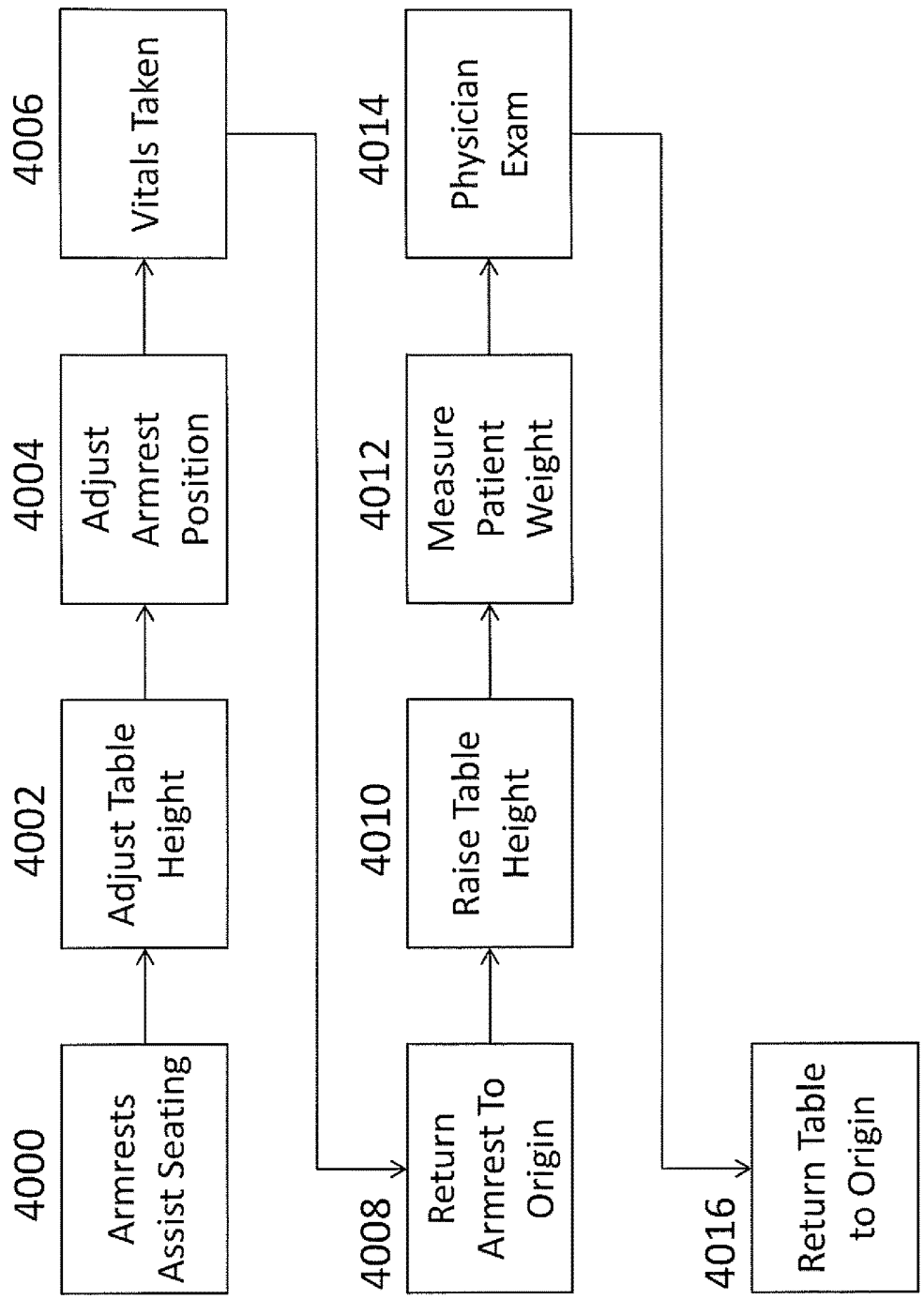
FIG. 40 depicts a flow diagram of an exemplary set of steps that could be performed with a medical examination table in conjunction with the communication hub assembly of FIG. 1.
Figures 41, 42, 43:
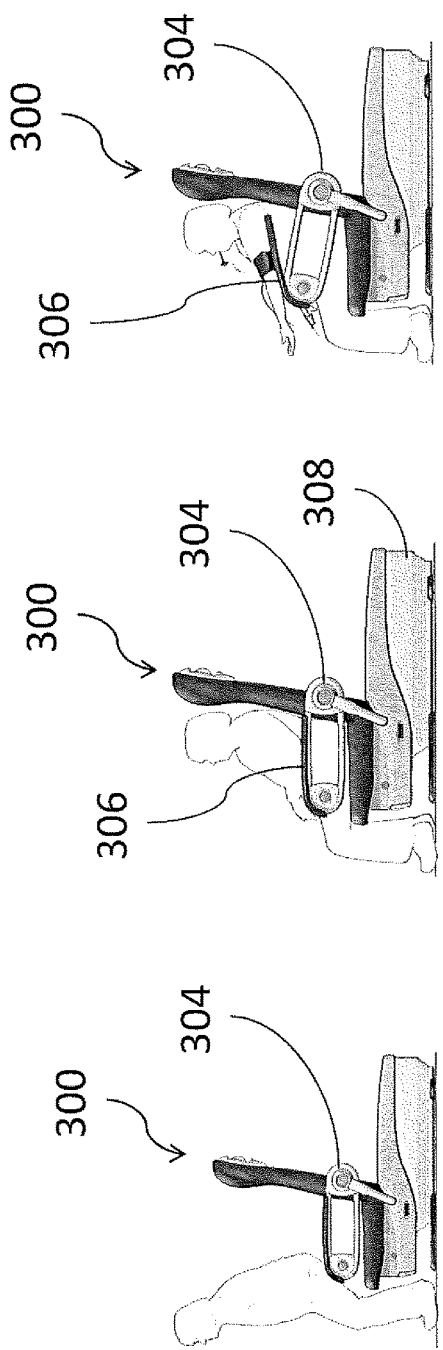
FIG. 41 depicts a side elevation view of an exemplary medical examination table with which the set of steps of FIG. 40 may be performed, with a patient approaching the examination table.
FIG. 42 depicts a side elevation view of the medical examination table of FIG. 41, with the patient seated on the medical examination table.
FIG. 43 depicts a side elevation view of the medical examination table of FIG. 41, with the patient's vitals being checked.

FIGS. 40-52 show an example of steps that could be performed with a medical examination table (300) that may be part of an electronic ecosystem. As shown in FIGS. 40 and 41, when a patient first approaches the medical examination table (300), the integrated armrest (304) may be manually or automatically adjusted to a position that assists the patient in seating (4000). Automatic adjustment may be performed by retrieving a patient specific configuration from the ecosystem server (5704) and communicating it to the medical examination table (300), where an integrated powered armrest (304) may then automatically adjust to the stored configuration. As shown in FIGS. 40 and 42, the medical examination table (300) height may then be manually or automatically adjusted (4002) by, for example, expanding or collapsing an adjustable base (308) to place the patient in a seated position that is both comfortable and allows for accurate measurement of vital information. As with automatic armrest (304) adjustment, automatic adjustment of the medical examination table (300) height may be performed retrieving a saved configuration from the ecosystem server (5704) and communicating it to the medical examination table (300) so that a powered height adjustable base (308) may automatically adjust to the stored configuration.

As shown in FIGS. 40 and 43, once a patient is seated an arm orientation pad (306) of the armrest (304) may be automatically or manually adjusted (4004) to raise or lower a patient arm to a height and position that will allow for accurate measurement of vital information. It should be understood that, in instances where armrest (304) and/or arm orientation pad (306) are powered for automatic adjustment, adjustment (4004) of armrest (304) and/or arm orientation pad (306) may be may be performed retrieving a saved configuration from the ecosystem server (5704) and communicating it to the medical examination table (300) so that armrest (304) and/or arm orientation pad (306) may automatically adjust to the stored configuration.

Figures 44, 45:
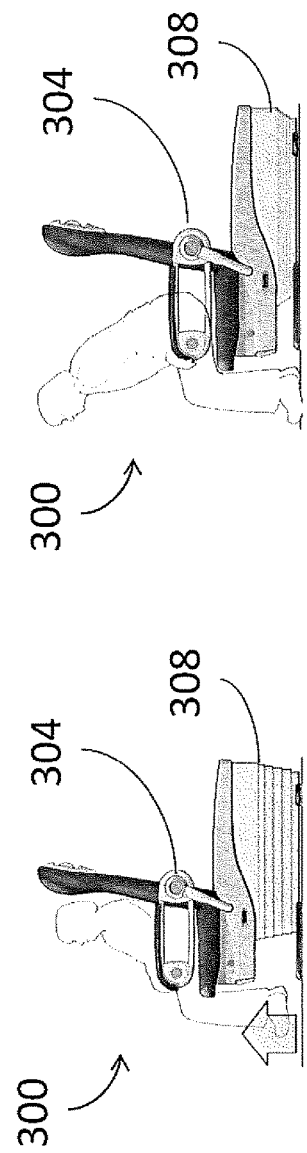
FIG. 44 depicts a side elevation view of the medical examination table of FIG. 41, with the patient's weight being checked.
FIG. 45 depicts a side elevation view of the medical examination table of FIG. 41, with the patient leaving the medical examination table.

Once vital information is recorded (4006) and other related tasks are complete, the arm orientation pad (306) may be manually or automatically returned to its original position (4008). In instances where armrest (304) and/or arm orientation pad (306) are powered for automatic adjustment, ecosystem server (5704) may issue a command to medical examination table (300) to return armrest (304) and/or arm orientation pad (306) to the original position (4008) in response to ecosystem server (5704) receiving data indicating that sufficient vital information has been recorded (4006). As shown in FIGS. 40 and 44, the medical examination table (300) may be raised (4010) via the height adjustable base (308) so that a patient's feet are not bearing any weight, and an integrated weight sensor of the medical examination table (300) may measure and record the weight of the patient (4012). By way of example only, medical examination table (300) may be constructed and operable to measure weight in accordance with at least some of the teachings of U.S. Pub. No. 2013/0247300, entitled "Medical Examination Table with Integrated Scale," published Sep. 26, 2013, the disclosure of which is incorporated by reference herein.

Further, the height adjustable base (308) may be manually or automatically raised (4010) to place the patient and the medical examination table (300) at an optimal height for a physician to examine and interact with a patient (4014). In instances where the patient was originally in a generally supine or reclined position, the backrest of the medical examination table (300) may be automatically actuated to raise the backrest to transition the patient to an upright seated position. As with other automatic adjustments, a saved configuration specific to an examining physician and/or patient may be retrieved from the ecosystem server (5704) and the powered height adjustable base (308) may automatically adjust to the preferred height. As shown in FIGS. 40 and 45, once the examination is complete (4014), the medical examination table (300) may be returned to its original position (4016) so that the patient may safely exit the chair.

Figure 46:
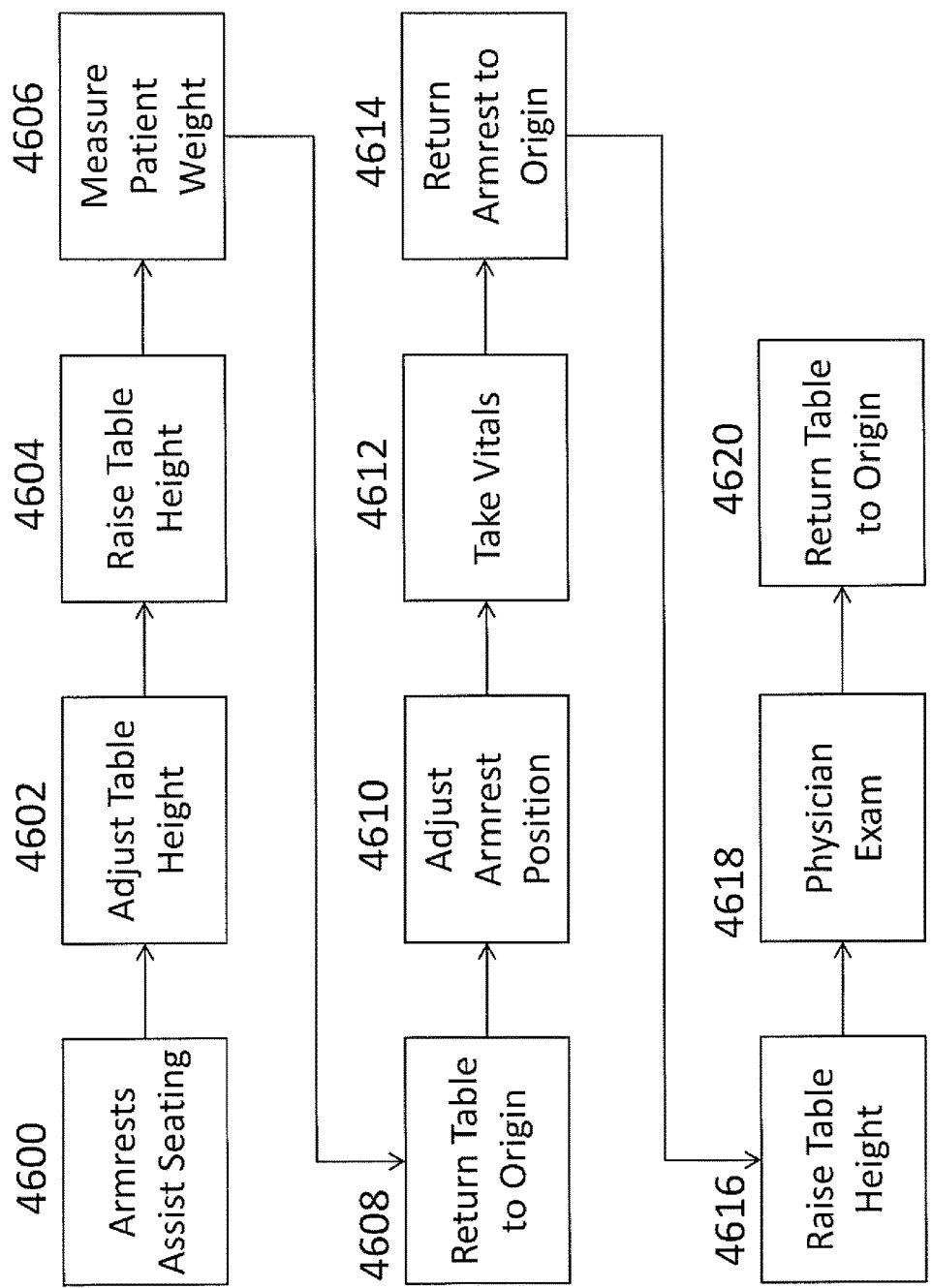
FIG. 46 depicts a flow diagram of another exemplary set of steps that could be performed with a medical examination table in conjunction with the communication hub assembly of FIG. 1.

While FIG. 40 shows one set of steps that could be performed with a medical examination table (300), variations on the order and nature of the steps exist and will be apparent in light of this disclosure. For example, FIGS. 46-52 show one such alternative order of steps described above. When a patient first arrives, the armrests may be manually or automatically adjusted to aid in seating (4600) as shown in FIGS. 46-48. The medical examination table (300) height may be manually or automatically adjusted (4602) via a powered base (308) to an original position. The medical examination table (300) height may be raised (4604) so that a patient's weight may be measured (4606) and then returned to its original position (4608) as shown in FIGS. 46 and 49-50. The arm orientation pad (306) may be manually or automatically positioned (4610) to allow for optimal measurement of vitals (4612) or other related tasks as shown in FIGS. 46 and 50. It should be understood that, in instances where armrest (304) and/or arm orientation pad (306) are powered for automatic adjustment, adjustment (4610) of armrest (304) and/or arm orientation pad (306) may be may be performed retrieving a saved configuration from the ecosystem server (5704) and communicating it to the medical examination table (300) so that armrest (304) and/or arm orientation pad (306) may automatically adjust to the stored configuration.

Once vitals are completed (4612), the arm orientation pad (306) may be returned to its origin position (4614). In instances where armrest (304) and/or arm orientation pad (306) are powered for automatic adjustment, ecosystem server (5704) may issue a command to medical examination table (300) to return armrest (304) and/or arm orientation pad (306) to the origin position (4614) in response to ecosystem server (5704) receiving data indicating that sufficient vital information has been recorded (4612). The medical examination table (300) may be raised (4616) to a position that is ideal for a physician to examine and interact with a patient (4618) as shown in FIGS. 46 and 51. Once the physician examination is complete (4618) the medical examination table (300) can be returned to its original position (4620) so that the patient may safely exit as shown in FIGS. 46 and 52.

Figure 53:
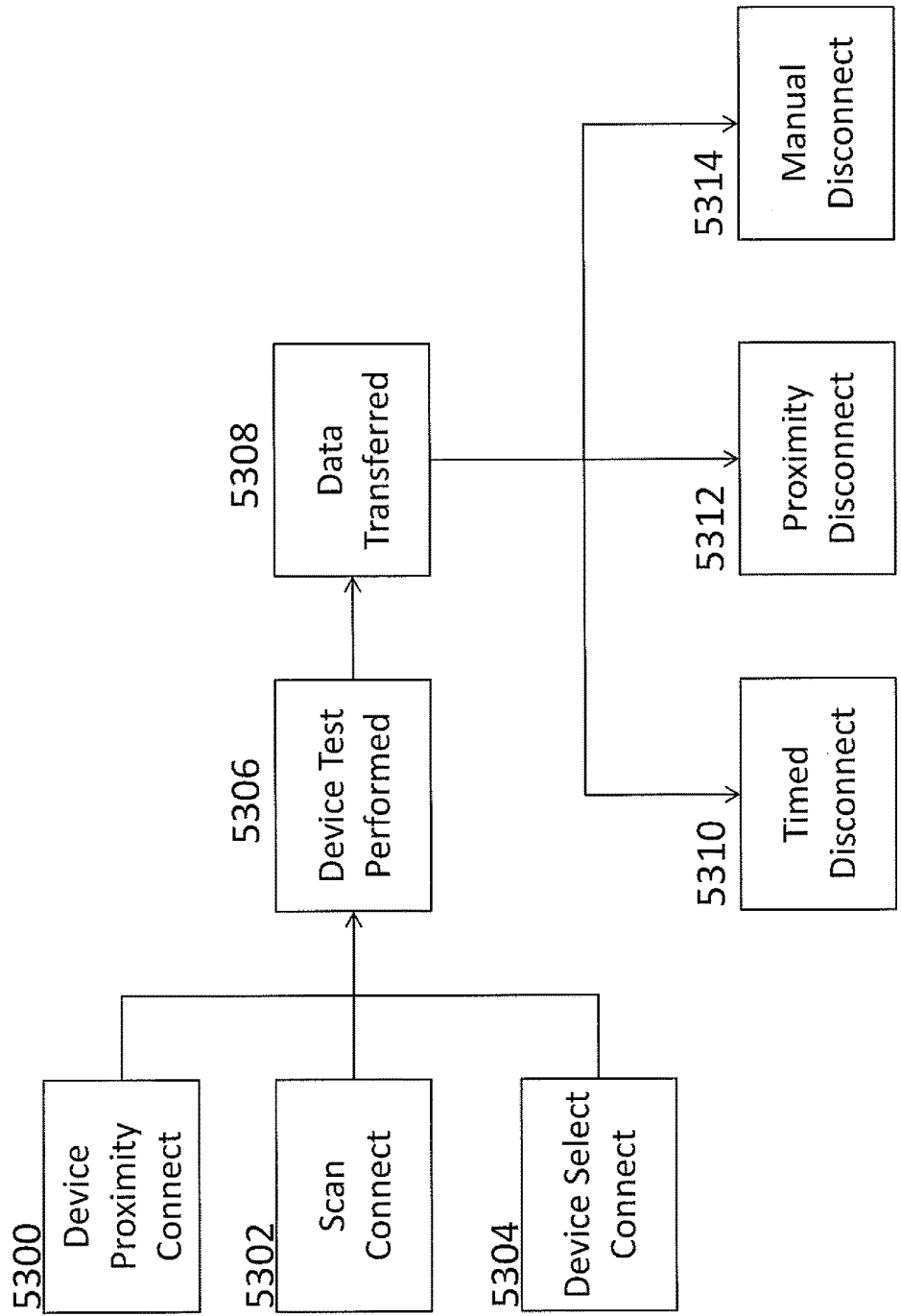
FIG. 53 depicts a flow diagram of an exemplary set of steps that could be performed with the communication hub platform device of FIG. 6 and a medical device.
Figure 56:
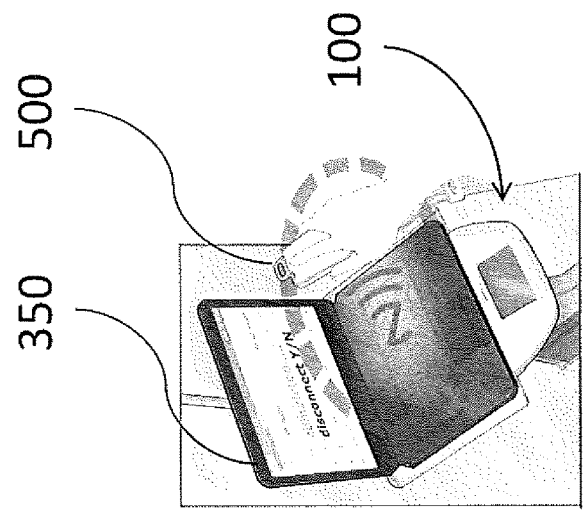
FIG. 56 depicts a perspective view of the communication hub platform device and medical device of FIG. 54, with the ECG device again positioned adjacent to the communication hub platform device.
Figure 55:
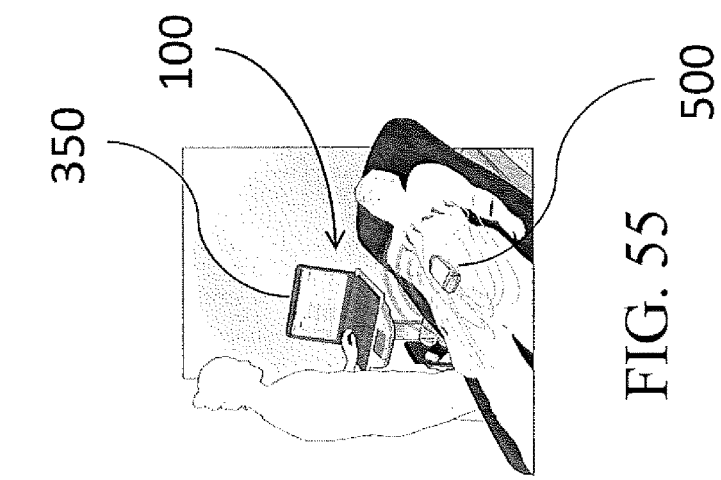
FIG. 55 depicts a perspective view of the communication hub platform device and medical device of FIG. 54, with the ECG device positioned on a patient.
Figure 54:
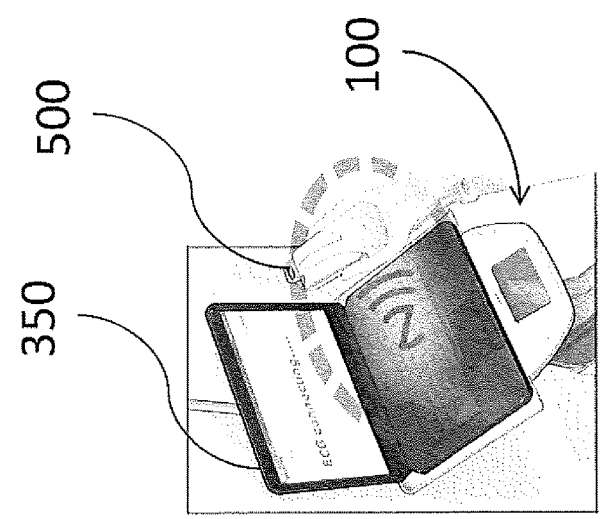
FIG. 54 depicts a perspective view of the communication hub platform device of FIG. 6 and an adjacent ECG device, with which the set of steps of FIG. 53 may be performed.

FIGS. 53-56 show an example of a set of steps that could be performed with a device as part of an electronic ecosystem. FIGS. 54-56 show an electrocardiogram device (ECG) (500) as an example of a device that may be used within an electronic ecosystem, but it should be understood that any suitable medical device may be similarly used. As shown in FIG. 53, when a medical professional wishes to use an ECG (500) within a medical examination room (5700) having a mobile computer (350) paired with a hub platform device (100) and enabled for an electronic ecosystem, the ECG (500) may be connected to the ecosystem by, for example, an automatic proximity based connection (5300), a semi-automated code scan (5302), a manual device selection (5304), and/or using any other suitable technique(s). Proximity based connection (5300) may be achieved by using auto detecting and auto connecting Bluetooth, NFC, infrared, radio, or other wireless communication that can sense a proximate compatible device and automatically connect. Proximity based connection (5300) could be configured such that an ECG (500) connects to the ecosystem when present in the same room by using a mid range wireless technology such as Bluetooth; or could be configured such that an ECG (500) connects to the ecosystem when placed in close proximity to the hub platform device (100) by using a short range wireless technology such as NFC. A code scan connection (5302) may be achieved by providing an optical scanner device as part of the hub platform device (100) that can read image encoded data from a barcode, quick response (QR) code, and/or other image recognition means. Manual device connection (5304) may be achieved by, for example, selecting an ECG (500) identifier from a mobile computer (350) or hub platform device (100) display, selecting a hub platform device (100) from an ECG (500) display, and/or other manual selection means.

As shown in FIGS. 53 and 55, once an ECG (500) has been connected to the ecosystem, an ECG test can be performed (5306) on a patient and data captured by the ECG (500) may be transferred (5308) to the ecosystem server (5704) to create or update patient EMR and/or trigger other actions. As shown in FIGS. 53 and 56, once data has been transferred (5308) the ECG (500) may be disconnected by, for example, a timed disconnection (5310), a proximity disconnection (5312), or a manual disconnection (5314). Timed disconnection (5310) may be achieved by configuring a time limit for connectivity, whereby a recently connected ECG (500) will automatically disconnect after the configured time limit expires. In this manner, an ECG (500) could be configured to automatically disconnect 10 minutes after connection. As another merely illustrative example, ECG (500) could be configured to automatically disconnect 10 minutes after the last data transfer from ECG (500) to hub platform device (100) and/or ecosystem server (5704). A proximity disconnection (5312) may be achieved by configuring a Bluetooth or NFC connection between an ECG (500) and a hub platform device (100) to automatically disconnect when the ECG (500) is determined to be inside or outside a configured range of the hub platform device (100). In this manner, an ECG (500) could be configured to automatically disconnect when the ECG (500) leaves a medical examination room (5700) or is passed near a specific location of a hub platform device (100) such as a deactivation swipe pad. Manual disconnection (5314) may be achieved by allowing a manual selection via a display of the mobile computer (350), hub platform device (100), or ECG (500) that could show active connections and allow them to be terminated. Other suitable ways in which various kinds of medical equipment may interact with hub platform device (100) will be apparent to those of ordinary skill in the art in view of the teachings herein.

Figure 58:
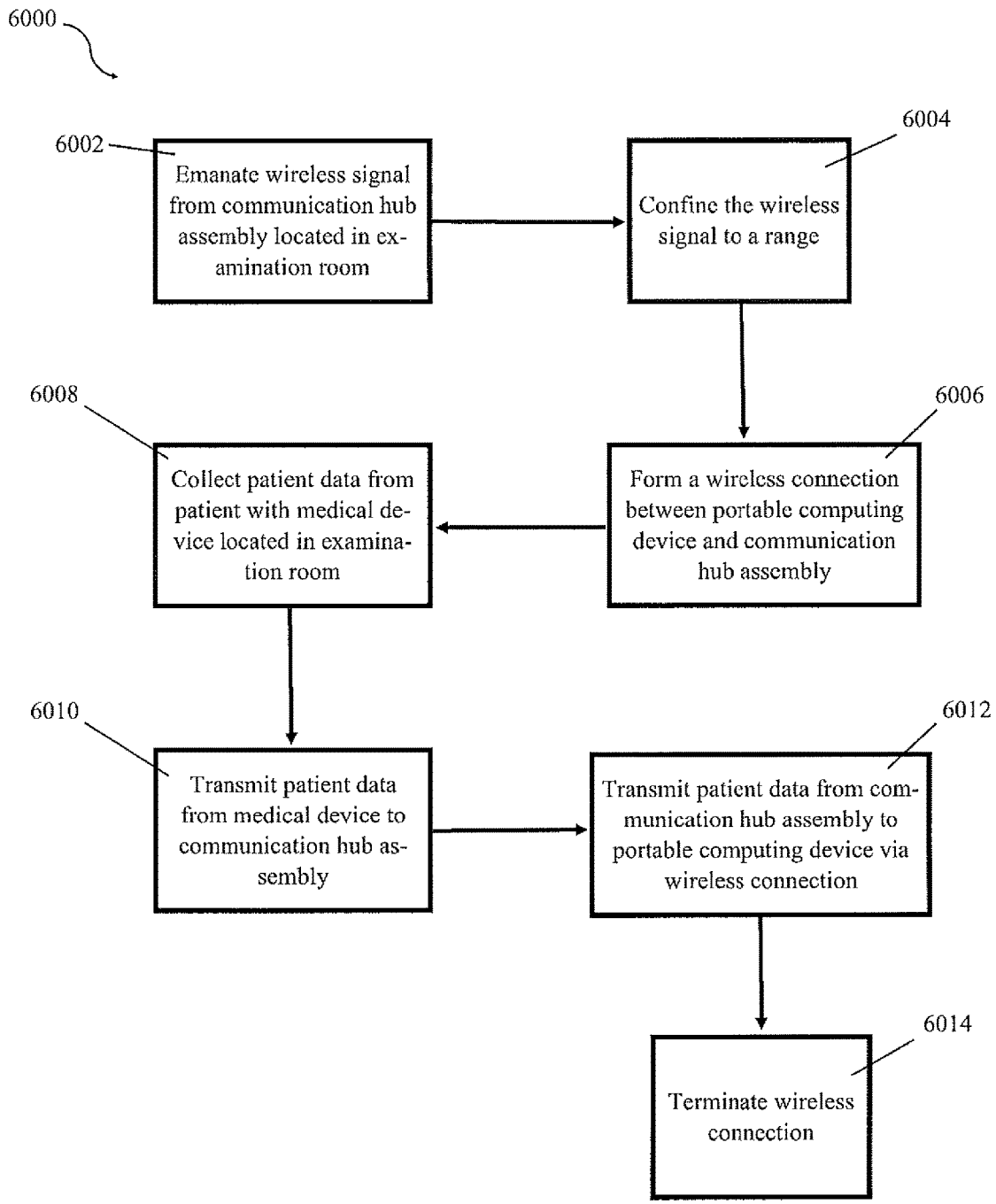
FIG. 58 depicts a flow diagram of an exemplary set of steps that could be performed with a communication hub assembly in conjunction with an examination room.

FIG. 58 shows an example method (6000) comprising steps that could be performed with mobile computer (350) and communication hub assembly (10) in conjunction with examination room (5700). Method (6000) begins with a step (6002), whereby a wireless signal is emanated from communication hub assembly (10) located in examination room (5700). Communication hub assembly (10) may be dynamically located within examination room (5700) and may move from room to room as desired. Alternatively, communication hub assembly (10) may be statically located within examination room (5700). In these embodiments, communication hub assembly (10) may be integrated with a medical device such as a vital signs monitor, an examination table, or a medical cabinet. In other embodiments, communication hub assembly (10) may be integrated with a wall associated with examination room (5700) or otherwise statically connected to examination room (5700). Once the wireless signal is emanating from communication hub assembly (10) located in examination room (5700), step (6002) thereafter moves to a step (6004).

In step (6004), the wireless signal is confined to a range. In this example, the range is smaller than examination room (5700) to prevent the wireless signal from emanating outside of examination room (5700) and to localize the wireless signal in examination room (5700). In some embodiments of communication hub assembly (10), the wireless signal is confined or localized to examination room (5700) by modifying an off-the-shelf communication module such as NFC module (165) or BLE communication module (166) to reduce and restrict the signal range to examination room (5700). In some embodiments of communication hub assembly (10), the off-the-shelf communication module may be modified by attenuating the wireless signal to confine the wireless signal to examination room (5700). The attenuation may be accomplished by providing the off-the-shelf communication module with an additional circuit which acts to attenuate the wireless signal. In some embodiments, communication hub assembly (10) includes an off-the-shelf low energy Bluetooth communication module modified with an additional circuit which acts to attenuate the wireless signal and confine the signal to examination room (5700). After step (6004), method (600) moves to a step (6006).

In step (6006), a wireless connection is formed between mobile computer (350) and communication hub assembly (10) via the wireless signal emanating from communication hub assembly (10). Inasmuch as the wireless signal is confined to examination room (5700), mobile computer (350) must be within the range, and therefore within examination room (5700) in order to form the wireless connection. When mobile computer (350) is outside of examination room (5700), the wireless signal cannot be sensed and the wireless connection cannot be formed. In some embodiments, the wireless connection is formed in response to moving mobile computer (350) within range of the wireless signal and with no input from the operator of mobile computer (350). In these embodiments, the physician or other operator may walk or otherwise move into examination room (5700) and automatically be provided with a link to communication hub assembly (10) through mobile computer (350) without any interaction with either device.

In some other embodiments of communication hub assembly (10), an electronic feature of a medical device located or associated with examination room (5700) may be enabled in response to either moving the mobile computer (350) into range of the wireless signal or forming the wireless connection. For example, a weight sensor of an examination table may be enabled in response to forming the wireless connection, making weight measurement information immediately and automatically available to the physician or other operator of mobile computer (350) upon entry into examination room (5700). In some other embodiments of communication hub assembly (10), a locked medical cabinet located or associated with examination room (5700) may be unlocked in response to either moving the mobile computer (340) into range of the wireless signal or forming the wireless connection. In these embodiments of communication hub assembly (10) the contents of the medical cabinet are immediately and automatically available to the physician or other operator of mobile computer (350) upon entry into examination room (5700) with no interaction from the operator. After the wireless connection is formed in step (6006), method (6000) moves to a step (6008).

In step (6008), patient data from a patient is collected by a medical device located in examination room (5700). Patient data may be collected from medical devices such as examination tables or vital signs monitoring devices. For example, an examination table located in examination room (5700) may have an integrated weight sensor for weighing a patient resting thereupon and collecting patient data regarding weight measurements. In another example, the medical device may be a blood pressure monitor for collecting blood pressure measurements.

In some embodiments of communication hub assembly (10), mobile computing device (350) may provide command or actuation signals over the wireless connection and through communication hub assembly (10) to the medical device. These commands allow the operator of mobile computer (350) to control or actuate the medical device to perform certain activities or collect a particular set of data. For example, the operator of mobile computer (350) may wish to actuate a weight sensor of a medical examination table to collect a patient's weight measurement. To achieve this, the user manipulates mobile computer (350) to transmit command signals over the wireless connection to communication hub assembly (10). These command signals are passed in turn to the medical device to actuate the various features of the medical device. In some embodiments of method (6000), the medical device is free from any onboard or integrated controls and may only be actuated to collect patient data in response to command signals sent by the user through mobile computer (350). In other embodiments, the medical device includes a first set of actuation features available through an onboard interface with the medical device, while a second set of actuation features is provided to mobile computer (350) via communication hub assembly (10). After the medical device collects patient data in step (6008), method (6000) proceeds to a step (6010).

In step (6010), the collected patient data is transmitted from the medical device to communication hub assembly (10). This transmission may be over another wireless connection between the medical device and communication hub assembly (10) or may be over a wired connection. After the patient data is transmitted from the medical device to communication hub assembly (10), step (6010) proceeds to a step (6012).

In step (6012), the patient data is transmitted from communication hub assembly (10) to mobile computer (350) via the wireless connection. Pursuant to the wireless nature of the connection, mobile computer (350) may be situated anywhere within the range and receive the patient data collected by the medical device. The user of mobile computer (350) is thereafter free to observe, manipulate, or further transfer the data as desired. For example, the user may actuate a procedure to further transmit the patient data to a remote server over another wireless connection. Upon completion of step (6012), method proceeds to a step (6014).

In step (6014), the wireless connection is terminated. In some embodiments of method (6000), the termination step may be actuated by mobile computer (350) moving out of the range and/or out of examination room (5700). For example, when the medical examination is completed, the physician may leave examination room (5700), carrying mobile computer (350) to the next examination room. Thus, the wireless connection may be automatically terminated based on mobile computer (350) leaving the range, requiring no interaction with the physician or operator of mobile computer (350).

In some embodiments of method (6000), mobile computer (350) may disable an electronic feature of the medical device or the entire medical device itself in response to the terminating of the wireless connection. In other embodiments of method (6000), mobile computer (350) may lock a medical cabinet located or associated with examination room (5700). In other embodiments of method (6000), the user may be prompted regarding whether to transmit the patient data from mobile computer (350) to a remote server such as ecosystem server (5705) in response to the terminating of the wireless connection.

Figure 59:
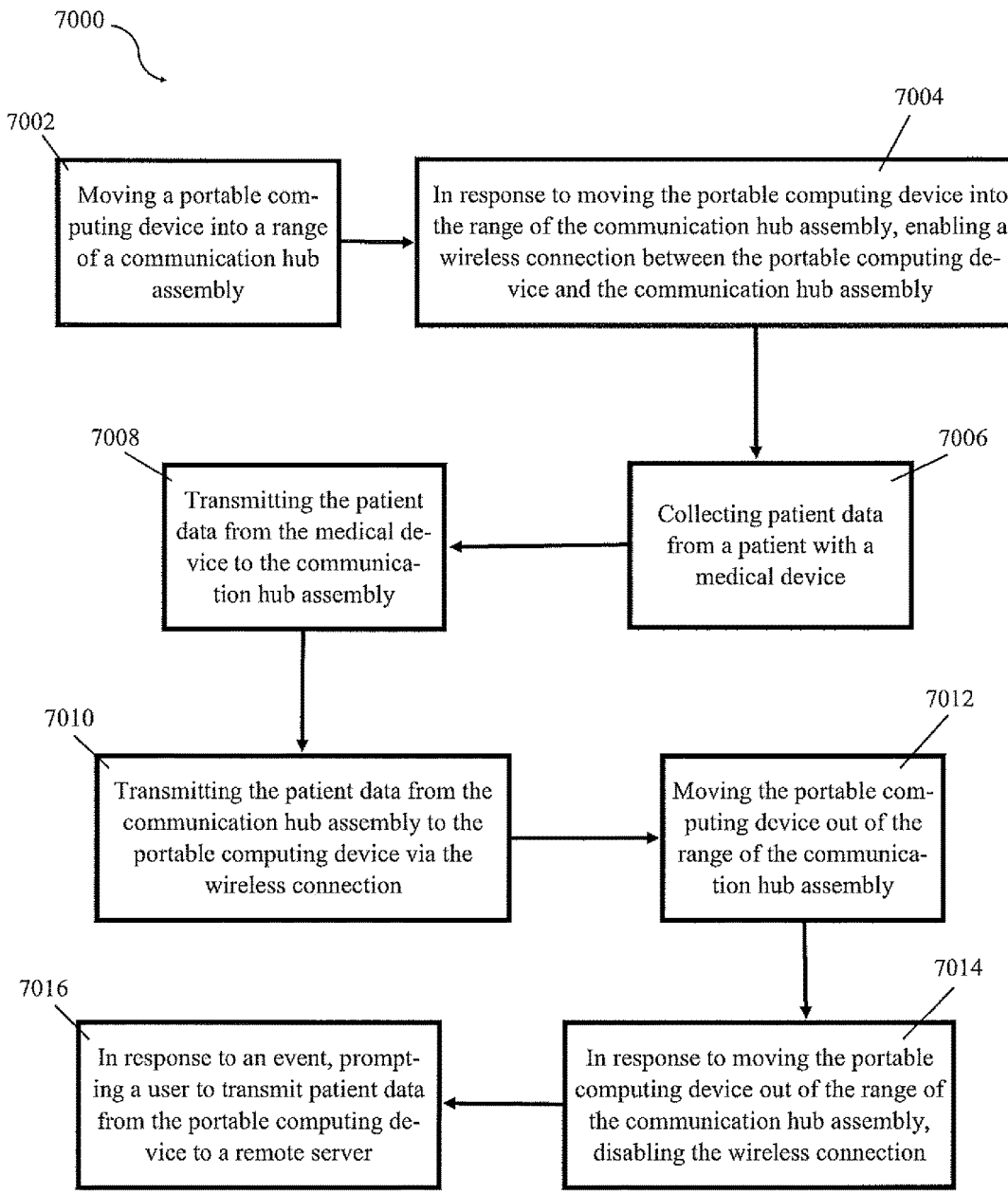
FIG. 59 depicts a flow diagram of an exemplary set of steps that could be performed with a communication hub assembly in conjunction with an examination room.

FIG. 59 shows an example method (7000) comprising steps that could be performed with a mobile computing device such as mobile computer (350) and a communication hub assembly such as communication hub assembly (10). Method may be performed in conjunction with an examination room such examination room (5700).

Method (7000) begins with a step (7002), whereby the portable computing device is moved into a range of the communication hub assembly. Thereafter, step (7002) proceeds to a step (7004). In step (7004), in response to moving the portable computing device into the range of the communication hub assembly, a wireless connection is enabled between the portable computing device and the communication hub assembly. Step (7004) thereafter proceeds to a step (7006), whereby patient data is collected from a patient with a medical device. The collection of data may be actuated by a user through portable computing device. In this scenario, the portable computing device becomes the control or interface for the medical device. Thereafter, step (7006) proceeds to a step (7008), whereby the patient data is transmitted from the medical device to the communication hub assembly. This transmission may be over a wired or a wireless connection between the medical device and the communication hub.

Upon transmitting the patient data from the medical device to the communication hub assembly, step (7008) proceeds to a step (7010). In step (7010), the patient data is transmitted from the communication hub assembly to the portable computing device via the wireless connection. Step (7010) thereafter proceeds to a step (7012), whereby the portable computing device is moved out of the range of the communication hub assembly. The movement may correlate to the physician or other medical personnel leaving the examination room with the portable computing device. Step (7012) thereafter moves to a step (7014).

In step (7014), in response to moving the portable computing device out of the range of the communication hub assembly, the wireless connection is disabled. Step (7014) thereafter moves to a step (7016). In step (7016), in response to an event, the user is prompted regarding whether the user wishes to transmit the patient data from the portable computing device to a remote server. As shown in FIG. 57, the remote server may be embodied in ecosystem server (5704) and database (5706). One example of the event of step (7016) may include disabling the wireless connection. Another example of the event of step (7016) may include moving the portable computing device out of the range of the communication hub assembly.

In some embodiments of method (7000), the medical device may comprise a medical examination table having a patient weight sensor and the patient data may comprise a weight measurement collected by the patient weight sensor. In these embodiments, the weight sensor may be enabled in response to enabling the wireless connection and the weight sensor may be disabled in response to disabling the wireless connection.

III. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method comprising:
   (a) emanating a wireless signal from a communication hub assembly located in an examination room, wherein the communication hub assembly is in communication with a remote server;
   (b) sensing, by a proximity sensor located in the examination room, the presence or absence of a portable computing device in the examination room;
   (c) forming a wireless connection between the portable computing device and the communication hub assembly via the wireless signal in response to the proximity sensor sensing the presence of the portable computing device in the examination room;
   (d) collecting patient data from a patient with a medical device located in the examination room;
   (e) transmitting the patient data from the medical device to the communication hub assembly;

(f) transmitting the patient data from the communication hub assembly to the portable computing device via the wireless connection; and wherein the communication hub assembly maintains communication with the remote server in the absence of the portable computing device in the examination room.

2. The method of claim 1, further comprising:
(a) terminating the wireless connection between the portable computing device and the communication hub assembly in response to the proximity sensor sensing the absence of the portable computing device in the examination room; and
(b) in response to terminating the wireless connection between the portable computing device and the communication hub assembly, prompting a user to transmit the patient data from the portable computing device to the remote server.

3. The method of claim 1, further comprising:
in response to the proximity sensor sensing the presence of the portable computing device in the examination room, enabling an electronic feature of the medical device.

4. The method of claim 1, further comprising:
actuating the medical device via the portable computing device over the wireless connection.

5. The method of claim 1, further comprising:
in response to forming the wireless connection, enabling an electronic feature of the medical device.

6. The method of claim 5, further comprising:
(a) terminating the wireless connection between the portable computing device and the communication hub assembly; and
(b) in response to terminating the wireless connection, disabling the electronic feature of the medical device.

7. The method of claim 1, further comprising:
in response to forming the wireless connection, unlocking a medical cabinet located within the examination room.

8. The method of claim 7, further comprising:
(a) terminating the wireless connection between the portable computing device and the communication hub assembly; and
(b) in response to terminating the wireless connection, locking the medical cabinet.

9. The method of claim 1, wherein the communication hub assembly is statically located in the examination room.

10. The method of claim 1, further comprising:
integrating the communication hub assembly into a vital signs monitor.

11. The method of claim 1, further comprising:
(a) terminating the wireless connection between the portable computing device and the communication hub assembly in response to the proximity sensor sensing the absence of the portable computing device in the examination room; and
(b) in response to terminating the wireless connection between the portable computing device and the communication hub assembly, automatically transmitting the patient data from the portable computing device to the remote server.

12. A method comprising:
(a) moving a portable computing device into a range of a communication hub assembly, wherein the communication hub assembly is in communication with a remote server via a communication link;
(b) in response to moving the portable computing device into the range of the communication hub assembly, enabling a wireless connection between the portable computing device and the communication hub assembly;
(c) in response to enabling the wireless connection between the portable computing device and the communication hub assembly, unlocking a cabinet located within the range of the communication hub assembly;
(d) collecting patient data from a patient with a medical device;
(e) transmitting the patient data from the medical device to the communication hub assembly;
(f) transmitting the patient data from the communication hub assembly to the portable computing device via the wireless connection;
(g) moving the portable computing device out of the range of the communication hub assembly;
(h) in response to moving the portable computing device out of the range of the communication hub assembly, disabling the wireless connection and locking the cabinet;
(i) in response to an event, prompting a user to transmit the patient data from the portable computing device to the remote server; and
wherein the communication link is free of the portable computing device and is maintained when the portable computing device is out of the range of the communication hub assembly.

13. The method of claim 12, wherein the event comprises disabling the wireless connection.

14. The method of claim 12, wherein the event comprises moving the portable computing device out of the range of the communication hub assembly.

15. The method of claim 12, further comprising:
actuating a feature of the medical device via the portable computing device.

16. The method of claim 12, wherein the medical device comprises a medical examination table having a patient weight sensor, wherein the patient data is a weight measurement collected by the patient weight sensor, and further comprising:
(a) in response to enabling the wireless connection, enabling the weight sensor of the medical examination table; and
(b) in response to disabling the wireless connection, disabling the weight sensor of the medical examination table.

17. The method of claim 12, wherein the medical device comprises a medical examination table having an electronic arm rest, and further comprising:
(a) in response to enabling the wireless connection, retrieving a patient specific configuration from the remote server and communicating it to the medical examination table; and
(b) in response to receiving the patient specific communication, automatically adjusting the arm rest to an arm rest position associated with the patient specific configuration.

18. The method of claim 12, wherein the medical device comprises a medical examination table having an adjustable base, and further comprising:
(a) in response to enabling the wireless connection, retrieving a patient specific configuration from the remote server and communicating it to the medical examination table; and (b) in response to receiving the patient specific communication, automatically adjusting the adjustable base to a base position associated with the patient specific configuration.

\* \* \* \* \*